(12) United States Patent
Chantigny et al.

(10) Patent No.: US 7,138,406 B2
(45) Date of Patent: Nov. 21, 2006

(54) MODULATORS OF THE GLUCOCORTICOID RECEPTOR

(75) Inventors: Yves A. Chantigny, Groton, CT (US); Edward F. Kleinman, Pawcatuck, CT (US); Ralph P. Robinson, Gales Ferry, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 308 days.

(21) Appl. No.: 10/615,126

(22) Filed: Jul. 8, 2003

(65) Prior Publication Data

US 2004/0138262 A1 Jul. 15, 2004

Related U.S. Application Data

(60) Provisional application No. 60/394,425, filed on Jul. 8, 2002.

(51) Int. Cl.
*A61K 31/435* (2006.01)
*A61K 31/44* (2006.01)
*C07D 211/04* (2006.01)

(52) U.S. Cl. ............ 514/277; 514/332; 514/364; 514/365; 546/266; 546/285; 548/131; 548/203; 564/172; 560/5

(58) Field of Classification Search ......... 546/285; 514/277
See application file for complete search history.

(56) References Cited

FOREIGN PATENT DOCUMENTS

| EP | 1097709 A2 * | 5/2001 |
| EP | 1 201 649 A1 | 5/2002 |
| EP | 1 201 655 A2 | 5/2002 |
| WO | WO 00/66522 | 11/2000 |
| WO | WO 2000066522 A1 * | 11/2000 |

* cited by examiner

*Primary Examiner*—Kamal A. Saeed
*Assistant Examiner*—Nyeemah Grazier
(74) *Attorney, Agent, or Firm*—Brandon S. Boss; Andrew J. Leon

(57) ABSTRACT

The present invention provides compounds of the formula

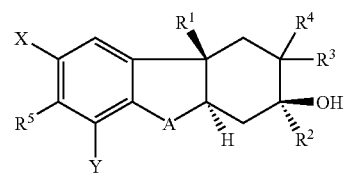

wherein A is of the formula

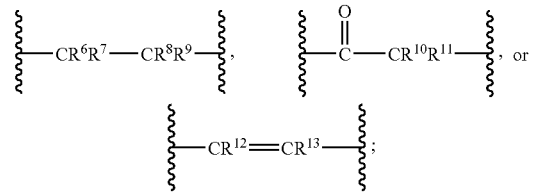

and X, Y, n, $R^1$–$R^{25}$ are as described in the specification which are modulators of the glucocorticoid receptor and are thus useful for the treatment of animals requiring glucocorticoid receptor agonist therapy. Glucocorticoid receptor modulators are useful in the treatment of certain inflammatory conditions.

64 Claims, No Drawings

MODULATORS OF THE GLUCOCORTICOID RECEPTOR

FIELD OF THE INVENTION

The present invention provides compounds which are modulators of the glucocorticoid receptor and as such are useful agents for the treatment of animals, preferably humans, requiring glucocorticoid receptor therapy. Modulators of the glucocorticoid receptor are useful in the treatment of certain inflammatory related conditions. Certain preferred compounds of the invention are dissociated agonists of the glucocorticoid receptor.

BACKGROUND OF THE INVENTION

Nuclear receptors are classically defined as a family of ligand dependent transcription factors, that are activated in response to ligand binding (R. M. Evans, 240 Science, 889 (1988)). Members of this family include the following receptors: glucocorticoid, mineralocorticoid, androgen, progesterone and estrogen. Naturally occurring ligands to these receptors are low molecular weight molecules that play an important role in health and in many diseases. Excesses or deficiencies of these ligands can have profound physiological consequences. As an example, glucocorticoid excess results in Cushing's Syndrome, while glucocorticoid insufficiency results in Addison's Disease.

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisolone.

U.S. Pat. No. 3,683,091 discloses phenanthrene compounds, specifically certain di-7-hydroxy or methyl-2,3,4,4a,9,10-hexahydrophenanthren-2-one and 4a-alkyl derivatives, hydrogenated derivatives, functional derivatives and optically active isomers thereof useful as specific anti-acne agents.

Japanese Patent Application, Publication No. 45014056, published 20 May 1970, discloses the manufacture of 1,2,3,4,9,10,11α,12-octahydro-7-methoxy-12β-butylphenanthren-2β-ol and certain of its derivatives useful as antiandrogenic and antianabolic drugs.

Japanese Patent Application, Publication No. 6-263688, published 20 Sep. 1994, discloses certain phenanthrene derivatives which are interleukin-1 (IL-1) inhibitors. It also discloses their preparation and certain intermediates thereto. International Patent Application Publication No. WO 95/10266, published 20 Apr. 1995, discloses the preparation and formulation of certain phenanthrene derivatives as nitrogen monoxide synthesis inhibitors.

Japanese Patent Application, Publication No. 45-36500, published 20 Nov. 1970, discloses a method of making certain optically active phenanthrene derivatives which are useful as antiandrogenic agents.

European Patent Application, Publication No. 0 188 396, published 23 Jul. 1986, discloses certain substituted steroid compounds, certain processes and intermediates for preparing them, their use and pharmaceutical compositions containing them. These compounds are disclosed to possess antiglucocorticoid activity, and some of them have glucocorticoid activity.

C. F. Bigge et al., J. Med. Chem. 1993, 36, 1977–1995, discloses the synthesis and pharmacological evaluation of a series of octahydrophenanthrenamines and certain of their heterocyclic analogues as potential noncompetitive antagonists of the N-methyl-D-aspartate receptor complex.

P. R. Kanjilal et al., J. Org. Chem. 1985, 50, 857–863, discloses synthetic studies toward the preparation of certain complex diterpenoids.

G. Sinha et al., J. Chem. Soc., Perkin Trans. I (1983), (10), 2519–2528, discloses the synthesis of the isomeric bridged diketones cis-3,4,4a,9,10,10a-hexahydro-1,4a-ethanophenanthren-2(1H),12-dione and trans-3,4,4a,9,10,10a-hexahydro-3,4a-ethanophenanthren-2(1H),12-dione by highly regioselective intramolecular aldol condensations through the stereochemically defined cis- and trans-2,2-ethylenedioxy-1,2,3,4,4a,9,10,10a-octahydrophenanthren-4a-ylacetaldehydes.

U. R. Ghatak, M. Sarkar and S. K. Patra, Tetrahedron Letters No. 32, pp. 2929–2931, 1978, discloses a simple stereospecific route to certain polycyclic bridged-ring intermediates useful in preparing some complex diterpenoids.

P. N. Chakrabortty et al., Indian J. Chem. (1974), 12(9), 948–55, discloses the synthesis of 1α-methyl-1β,4aβ-dicarboxy-1,2,3,4,4a,9,10,10aβ-octahydro-phenanthrene, an intermediate in the synthesis of certain diterpenoids and diterpene alkaloids, and of 1β,4aβ-dicarboxy-1,2,3,4,4a,9,10,10aα-octahydrophenanthrene.

E. Fujita et al., J. Chem. Soc., Perkin Trans. 1 (1974), (1), 165–77, discloses the preparation of enmein from 5-methoxy-2-tetralone via ent-3-β,2-epoxy-3-methoxy-17-norkaurane-6α,16α-diol.

H. Sdassi et al., Synthetic Communications, 25(17), 2569–2573 (1995) discloses the enantioselective synthesis of (R)-(+)-4a-cyanomethyl-6-methoxy-3,4,9,10-tetrahydrophenanthren-2-one, which is a key intermediate in morphinan synthesis.

International Patent Publication WO 00/66522, published Nov. 9, 2000, hereby incorporated by reference in this entirely, discloses other glucocorticoid receptor modulators and methods for the treatment of glucocorticoid mediated disorders. Other glucocorticoid receptor modulators are referred to in two U.S. Non-Provisional application Ser. No. 10/006,215 and Ser. No. 10/012,274 entitled, "Glucocorticoid Receptor Modulators" both filed Oct. 26, 2001.

T. Ibuka et al., Yakugaku Zasshi (1967), 87(8), 1014–17, discloses certain alkaloids of menispermaceous plants.

Japanese Patent 09052899, dated 25 Feb. 1997, discloses certain diterpene or triterpene derivatives which are leukotriene antagonists obtained by extraction from *Tripterygium wilfordii* for therapeutic use.

U.S. Pat. No. 5,696,127 discloses certain nonsteroidal compounds, such as 5H-chromeno[3,4-f]quinolines, which are selective modulators of steroid receptors.

U.S. Pat. No. 5,767,113 discloses certain synthetic steroid compounds useful for concurrently activating glucocorticoid-induced response and reducing multidrug resistance.

Published European Patent Application 0 683 172, published 11 Nov. 1995, discloses certain 11,21-bisphenyl-19- norpregnane derivatives having anti-glucocorticoid activity and which can be used to treat or prevent glucocorticoid-dependent diseases.

D. Bonnet-Delpon et al., Tetrahedron (1996), 52(1), 59–70, discloses certain CF$_3$-substituted alkenes as good partners in Diels-Alder reactions with Danishefsky's diene and in 1,3-dipolar cycloadditions with certain nitrones and non-stabilized azomethine ylides.

International Patent Application Publication No. WO 98/26783, published 25 Jun. 1998, discloses the use of certain steroid compounds with anti-glucocorticoid activity, with the exception of mifepristone, for preparing medicaments for the prevention or treatment of psychoses or addictive behavior.

International Patent Application Publication No. WO 98/27986, published 2 Jul. 1998, discloses methods for treating non-insulin dependent Diabetes Mellitus (NIDDM), or Type II Diabetes, by administering a combination of treatment agents exhibiting glucocorticoid receptor type I agonist activity and glucocorticoid receptor type II antagonist activity. Treatment agents such as certain steroid compounds having both glucocorticoid receptor type I agonist activity and glucocorticoid receptor type II antagonist activity are also disclosed.

International Patent Application Publication No. WO 98/31702, published 23 Jul. 1998, discloses certain 16-hydroxy-11-(substituted phenyl)-estra-4,9-diene derivatives useful in the treatment or prophylaxis of glucocorticoid dependent diseases or symptoms.

Published European Patent Application 0 903 146, published 24 Mar. 1999, discloses that the steroid 21-hydroxy-6,19-oxidoprogesterone (21OH— 6OP) has been found to be a selective antiglucocorticoid and is used for the treatment of diseases associated with an excess of glucocorticoids in the body, such as the Cushing's syndrome or depression.

J. A. Findlay et al, Tetrahedron Letters No. 19, pp. 869–872, 1962, discloses certain intermediates in the synthesis of diterpene alkaloids.

All of the above cited patents, published patent applications and literature publications are hereby incorporated by reference herein in their entirety.

SUMMARY OF THE INVENTION

The present invention relates to a compound of the formula

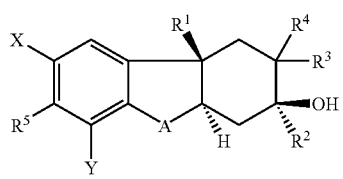

I wherein A is of the formula

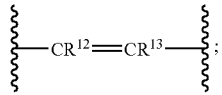

X and Y are each independently hydrogen, fluoro, chloro, bromo, or $(C_1-C_6)$alkyl;

$R^1$ is $(C_2-C_6)$alkyl, $(C_3-C_6)$alkenyl, or optionally substituted benzyl; wherein said benzyl may be optionally substituted with one to three substituents independently selected from HO—, $(C_1-C_6)$alkyl-O—, halo and amino;

$R^2$ is $(C_1-C_6)$alkyl, $(C_2-C_6)$alkenyl, $(C_3-C_6)$alkynyl, $(C_3-C_{10})$cycloalkyl, $(C_6-C_{10})$aryl, $(C_1-C_9)$heterocyclyl, $(C_1-C_9)$heteroaryl, $(C_6-C_{10})$aryl$(C_1-C_4)$alkyl, $(C_1-C_9)$heterocyclyl-$(C_1-C_4)$alkyl, $(C_1-C_9)$heteroaryl-$(C_1-C_4)$alkyl, or $(C_3-C_{10})$cycloalkyl-$(C_1-C_4)$alkyl; wherein each of the aforesaid groups may optionally be substituted with one to three substituents independently selected from halo, $(C_1-C_6)$alkyl, $(C_1-C_6)$alkoxy, or —CF$_3$;

$R^3$ is hydrogen, $(C_1-C_6)$alkyl, $(C_2-C_6)$alkenyl, $(C_2-C_6)$alkynyl, $(C_3-C_{10})$cycloalkyl, $(C_1-C_9)$heterocyclyl, $(C_1-C_9)$heteroaryl, or $(C_6-C_{10})$aryl; wherein each of the aforesaid groups may optionally be substituted with one to three substituents independently selected from HO—, $(C_1-C_6)$alkyl-O—, halo and amino;

$R^4$ is HO— or $R^{14}R^{15}N$—;

$R^5$ is a radical selected from the group consisting of hydrogen, halo, $(C_1-C_6)$alkyl, $(C_2-C_6)$alkenyl, $(C_3-C_6)$alkynyl, $(C_3-C_{10})$cycloalkyl, $(C_6-C_{10})$aryl-, $(C_1-C_9)$heteroaryl-, $(C_1-C_9)$heterocyclic-, —OH, $(C_1-C_6)$alkyl-O—, $(C_3-C_{10})$cycloalkyl-O—, $(C_6-C_{10})$aryl-O—, $(C_1-C_9)$heteroaryl-O—, $(C_1-C_9)$heterocyclic-O—, $(C_3-C_{10})$cycloalkyl-$(C_1-C_6)$alkyl-O—, $(C_6-C_{10})$aryl-$(C_1-C_6)$alkyl-O—, $(C_1-C_9)$heteroaryl-$(C_1-C_6)$alkyl-O—, $(C_1-C_9)$heterocyclic-$(C_1-C_6)$alkyl-O—, $R^{16}R^{17}N$—(C=O)—, $R^{16}$—(C=O)—$(R^{25}$—N)—, $R^{16}R^{17}$—N—SO$_2$—, $R^{18}$—SO$_2$—, $R^{18}$—SO$_2$—(NR$^{19}$)—, $R^{18}$—SO$_3$—, —C≡N, $R^{18}$—(C=O)—O—, $R^{18}$—(C=O)—, $R^{16}R^{17}N$—(C=O)—O—, $R^{16}R^{17}N$—(C=O)—(R$^{25}$—N)—, $R^{19}$—O—(C=O)—(R$^{25}$—N)—, and $R^{19}$—O—(C=O)—; wherein each of said $(C_1-C_6)$alkyl, $(C_3-C_{10})$cycloalkyl, $(C_6-C_{10})$aryl, $(C_1-C_9)$heteroaryl, $(C_1-C_9)$heterocyclic moieties of said $(C_1-C_6)$alkyl, $(C_6-C_{10})$aryl-, $(C_1-C_9)$heteroaryl-, $(C_1-C_9)$heterocyclic-, $(C_1-C_6)$alkyl-O—, $(C_3-C_{10})$cycloalkyl-O—, $(C_6-C_{10})$aryl-O—, $(C_1-C_9)$heteroaryl-O—, $(C_1-C_9)$heterocyclic-O—, $(C_3-C_{10})$cycloalkyl-$(C_1-C_6)$alkyl-O—, $(C_6-C_{10})$aryl-$(C_1-C_6)$alkyl-O—, $(C_1-C_9)$heteroaryl-$(C_1-C_6)$alkyl-O— and $(C_1-C_9)$heterocyclic-$(C_1-C_6)$alkyl-O— radicals, may optionally be substituted with one to three substituents independently selected from the group consisting of $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl(CH$_2$)$_n$—, $(C_1-C_9)$heterocyclic, halo, HO—, HO—(C=O)—, $R^{20}$—O—(C=O)—, $R^{21}$—(C=O)—, $R^{22}$—CO$_2$—, N≡C—, $R^{23}R^{24}N$—, $R^{23}R^{24}N$—$(C_1-C_6)$alkyl-, $R^{23}R^{24}N$—(C=O)—, $R^{23}R^{24}$—N—SO$_2$—, $R^{21}$—SO$_2$—, $R^{21}$—SO$_2$—(NR$^{21}$)$R^{21}$—SO$_3$—, $R^{21}$(C=O)—NH—, $R^{21}$ (C=O)—[N—$(C_1-C_6)$alkyl]-, $R^{21}$ (C=O)—NH—$(C_1-C_6)$alkyl-, and $R^{21}$(C=O)—[N—$(C_1-C_6)$ alkyl]-$(C_1-C_6)$alkyl-; wherein said $(C_3-C_{10})$cycloalkyl, $(C_6-C_{10})$aryl, $(C_1-C_9)$heteroaryl(CH$_2$)$_n$—, $(C_1-C_9)$heterocyclic substituents may optionally be substituted on a ring carbon or nitrogen by one to three members per ring independently selected from halo, $(C_1-C_6)$alkyl, and $(C_1-C_6)$alkoxy;

n is an integer from zero to four;

each of $R^6$, $R^7$, $R^8$ and $R^9$ is independently selected from the group consisting of hydrogen, $(C_1-C_6)$alkyl, fluoro and —OH;

each of $R^{10}$ and $R^{11}$ is independently selected from the group consisting of hydrogen and $(C_1-C_6)$alkyl;

each of $R^{12}$ and $R^{13}$ is independently selected from the group consisting of hydrogen, fluoro and $(C_1-C_6)$alkyl;

each of $R^{14}$ and $R^{15}$ is independently selected from hydrogen or $(C_1-C_4)$alkyl;

each of $R^{16}$ and $R^{17}$ is independently selected from hydrogen, $(C_1-C_6)$alkyl, $(C_6-C_{10})$aryl, $(C_1-C_9)$heteroaryl, $(C_1-C_9)$heterocyclic, $(C_1-C_9)$heteroaryl$(C_1-C_6)$alkyl, $(C_6-C_{10})$aryl$(C_1-C_6)$alkyl, $(C_1-C_9)$heterocyclic$(C_1-C_6)$alkyl, HO—$(C_1-C_6)$alkyl, amino-$(C_1-C_6)$alkyl-, $(C_1-C_6)$alkylamino-$(C_1-C_6)$alkyl-, and $[(C_1-C_6)$alkyl$]_2$amino-$(C_1-C_6)$alkyl-; wherein said each of said $(C_6-C_{10})$aryl, $(C_1-C_9)$heteroaryl, and $(C_1-C_9)$heterocyclic moieties of said $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl and $(C_1-C_9)$heterocyclic-$(C_1-C_6)$alkyl, may optionally be substituted with one to three substituents independently selected from the group consisting of halo, $(C_1-C_6)$alkyl or $(C_1-C_6)$alkoxy, or $R^{16}$ and $R^{17}$ are taken together to form an azetidinyl, pyrrolidinyl, piperidinyl, piperazinyl, $(C_1-C_6)$alkyl-piperazinyl, or morpholinyl ring;

$R^{18}$ is hydrogen, $(C_1-C_6)$alkyl, $(C_6-C_{10})$aryl or $(C_1-C_9)$heteroaryl; wherein said $(C_1-C_6)$alkyl may optionally be substituted with a substituent selected from the group consisting of HO—, amino, $(C_1-C_6)$alkylamino, $[(C_1-C_6)$alkyl$]_2$amino, $(C_6-C_{10})$aryl, $(C_1-C_9)$heteroaryl, $(C_1-C_9)$heterocyclic, $(C_1-C_6)$alkoxy, HO—(C=O)—, $(C_1-C_6)$alkyl-O—(C=O)—, $(C_1-C_6)$alkyl-(C=O)—, N≡C—, $[(C_1-C_6)$alkyl$]_2$N—(C=O)— and $(C_1-C_6)$alkyl(C=O)—NH—;

$R^{19}$ is hydrogen or $(C_1-C_6)$alkyl;

$R^{20}$ is hydrogen or $(C_1-C_6)$alkyl;

$R^{21}$ is hydrogen or $(C_1-C_6)$alkyl;

$R^{22}$ is hydrogen or $(C_1-C_6)$alkyl;

each of $R^{23}$ and $R^{24}$ is independently selected from hydrogen, $(C_1-C_6)$alkyl, $(C_6-C_{10})$aryl, $(C_1-C_9)$heteroaryl, $(C_1-C_9)$heterocyclic, $(C_1-C_9)$heteroaryl$(C_1-C_6)$alkyl, $(C_6-C_{10})$aryl$(C_1-C_6)$alkyl, $(C_1-C_9)$heterocyclic$(C_1-C_6)$alkyl, HO—$(C_1-C_6)$alkyl, N≡C—$(C_1-C_6)$alkyl, amino-$(C_1-C_6)$alkyl-, $(C_1-C_6)$alkylamino-$(C_1-C_6)$alkyl-, and $[(C_1-C_6)$alkyl$]_2$amino-$(C_1-C_6)$alkyl-; wherein said each of said $(C_6-C_{10})$aryl, $(C_1-C_9)$heteroaryl, and $(C_1-C_9)$heterocyclic moieties of said $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl and $(C_1-C_9)$heterocyclic-$(C_1-C_6)$alkyl, may optionally be substituted with one to three substituents independently selected from the group consisting of halo, $(C_1-C_6)$alkyl or $(C_1-C_6)$alkoxy, or $R^{23}$ and $R^{24}$ are taken together to form an azetidinyl, pyrrolidinyl, piperidinyl, piperazinyl, $(C_1-C_6)$alkyl-piperazinyl, or morpholinyl ring;

$R^{25}$ is hydrogen or $(C_1-C_6)$alkyl;

or pharmaceutically acceptable salts or prodrugs thereof.

The active compounds of the present invention are named according to the IUPAC or CAS nomenclature system.

In one way of naming the compounds of the present invention, the carbon atoms in the ring may be numbered as shown in the following simplified structure:

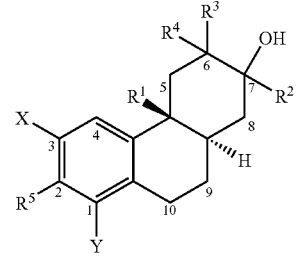

Alternatively, another way of naming the compounds of the present invention, the carbon atoms in the ring may be numbered as shown in the following simplified structure:

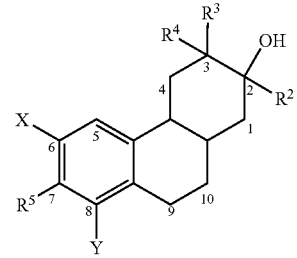

The carbon atom content of various hydrocarbon-containing moieties is indicated by a prefix designating the minimum and maximum number of carbon atoms in the moiety, i.e., the prefix $C_i-C_j$ indicates a moiety of the integer "i" to the integer "j" carbon atoms, inclusive. Thus, for example, $C_1-C_3$ alkyl refers to alkyl of one to three carbon atoms, inclusive, or methyl, ethyl, propyl and isopropyl, and all isomeric forms and straight and branched forms thereof.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the compounds of formula I. Atropisomers refer to compounds of formula I that can be separated into rotationally restricted isomers.

The present invention also includes polymorphs of compounds of formula I. Polymorphs are distinct crystalline forms of the compounds, salts or prodrugs of formula I.

The compounds of this invention may contain olefin-like double bonds. When such bonds are present, the compounds of the invention exist as cis and trans configurations and as mixtures thereof.

Examples of alkyl of one to nine carbon atoms, inclusive, are methyl, ethyl, propyl, butyl, pentyl, hexyl, heptyl, octyl, and nonyl, and all isomeric forms and straight and branched forms thereof.

Examples of alkenyl of two to five carbon atoms, inclusive, are ethenyl, propenyl, butenyl, pentenyl, and all isomeric forms and straight and branched forms thereof.

Examples of alkynyl of two to five carbon atoms, inclusive, are ethynyl, propynyl, butynyl, pentynyl and all isomeric forms and straight and branched forms thereof.

The terms cycloalkyl, cycloalkenyl and cycloalkynyl refer to cyclic forms of alkyl, alkenyl and alkynyl, respectively. Exemplary $(C_3-C_8)$cycloalkyl groups are cyclopropyl, cyclobutyl, cyclopentyl, cyclohexyl, cycloheptyl and cyclooctyl.

The term halo includes chloro, bromo, iodo and fluoro.

The term aryl refers to an optionally substituted six-membered aromatic ring, including polyaromatic rings. Examples of aryl include phenyl, naphthyl and biphenyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^2$ or $R^5$ heteroaryls).

The term "heterocyclic" as used herein refers to a cyclic group containing 1–9 carbon atoms and 1 to 4 hetero atoms selected from N, O, S or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Preferred heterocyclics include tetrahydrofuranyl, pyrrolidinyl, piperidinyl, piperazinyl and morpholinyl.

Embodiment as used herein refers to specific groupings of compounds or uses into discrete subgenera. Such subgenera may be cognizable according to one particular substituent such as a specific $R^2$ group. Other subgenera are cognizable according to combinations of various substituents, such as all compounds wherein $R^2$ is optionally substituted $(C_6-C_{10})$ aryl and $R^5$ is hydroxy. The phrase "in combination with each of the aforementioned embodiments" refers to combinations of the identified embodiment with each embodiment previously identified in the specification. Thus an embodiment of compounds wherein $R^5$ is hydroxy "in combination with each of the aforementioned embodiments" refers to additional embodiments comprising combinations of the $R^5$ hydroxy embodiment with each embodiment previously identified in the specification.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$ alkylcarbamoyl-$(C_1-C_2)$alkyl and piperidino-, pyrrolidino- or morpholino$(C_2-C_3)$alkyl.

More specifically, the present invention relates to compounds of formula I, wherein said compound is the stereoisomer of the formula

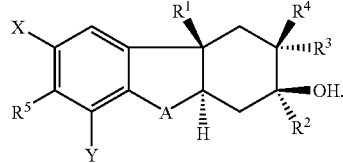

1a

Another embodiment of the present invention relates to compounds of formula I, wherein said compound is the stereoisomer of the formula

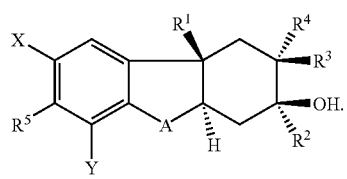

1b

Another embodiment of the present invention relates to compounds of formula I, wherein said compound is the stereoisomer of the formula

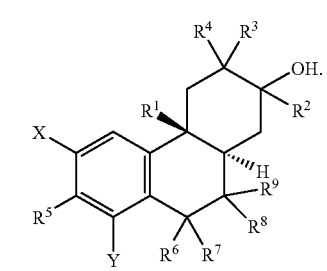

1c

Another embodiment of the present invention relates to compounds of formula I, wherein said compound is the stereoisomer of the formula

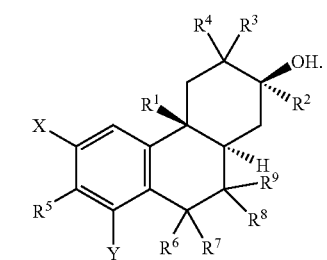

1d

Another embodiment of the present invention relates to compounds of formula I, wherein said compound is the stereoisomer of the formula

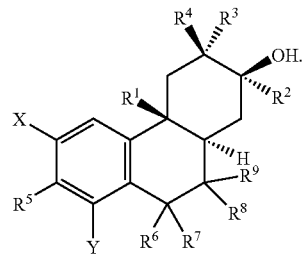

1e

Another embodiment of the present invention relates to compounds of formula I, wherein said compound is the stereoisomer of the formula

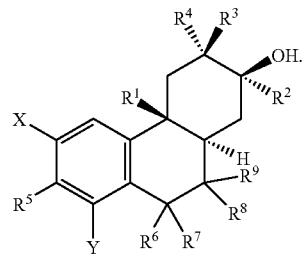

1f

Another embodiment of the present invention relates to compounds of formula I, wherein said compound is the stereoisomer of the formula

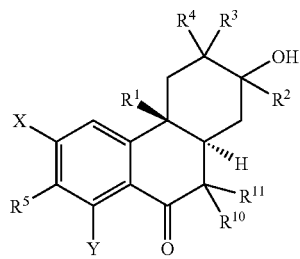

1g

Another embodiment of the present invention relates to compounds of formula I, wherein said compound is the stereoisomer of the formula

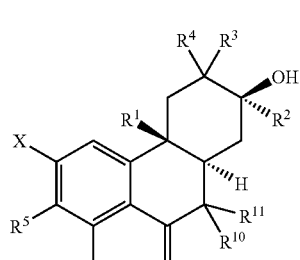

1h

Another embodiment of the present invention relates to compounds of formula I, wherein said compound is the stereoisomer of the formula

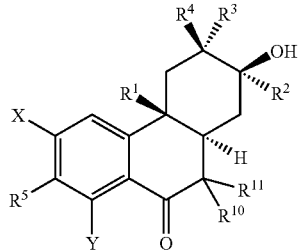

1i

Another embodiment of the present invention relates to compounds of formula I, wherein said compound is the stereoisomer of the formula

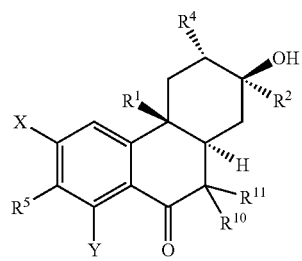

1j

Another embodiment of the present invention relates to compounds of formula I, wherein said compound is the stereoisomer of the formula 1k Another embodiment of the present invention relates to compounds of formula I, wherein said compound is the stereoisomer of the formula

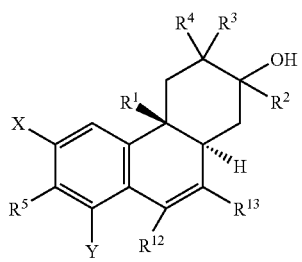

1l

Another embodiment of the present invention relates to compounds of formula I, wherein said compound is the stereoisomer of the formula

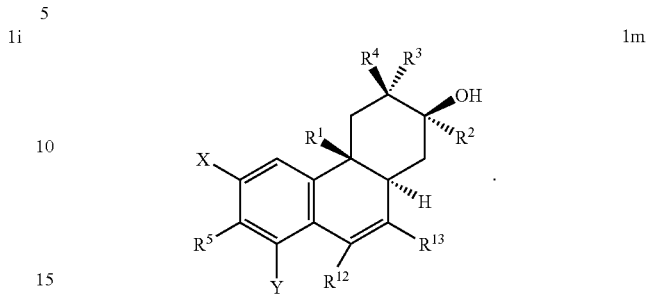

1m

Another embodiment of the present invention relates to compounds of formula I, wherein said compound is the stereoisomer of the formula 1n

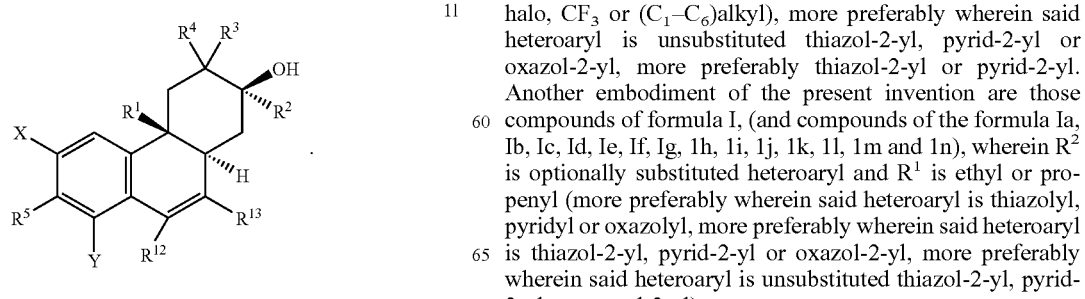

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^1$ is ethyl or propenyl.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is optionally substituted $(C_6-C_{10})$aryl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^2$ is optionally substituted aryl and $R^1$ is ethyl or propenyl.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is $(C_1-C_9)$heteroaryl, more preferably $(C_3-C_5)$heteroaryl, more preferably wherein said heteroaryl is thiazolyl, pyridyl or oxazolyl, more preferably wherein said heteroaryl is thiazol-2-yl, pyrid-2-yl or oxazol-2-yl (optionally substituted with one to three, more preferably one to two, more preferably one, substituent independently selected from halo, $CF_3$ or $(C_1-C_6)$alkyl), more preferably wherein said heteroaryl is unsubstituted thiazol-2-yl, pyrid-2-yl or oxazol-2-yl, more preferably thiazol-2-yl or pyrid-2-yl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^2$ is optionally substituted heteroaryl and $R^1$ is ethyl or propenyl (more preferably wherein said heteroaryl is thiazolyl, pyridyl or oxazolyl, more preferably wherein said heteroaryl is thiazol-2-yl, pyrid-2-yl or oxazol-2-yl, more preferably wherein said heteroaryl is unsubstituted thiazol-2-yl, pyrid-2-yl or oxazol-2-yl).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is optionally substituted phenyl, more preferably unsubstituted phenyl. Another embodiment of the present invention are those compounds of formula I, (and compounds of the formula Ia, Ia, Ib, Ic, Id, Ie, If, Ig, 1h, 1i, 1j, 1k, 1l, 1m and 1n), wherein $R^2$ is optionally substituted phenyl (more preferably unsubstituted phenyl) and $R^1$ is ethyl or propenyl.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is $(C_1-C_9)$heterocyclyl, more preferably $(C_3-C_5)$heterocyclyl, more preferably wherein said heterocyclyl is azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, tetrahydropyranyl, oxazinyl, oxathiazinyl, indolinyl, isoindolinyl, quinuclidinyl, chromanyl, isochromanyl, benzoxazinyl, more preferably wherein said heterocyclyl is attached other than through nitrogen, more preferably tetrahydrofuranyl, pyrrolidinyl, piperidinyl, piperazinyl, oxetanyl, tetrahydropyranyl, and morpholinyl (optionally substituted with one to three, more preferably one to two, more preferably one, substituent independently selected from halo, $CF_3$ or $(C_1-C_6)$alkyl), more preferably wherein said heterocyclyl is tetrahydrofuranyl, oxetanyl and tetrahydropyranyl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^2$ is optionally substituted heterocyclyl and $R^1$ is ethyl or propenyl (more preferably wherein said heterocyclyl is tetrahydrofuranyl, oxetanyl and tetrahydropyranyl, more preferably wherein said heterocyclyl is tetrahydrofuran-2-yl, oxetan-2-yl and tetrahydropyran-2-yl, more preferably wherein said heterocyclyl is unsubstituted tetrahydrofuranyl, oxetanyl and tetrahydropyranyl).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is $(C_3-C_6)$alkynyl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^2$ is optionally substituted $(C_3-C_6)$alkynyl and $R^1$ is ethyl or propenyl.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^2$ is $(C_2-C_6)$alkenyl. Another embodiment of the present invention are those compounds of formula Ia, Ib, Ic, Id, Ie, If, Ig, 1h, 1i, 1j, 1k, 1l, 1m and 1n), wherein $R^2$ is optionally substituted $(C_2-C_6)$alkenyl and $R^1$ is ethyl or propenyl.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is hydrogen. Another embodiment of the invention relates to compounds of formula I (and compounds of the formula Ia, Ib, Ic, Id, Ie, If, Ig, 1h, 1i, 1j, 1k, 1l, 1m and In) wherein $R^3$ is hydrogen in combination with each of aforementioned $R^2$ and $R^1$ embodiments.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is $(C_1-C_6)$alkyl, more preferably methyl, ethyl or propyl more preferably methyl, optionally substituted with 1–3 substituents, more preferably 1–2 substituents, more preferably a substituent, independently selected from halo or hydroxy (most preferably unsubstituted methyl).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is optionally substituted $(C_6-C_{10})$aryl, more preferably phenyl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^3$ is optionally substituted aryl, more preferably phenyl, in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is $(C_3-C_5)$heteroaryl, more preferably wherein said heteroaryl is thiazolyl, pyridyl or oxazolyl, more preferably wherein said heteroaryl is thiazol-2-yl, pyrid-2-yl or oxazol-2-yl (optionally substituted with one to three, more preferably one to two, more preferably one, substituent independently selected from halo, $CF_3$ or $(C_1-C_6)$alkyl), more preferably wherein said heteroaryl is unsubstituted thiazol-2-yl, pyrid-2-yl or oxazol-2-yl, more preferably thiazol-2-yl or pyrid-2-yl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^3$ is optionally substituted heteroaryl (more preferably wherein said heteroaryl is thiazolyl, pyridyl or oxazolyl, more preferably wherein said heteroaryl is thiazol-2-yl, pyrid-2-yl or oxazol-2-yl, more preferably wherein said heteroaryl is unsubstituted thiazol-2-yl, pyrid-2-yl or oxazol-2-yl) in combination with each of the aforementioned embodiments of $R^1$ (e.g., ethyl or propenyl) and $R^2$ (e.g., the $R^2$ aryls, heteroaryls, heterocyclyls, alkynyls, alkenyls and/or alkyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is $(C_1-C_9)$heterocyclyl, more preferably $(C_3-C_5)$heterocyclyl, more preferably wherein said heterocyclyl is azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, tetrahydropyranyl, oxazinyl, oxathiazinyl, indolinyl, isoindolinyl, quinuclidinyl, chromanyl, isochromanyl, benzoxazinyl, more preferably wherein said heterocyclyl is attached other than through nitrogen, more preferably tetrahydrofuranyl, pyrrolidinyl, piperidinyl, piperazinyl, oxetanyl, tetrahydropyranyl, and morpholinyl (optionally substituted with one to three, more preferably one to two, more preferably one, substituent independently selected from halo, $CF_3$ or $(C_1-C_6)$alkyl), more preferably wherein said heterocyclyl is tetrahydrofuranyl, oxetanyl and tetrahydropyranyl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^3$ is optionally substituted heterocyclyl (more preferably wherein said heterocyclyl is tetrahydrofuranyl, oxetanyl and tetrahydropyranyl, more preferably wherein said heterocyclyl is tetrahydrofuran-2-yl, oxetan-2-yl and tetrahydropyran-2-yl, more preferably wherein said heterocyclyl is unsubstituted tetrahydrofuranyl, oxetanyl and tetrahydropyranyl) in combination with each of the aforementioned embodiments of $R^1$ (e.g., ethyl or propenyl) and $R^2$ (e.g., the $R^2$ aryls, heteroaryls, heterocyclyls, alkynyls, alkenyls and/or alkyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^3$ is optionally substituted phenyl, more preferably unsubstituted phenyl. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^3$ is optionally substituted phenyl (more preferably unsubstituted phenyl) in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^4$ is —OH. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^4$ is hydroxy in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^4$ is $R^{14}R^{15}N$—. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^4$ is $R^{14}R^{15}N$— in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is —OH. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is hydroxy in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is $(C_1-C_6)$alkyl-O—, $(C_3-C_{10})$cycloalkyl-O—, $(C_6-C_{10})$aryl-O—, $(C_1-C_9)$heteroaryl-O—, or $(C_1-C_9)$heterocyclic-O—, wherein each of said $(C_1-C_6)$alkyl, $(C_3-C_{10})$cycloalkyl, $(C_6-C_{10})$aryl, $(C_1-C_9)$heteroaryl, $(C_1-C_9)$heterocyclic moieties of said $(C_1-C_6)$alkyl-O—, $(C_3-C_{10})$cycloalkyl-O—, $(C_6-C_{10})$aryl-O—, $(C_1-C_9)$heteroaryl-O—, $(C_1-C_9)$heterocyclic-O— radicals may optionally be substituted with one to three substituents (more preferably one to two substituents, more preferably one substituent) independently selected from $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl, $(C_1-C_9)$heterocyclic, halo, HO—, HO—(C=O)—, $R^{21}$—(C=O)—, $R^{22}$—CO$_2$—, N≡C—, $R^{23}R^{24}N$—, $R^{23}R^{24}N$—(C=O)—, $R^{21}(C=O)$—NH—, $R^{21}(C=O)$—N[$(C_1-C_6)$alkyl]-. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is optionally substituted $(C_1-C_6)$alkyl-O—, $(C_3-C_{10})$cycloalkyl-O—, $(C_6-C_{10})$aryl-O—, $(C_1-C_9)$heteroaryl-O—, or $(C_1-C_9)$heterocyclic-O—, in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is optionally substituted $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl or $(C_1-C_9)$heterocyclic-$(C_1-C_6)$alkyl; optionally substituted with one to three substituents independently selected from $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl, $(C_1-C_9)$heterocyclic, halo, HO—, HO—(C=O)—, $R^{21}$—(C=O)—, $R^{22}$—CO$_2$—, N≡C—, $R^{23}R^{24}N$—, $R^{23}R^{24}N$—(C=O)—, $R^{21}(C=O)$—NH—, $R^{21}(C=O)$—[N—$(C_1-C_6)$alkyl]-. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is optionally substituted $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl or $(C_1-C_9)$heterocyclic-$(C_1-C_6)$alkyl, in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is $(C_6-C_{10})$aryl-$(C_1-C_6)$alkyl-O—, $(C_1-C_9)$heteroaryl-$(C_1-C_6)$alkyl-O—, $(C_1-C_9)$heterocyclic-$(C_1-C_6)$alkyl-O—, wherein each of said $(C_6-C_{10})$aryl, $(C_1-C_9)$heteroaryl, $(C_1-C_9)$heterocyclic moieties of said $(C_6-C_{10})$aryl-$(C_1-C_6)$alkyl-O—, $(C_1-C_9)$heteroaryl-$(C_1-C_6)$alkyl-O—, and $(C_1-C_9)$heterocyclic-$(C_1-C_6)$alkyl-O— (more preferably $(C_1-C_9)$heteroaryl-$(C_1-C_6)$alkyl-O—), may optionally be substituted with one to three substituents (more preferably one to two substituents, more preferably one substituent) independently selected from the group consisting of $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl(CH$_2$)$_n$—, $(C_1-C_9)$heterocyclic, halo, HO—, HO—(C=O)—, $R^{20}$—O—(C=O)—, $R^{21}$—(C=O)—, $R^{22}$—CO$_2$—, N≡C—, $R^{23}R^{24}N$—, $R^{23}R^{24}N$—$(C_1-C_6)$alkyl-, $R^{23}R^{24}N$—(C=O)—, $R^{21}$(C=O)—NH—, $R^{21}(C=O)$—[N—$(C_1-C_6)$alkyl]-; $R^{21}(C=O)$—NH—$(C_1-C_6)$alkyl-; and $R^{21}(C=O)$—[N—$(C_1-C_6)$alkyl]-$(C_1-C_6)$alkyl-; wherein said $(C_3-C_{10})$cycloalkyl, $(C_6-C_{10})$aryl, $(C_1-C_9)$heteroaryl(CH$_2$)$_n$—, $(C_1-C_9)$heterocyclic substituents may optionally be substituted on a ring carbon or nitrogen by one to three members (more preferably one to two members, more preferably one member) per ring independently selected from halo, $(C_1-C_6)$alkyl, and $(C_1-C_6)$alkoxy. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is optionally substituted ($C_6$-$C_{10}$)aryl-($C_1$-$C_6$)alkyl-O—, ($C_1$-$C_9$)heteroaryl-($C_1$-$C_6$)alkyl-O—, ($C_1$-$C_9$)heterocyclic-($C_1$-$C_6$)alkyl-O— (more preferably ($C_1$-$C_9$)heteroaryl-($C_1$-$C_6$)alkyl-O—), in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

A more preferred embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is ($C_1$-$C_9$)heteroaryl-($C_1$-$C_6$)alkyl-O— optionally substituted with one to two substituents independently selected from the group consisting of ($C_1$-$C_6$)alkyl, ($C_6$-$C_{10}$)aryl, ($C_1$-$C_9$)heteroaryl($CH_2$)$_n$—, halo, HO—, HO—(C=O)—, $R^{20}$—O—(C=O)—, $R^{21}$—(C=O)—, $R^{22}$—$CO_2$—, N≡C—, $R^{23}R^{24}$N—, $R^{23}R^{24}$N—($C_1$-$C_6$)alkyl-, $R^{23}R^{24}$N—(C=O)—, $R^{21}$(C=O)—NH—, $R^{21}$(C=O)—[N—($C_1$-$C_6$)alkyl]-; $R^{21}$(C=O)—NH—($C_1$-$C_6$)alkyl-; and $R^{21}$(C=O)—[N—($C_1$-$C_6$)alkyl]-($C_1$-$C_6$)alkyl-; wherein said ($C_3$-$C_{10}$)cycloalkyl, ($C_6$-$C_{10}$)aryl, ($C_1$-$C_9$)heteroaryl($CH_2$)$_n$—, ($C_1$-$C_9$)heterocyclic substituents may optionally be substituted on a ring carbon or nitrogen by one to two members per ring independently selected from halo, ($C_1$-$C_6$)alkyl, and ($C_1$-$C_6$)alkoxy;

wherein n is an integer from zero to two;

wherein each of $R^{23}$ and $R^{24}$ is independently selected from hydrogen, ($C_1$-$C_6$)alkyl, ($C_6$-$C_{10}$)aryl, ($C_1$-$C_9$)heteroaryl, ($C_1$-$C_9$)heterocyclic, ($C_1$-$C_9$)heteroaryl($C_1$-$C_6$)alkyl, ($C_6$-$C_{10}$)aryl($C_1$-$C_6$)alkyl, ($C_1$-$C_9$)heterocyclic($C_1$-$C_6$)alkyl, HO—($C_1$-$C_6$)alkyl, amino-($C_1$-$C_6$)alkyl-, ($C_1$-$C_6$)alkylamino-($C_1$-$C_6$)alkyl-, and [($C_1$-$C_6$)alkyl]$_2$amino-($C_1$-$C_6$)alkyl-; wherein said each of said ($C_6$-$C_{10}$)aryl, ($C_1$-$C_9$)heteroaryl, and ($C_1$-$C_9$)heterocyclic moieties of said ($C_6$-$C_{10}$)aryl-, ($C_1$-$C_9$)heteroaryl-, ($C_1$-$C_9$)heterocyclic-, ($C_6$-$C_{10}$)aryl-($C_1$-$C_6$)alkyl, ($C_1$-$C_9$)heteroaryl-($C_1$-$C_6$)alkyl and ($C_1$-$C_9$)heterocyclic-($C_1$-$C_6$)alkyl, may optionally be substituted with one to two substituents independently selected from the group consisting of halo, ($C_1$-$C_6$)alkyl or ($C_1$-$C_6$)alkoxy, or $R^{23}$ and $R^{24}$ are taken together to form an azetidinyl, pyrrolidinyl, piperidinyl, piperazinyl, ($C_1$-$C_6$)alkyl-piperazinyl or morpholinyl ring.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is optionally substituted ($C_1$-$C_6$)alkyl-O—, optionally substituted with one to three substituents independently selected from the group consisting of ($C_3$-$C_{10}$)cycloalkyl, ($C_6$-$C_{10}$)aryl, ($C_1$-$C_9$)heteroaryl and ($C_1$-$C_9$)heterocyclic; wherein said ($C_3$-$C_{10}$)cycloalkyl, ($C_6$-$C_{10}$)aryl, ($C_1$-$C_9$)heteroaryl ($CH_2$)$_n$—, ($C_1$-$C_9$)heterocyclic substituents may optionally be substituted on a ring carbon or nitrogen by one to three members per ring independently selected from halo, ($C_1$-$C_6$)alkyl, and ($C_1$-$C_6$)alkoxy. Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is optionally substituted ($C_1$-$C_6$)alkyl-O— in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is ($C_1$-$C_6$)alkyl-O— substituted with one substituent selected from the group consisting of halo, HO—, HO—(C=O)—, $R^{20}$—O—(C=O)—, $R^{21}$—(C=O)—, $R^{22}$—$CO_2$—, N≡C—, $R^{23}R^{24}$N—, $R^{23}R^{24}$N—(C=O)—, $R^{21}$(C=O)—NH—, and $R^{21}$(C=O)—[N—($C_1$-$C_6$)alkyl]-; wherein $R^{23}$ and $R^{24}$ is independently selected from hydrogen, ($C_1$-$C_6$)alkyl, ($C_6$-$C_{10}$)aryl, ($C_1$-$C_9$)heteroaryl, ($C_1$-$C_9$)heterocyclic, ($C_1$-$C_9$)heteroaryl($C_1$-$C_6$)alkyl, ($C_6$-$C_{10}$)aryl($C_1$-$C_6$)alkyl, ($C_1$-$C_9$)heterocyclic($C_1$-$C_6$)alkyl, HO—($C_1$-$C_6$)alkyl, N≡C—($C_1$-$C_6$)alkyl, amino-($C_1$-$C_6$)alkyl-, ($C_1$-$C_6$)alkylamino-($C_1$-$C_6$)alkyl-, and [($C_1$-$C_6$)alkyl]$_2$amino-($C_1$-$C_6$)alkyl-; wherein said each of said ($C_6$-$C_{10}$)aryl, ($C_1$-$C_9$)heteroaryl, and ($C_1$-$C_9$)heterocyclic moieties of said ($C_6$-$C_{10}$)aryl-, ($C_1$-$C_9$)heteroaryl-, ($C_1$-$C_9$)heterocyclic-, ($C_6$-$C_{10}$)aryl-($C_1$-$C_6$)alkyl, ($C_1$-$C_9$)heteroaryl-($C_1$-$C_6$)alkyl and ($C_1$-$C_9$)heterocyclic-($C_1$-$C_6$)alkyl, may optionally be substituted with one to two substituents independently selected from the group consisting of halo, ($C_1$-$C_6$)alkyl or ($C_1$-$C_6$)alkoxy, or $R^{23}$ and $R^{24}$ are taken together to form an azetidinyl, pyrrolidinyl, piperidinyl or morpholinyl ring.

Another embodiment of the present invention relates to compounds of formula I, (and compounds of the formula Ia, Ib, Ic, Id, Ie, If, Ig, 1h, 1i, 1j, 1k, 1l, 1m and 1n), wherein $R^5$ is —C≡N, $R^{16}R^{17}$N—(C=O)—, $R^{16}R^{17}$—N—$SO_2$—, $R^{18}$—$SO_2$—, $R^{18}$—$SO_2$—(N—$R^{19}$)—, $R^{18}$—$SO_3$—, $R^{16}$(C=O)—($R^{25}$—N)—, $R^{16}R^{17}$N—(C=O)—($R^{25}$—N)—, $R^{19}$—O—(C=O)—($R^{25}$—N)—, $R^{18}$—(C=O)—O—, $R^{18}$—(C=O)—, $R^{16}R^{17}$N—(C=O)—O— or $R^{19}$—O—(C=O)—, more preferably $R^{16}R^{17}$N—(C=O)—.

Another embodiment of the present invention are those compounds of formula I, (and compounds of the formula Ia, Ib, Ic, Id, Ie, If, Ig, 1h, 1i, 1j, 1k, 1l, 1m and 1n), wherein $R^5$ is $R^{16}R^{17}$N—(C=O)—, $R^{16}R^{17}$N—$SO_2$—, $R^{18}$—$SO_2$—, $R^{18}$—$SO_2$—(N$R^{19}$)—, $R^{18}$—$SO_3$—, $R^{16}$—(C=O)—($R^{25}$—N)—, $R^{16}R^{17}$N—(C=O)—($R^{25}$—N)—, $R^{19}$—O—(C=O)—($R^{25}$—N)—, $R^{18}$—(C=O)—O—, $R^{18}$—(C=O)—, $R^{16}R^{17}$N—(C=O)—O— or $R^{19}$—O—(C=O)—, more preferably $R^{16}R^{17}$N—(C=O)—, in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos).

Another embodiment of the present invention are those compounds of formula I, (and compounds of the formula Ia, Ib, Ic, Id, Ie, If, Ig, 1h, 1i, 1j, 1k, 1l, 1m and 1n), wherein X and Y are each hydrogen. Another embodiment of the present invention are those compounds of formula I, (and compounds of the formula Ia, Ib, Ic, Id, Ie, If, Ig, 1h, 1i, 1j, 1k, 1l, 1m and 1n), wherein X and Y are each hydrogen in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos) and/or $R^5$ (e.g., oxys (e.g., alkoxy, cycloalkyloxy aryloxy, heteroaryloxy or heterocyclyloxy), cyclyls (e.g., aryl, heteroaryl, heterocyclyl), cyclyl-alkoxys (e.g., heteroaryl-alkoxy) and/or heteroatom linked (e.g., $R^{16}R^{17}$N—(C=O)—, $R^{16}R^{17}$N—$SO_2$—, $R^{18}$—$SO_2$—, $R^{18}$—$SO_2$—(N$R^{19}$)—, $R^{18}$—$SO_3$—, $R^{16}$—(C=O)—($R^{25}$—N)—, $R^{16}R^{17}$N—(C=O)—($R^{25}$—N)—, $R^{19}$—O—(C=O)—($R^{25}$—N)—, $R^{18}$—(C=O)—O—, $R^{18}$—(C=O)—, $R^{16}R^{17}$N—(C=O)—O— or $R^{19}$—O—(C=O)—).

Another embodiment of the present invention are those compounds of formula I, (and compounds of the formula Ia, Ib, Ic, Id, Ie, If, Ig, 1h, 1i, 1j, 1k, 1l, 1m and 1n), wherein one of X and Y is fluoro, chloro, or bromo. Another embodiment of the present invention are those compounds of formula I, (and compounds of the formula Ia, Ib, Ic, Id, Ie, If, Ig, 1h, 1i, 1j, 1k, 1l, 1m and 1n), wherein one of X and Y is fluoro, chloro, or bromo in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos) and/or $R^5$ (e.g., oxys (e.g., alkoxy, cycloalkyloxy aryloxy, heteroaryloxy or heterocyclyloxy), cyclyls (e.g., aryl, heteroaryl, heterocyclyl), cyclyl-alkoxys (e.g., heteroaryl-alkoxy) and/or heteroatom linked (e.g., $R^{16}R^{17}N—(C=O)—$, $R^{16}R^{17}N—SO_2—$, $R^{18}—SO_2—$, $R^{18}—SO_2—(NR^{19})—$, $R^{18}—SO_3$, $R^{16}—(C=O)—(R^{25}—N)—$, $R^{16}R^{17}N—(C=O)—(R^{25}—N)—$, $R^{19}—O—(C=O)—(R^{25}—N)—$, $R^{18}—(C=O)—O—$ $R^{18}—(C=O)—$, $R^{16}R^{17}N—(C=O)—O—$ or $R^{19}—O—(C=O)—$).

Another embodiment of the present invention are those compounds of formula I, (and compounds of the formula Ia, Ib, Ic, Id, Ie, If, Ig, 1h, 1i, 1j, 1k, 1l, 1m and 1n), wherein each of X and Y are independently selected from fluoro, chloro, and bromo. Another embodiment of the present invention are those compounds of formula I, (and compounds of the formula Ia, Ib, Ic, Id, Ie, If, Ig, 1h, 1i, 1j, 1k, 1l, 1m and 1n), wherein each of X and Y are independently selected from fluoro, chloro, and bromo in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos) and/or $R^5$ (e.g., oxys (e.g., alkoxy, cycloalkyloxy aryloxy, heteroaryloxy or heterocyclyloxy), cyclyls (e.g., aryl, heteroaryl, heterocyclyl), cyclyl-alkoxys (e.g., heteroaryl-alkoxy) and/or heteroatom linked (e.g., $R^{16}R^{17}N—(C=O)—$, $R^{16}R^{17}N—SO_2—$, $R^{18}—SO_2—$, $R^{18}—SO_2—(NR^{19})—$, $R^{18}—SO_3—$, $R^{16}—(C=O)—(R^{25}—N)—$, $R^{16}R^{17}N—(C=O)—(R^{25}—N)—$, $R^{19}—O—(C=O)—(R^{25}—N)—$, $R^{18}—(C=O)—O—$, $R^{18}—(C=O)—$, $R^{16}R^{17}N—(C=O)—O—$ or $R^{19}—O—(C=O)—$)).

Another embodiment of the present invention are those compounds of formula I, (and compounds of the formula Ia, Ib, Ic, Id, Ie, If, Ig, 1h, 1i, 1j, 1k, 1l, 1m and 1n), wherein one of X and Y is $(C_1–C_6)$alkyl. Another embodiment of the present invention are those compounds of formula I, (and compounds of the formula Ia, Ib, Ic, Id, Ie, If, Ig, 1h, 1i, 1j, 1k, 1l, 1m and 1n), wherein one of X and Y is $(C_1–C_6)$alkyl in combination with each of the aforementioned embodiments of $R^1$ (e.g., ethyl or propenyl) and/or $R^2$ (e.g., the $R^2$ aryls, heteroaryls, heterocyclyls, alkynyls, alkenyls and alkyls) and/or $R^3$ (e.g., the $R^3$ hydrogens, alkyls, alkenyls, alkynyls, aryls, heteroaryls, and heterocyclyls) and/or $R^4$ (hydroxys or aminos) and/or $R^5$ (e.g., oxys (e.g., alkoxy, cycloalkyloxy aryloxy, heteroaryloxy or heterocyclyloxy), cyclyls (e.g., aryl, heteroaryl, heterocyclyl), cyclyl-alkoxys (e.g., heteroaryl-alkoxy) and/or heteroatom linked (e.g., $R^{16}R^{17}N—(C=O)—$, $R^{16}R^{17}N—SO_2—$, $R^{18}—SO_2—$, $R^{18}—SO_2—(NR^{19})—$, $R^{18}—SO_3—$, $R^{16}—(C=O)—(R^{25}—N)—$, $R^{16}R^{17}N—(C=O)—(R^{25}—N)—$, $R^{19}—O—(C=O)—(R^{25}—N)—$, $R^{18}—(C=O)—O—$, $R^{18}—(C=O)—$, $R^{16}R^{17}N—(C=O)—O—$ or $R^{19}—O—(C=O)—$)).

Specific preferred compounds of the invention include:
(2R,3S,4aR,10aR)-4a-Ethyl-2-prop-1-ynyl-1,2,3,4,4a,9,10,10a-octahydrophenanthrene-2,3,7-triol;

(2R,3S,4aR,10aR)-4a-Ethyl-7-(2-methylpyridin-3-ylmethoxy)-2-prop-1-ynyl-1,2,3,4,4a,9,10,10a-octahydrophenanthrene-2,3-diol;

(2R,3R,4aR,10aR)-7-[5-(2-Dimethylaminoethyl)-[1,2,4]oxadiazol-3-ylmethoxy]-4a-ethyl-3-methyl-2-phenyl-1,2,3,4,4a,9,10,10a-octahydrophenanthrene-2,3-diol;

(2R,3R,4aR,10aR)-4a-Ethyl-3-methyl-2-pyridin-2-yl-1,2,3,4,4a,9,10,10a-octahydrophenanthrene-2,3,7-triol;

(2R,3R,4aR,10aR)-4a-Ethyl-3-methyl-7-(2-methylpyridin-3-ylmethoxy)-2-pyridin-2-yl-1,2,3,4,4a,9,10,10a-octahydrophenanthrene-2,3-diol;

(2R,3S,4aR,10aR)-4a-Ethyl-3-methyl-2-thiazol-2-yl-1,2,3,4,4a,9,10,10a-octahydrophenanthrene-2,3,7-triol;

(2R,3S,4aR,10aR)-4a-Ethyl-3-methyl-2-(4-methylthiazol-2-yl)-1,2,3,4,4a,9,10,10a-octahydrophenanthrene-2,3,7-triol;

(2R,3R,4aR,10aS)-4a-Ethyl-2,3,7-trihydroxy-3-methyl-2-phenyl-2,3,4,4a,10,10a-hexahydro-1H-phenanthren-9-one;

(2R,3R,4aR,10aS)-4a-Ethyl-3,9-dimethyl-2-phenyl-1,2,3,4,4a,10a-hexahydro-phenanthrene-2,3,7-triol;

(2R,3R,4aR,10aR)-3,4a-Diethyl-2-phenyl-1,2,3,4,4a,9,10,10a-octahydrophenanthrene-2,3,7-triol;

(2R,3R,4aR,10aR)-4a-Ethyl-7-(2-hydroxy-ethoxy)-3-methyl-2-phenyl-1,2,3,4,4a,9,10,10a-octahydro-phenanthrene-2,3-diol;

(2R,3R,4aR,10aR)-4a-Ethyl-7-(3-hydroxy-propoxy)-3-methyl-2-phenyl-1,2,3,4,4a,9,10,10a-octahydro-phenanthrene-2,3-diol;

(2R,3R,4aR,10aR)-4a-Ethyl-7-(4-hydroxy-butoxy)-3-methyl-2-phenyl-1,2,3,4,4a,9,10,10a-octahydro-phenanthrene-2,3-diol;

(4bR,7R,6R,8aR)-4-(4b-Ethyl-6,7-dihydroxy-6-methyl-7-phenyl-4b,5,6,7,8,8a9,10-octahydro-phenanthren-2-yloxy)-butyronitrile;

(4bR,7R,6R,8aR)-5-(4b-Ethyl-6,7-dihydroxy-6-methyl-7-phenyl-4b,5,6,7,8,8a9,10-octahydro-phenanthren-2-yloxy)-pentanenitrile;

(4bR,7R,6R,8aR)-2-(4b-Ethyl-6,7-dihydroxy-6-methyl-7-phenyl-4b,5,6,7,8,8a9,10-octahydro-phenanthren-2-yloxy)-acetamide;

(2R,3R,4aR,10aR)-4a-Ethyl-7-(4-hydroxy-4-methyl-pentyloxy)-3-methyl-2-phenyl-1,2,3,4,4a,9,10,10a-octahydrophenanthrene-2,3-diol;

(2R,3R,4aR,10aR)-4a-Ethyl-7-(5-hydroxy-5-methyl-hexyloxy)-3-methyl-2-phenyl-1,2,3,4,4a,9,10,10a-octahydro-phenanthrene-2,3-diol;

(2R,3R,4aR,10aR)-4a-Ethyl-3-methyl-2-prop-1-ynyl-1,2,3,4,4a,9,10,10a-octahydro-phenanthrene-2,3,7-triol;

(2R,3R,4aR,10aR)-4a-Ethyl-3-methyl-2-p-tolyl-1,2,3,4,4a,9,10,10a-octahydro-phenanthren-2,3,7-triol; and (2R,3R,4aR,10aR)-4a-Ethyl-3-methyl-2-propenyl-1,2,3,4,4a,9,10,10a-octahydro-phenanthrene-2,3,7-triol.

Other compounds of the invention include:
(4bR,6R,7R,8aR)-4b-Ethyl-6,7-dihydroxy-6-methyl-7-phenyl-4b,5,6,7,8,8a,9,10-octahydrophenanthrene-2-carboxylic acid methylamide;

(4bR,6R,7R,8aR)-4b-Ethyl-6,7-dihydroxy-6-methyl-7-pyridin-2-yl-4b,5,6,7,8,8a,9,10-octahydrophenanthrene-2-carboxylic acid methylamide;

(4bR,6R,7R,8aR)-4b-Ethyl-6,7-dihydroxy-6-methyl-7-pyridin-2-yl-4b,5,6,7,8,8a,9,10-octahydrophenanthrene-2-carboxylic acid (pyridin-4-ylmethyl)amide;

(4bR,6R,7R,8aR)-4b-Ethyl-6,7-dihydroxy-6-methyl-7-pyridin-2-yl-4b,5,6,7,8,8a,9,10-octahydro-phenanthrene-2-carboxylic acid (2-methyl-pyridin-3-ylmethyl)amide;

(2R,3R,4aR,10aR)-4a-Ethyl-3-methyl-2-pyridin-2-yl-7-(2H-[1,2,4]triazol-3-yl)-1,2,3,4,4a,9,10,10a-octahydro-phenanthrene-2,3-diol;

(2R,3R,4aR,10aR)-4a-Ethyl-3-methyl-2-pyridin-2-yl-7-(pyrimidin-2-yloxy)-1,2,3,4,4a,9,10,10a-octahydrophenanthrene-2,3-diol;

(2R,3R,4aR,10aR)-4a-Ethyl-3-methyl-2-pyridin-2-yl-7-(pyridin-4-yloxy)-1,2,3,4,4a,9,10,10a-octahydrophenanthrene-2,3-diol;

(4bR,6R,7R,8aR)-(2-Pyrrolidin-1-ylethyl)carbamic acid 4b-ethyl-6,7-dihydroxy-6-methyl-7-pyridin-2-yl-4b,5,6,7,8,8a,9,10-octahydrophenanthren-2-yl ester;

(4bR,6R,7R,8aR)-(2-Dimethylaminoethyl)carbamic acid 4b-ethyl-6,7-dihydroxy-6-methyl-7-pyridin-2-yl-4b,5,6,7,8,8a,9,10-octahydrophenanthren-2-yl ester;

(4bR,6R,7R,8aR)-4b-Ethyl-6,7-dihydroxy-6-methyl-7-pyridin-2-yl-4b,5,6,7,8,8a,9,10-octahydro-phenanthrene-2-carboxylic acid (2-dimethylaminoethyl)amide;

(4bR,6R,7R,8aR)-(2-Dimethylaminoethyl)methylcarbamic acid 4b-ethyl-6,7-dihydroxy-6-methyl-7-pyridin-2-yl-4b,5,6,7,8,8a,9,10-octahydrophenanthren-2-yl ester;

(4bR,6R,7R,8aR)-Methyl-(2-morpholin-4-yl-ethyl)carbamic acid 4b-ethyl-6,7-dihydroxy-6-methyl-7-pyridin-2-yl-4b,5,6,7,8,8a,9,10-octahydrophenanthren-2-yl ester;

(4bR,6R,7R,8aR)-4b-Ethyl-6,7-dihydroxy-6-methyl-7-pyridin-2-yl-4b,5,6,7,8,8a,9,10-octahydro-phenanthrene-2-carboxylic acid methyl ester;

(4bR,6R,7R,8aR)-4b-Allyl-6,7-dihydroxy-6-methyl-7-pyridin-2-yl-4b,5,6,7,8,8a,9,10-octahydro-phenanthrene-2-carboxylic acid methyl ester;

(4bR,6R,7R,8aR)-4b-Allyl-6,7-dihydroxy-6-methyl-7-oxazol-2-yl-4b,5,6,7,8,8a,9,10-octahydro-phenanthrene-2-carboxylic acid methyl ester;

(2R,3R,4aR,10aR)-4a-Ethyl-3-methyl-2-oxazol-2-yl-1,2,3,4,4a,9,10,10a-octahydrophenanthrene-2,3,7-triol;

(2R,3R,4aR,10aR)-4a-Ethyl-3-methyl-7-(2-methylpyridin-3-ylmethoxy)-2-oxazol-2-yl-1,2,3,4,4a,9,10,10a-octahydrophenanthrene-2,3-diol;

(2R,3R,4aR,10aR)-4a-Ethyl-2-isoxazol-5-yl-3-methyl-7-(2-methylpyridin-3-ylmethoxy)-1,2,3,4,4a,9,10,10a-octahydrophenanthrene-2,3-diol;

(2R,3R,4aR,10aS)-4a-Ethyl-3-methyl-2-phenyl-1,2,3,4,4a,10a-hexahydro-phenanthrene-2,3,7-triol;

(2R,3R,4aR,10aS)-4a-Ethyl-9-fluoro-3-methyl-2-phenyl-1,2,3,4,4a,10a-hexahydro-phenanthrene-2,3,7-triol;

(2R,3R,4aR,10aS)-4a-Ethyl-3-methyl-2-phenyl-9-trifluoromethyl-1,2,3,4,4a,10a-hexahydro-phenanthrene-2,3,7-triol;

(2R,3R,4aR,10aR)-4a-Ethyl-9-hydroxymethyl-3-methyl-2-phenyl-1,2,3,4,4a,10a-hexahydro-phenanthrene-2,3,7-triol;

(2R,3R,4aR,10aR)-4a-Ethyl-3,9,9-trimethyl-2-phenyl-1,2,3,4,4a,9,10,10a-octahydro-phenanthrene-2,3,7-triol;

(2R,3R,4aR,10aR)-4a-Ethyl-3-methyl-2-phenyl-9-9-spirocyclopropane-1,2,3,4,4a,9,10,10a-octahydro-phenanthrene-2,3,7-triol;

(3R,4R,5aR,9bS)-5a-Ethyl-4-methyl-3-phenyl-1a,1b,2,3,4,5,5a,9b-octahydro-1H-cyclopropa[l]phenanthrene-3,4,8-triol;

(3R,4R,5aR,9bS)-5a-Ethyl-4,9b-dimethyl-3-phenyl-1a,1b,2,3,4,5,5a,9b-octahydro-1H-cyclopropa[l]phenanthrene-3,4,8-triol;

(2R,3R,4aR,10aR)-8-Bromo-4a-ethyl-3-methyl-2-phenyl-1,2,3,4,4a,9,10,10a-octahydro-phenanthrene-2,3,7-triol;

(2R,3R,4aR,10aR)-6,8-Dibromo-4a-ethyl-3-methyl-2-phenyl-1,2,3,4,4a,9,10,10a-octahydro-phenanthrene-2,3,7-triol;

(2R,3R,4aR,10aR)-6-Chloro-4a-ethyl-3-methyl-2-phenyl-1,2,3,4,4a,9,10,10a-octahydro-phenanthrene-2,3,7-triol;

(2R,3R,4aR,10aR)-8-Bromo-6-chloro-4a-ethyl-3-methyl-2-phenyl-1,2,3,4,4a,9,10,10a-octahydro-phenanthrene-2,3,7-triol;

(2R,3R,4aR,10aR)-8-Bromo-5,6-dichloro-4a-ethyl-3-methyl-2-phenyl-1,2,3,4,4a,9,10,10a-octahydro-phenanthrene-2,3,7-triol;

(2R,3R,4aR,9RS,10aR)-4a-Ethyl-3,9-dimethyl-2-phenyl-1,2,3,4,4a,9,10,10a-octahydro-phenanthrene-2,3,7-triol;

(2R,3R,4aR,10RS,10aS)-4a-Ethyl-3,10-dimethyl-2-phenyl-1,2,3,4,4a,9,10,10a-octahydro-phenanthrene-2,3,7-triol;

(2R,3R,4aR,9RS,10RS,10aS)-4a-Ethyl-3,9,10-trimethyl-2-phenyl-1,2,3,4,4a,9,10,10a-octahydro-phenanthrene-2,3,7-triol;

(2R,3R,4aR,10aR)-4a-Ethyl-3-methyl-2-phenyl-1,2,3,4,4a,9,10,10a-octahydro-phenanthrene-2,3,6,7-tetraol;

(4bR,6R,7R,8aR)-4b-Ethyl-6-methyl-7-phenyl-4b,5,6,7,8,8a,9,10-octahydro-phenanthrene-1,2,3,6,7-pentaol;

(4bR,6R,7R,8aR)-4b-Ethyl-6-methyl-7-phenyl-4b,5,6,7,8,8a,9,10-octahydro-phenanthrene-1,2,6,7-tetraol;

(2R,3R,4aR,10RS,10aS)-4a-Ethyl-2,3,7-trihydroxy-3,10-dimethyl-2-phenyl-2,3,4,4a,10,10a-hexahydro-1H-phenanthren-9-one;

(2R,3R,4aR,10aS)-4a-Ethyl-2,3,7-trihydroxy-3,10,10-trimethyl-2-phenyl-2,3,4,4a,10,10a-hexahydro-1H-phenanthren-9-one;

(2R,3S,4aR,10aR)-3-Aminomethyl-4a-ethyl-2-phenyl-1,2,3,4,4a,9,10,10a-octahydro-phenanthrene-2,3,7-triol;

(2R,3S,4aR,10aR)-4a-Ethyl-3-methylaminomethyl-2-phenyl-1,2,3,4,4a,9,10,10a-octahydro-phenanthrene-2,3,7-triol;

(2R,3S,4aR,10aR)-3-Dimethylaminomethyl-4a-ethyl-2-phenyl-1,2,3,4,4a,9,10,10a-octahydro-phenanthrene-2,3,7-triol;

(2R,3S,4aR,10aR)-4a-Ethyl-3-fluoromethyl-2-phenyl-1,2,3,4,4a,9,10,10a-octahydro-phenanthrene-2,3,7-triol;

(2R,3S,4aR,10aR)-4a-Ethyl-3-hydroxymethyl-2-phenyl-1,2,3,4,4a,9,10,10a-octahydro-phenanthrene-2,3,7-triol;

(2R,3R,4aR,10aR)-3-Amino-4a-ethyl-3-methyl-2-phenyl-1,2,3,4,4a,9,10,10a-octahydro-phenanthrene-2,7-diol;

(2R,3R,4aR,10aR)-4a-Ethyl-3,9,9-trimethyl-7-(2-methylpyridin-3-ylmethoxy)-2-pyridin-2-yl-1,2,3,4,4a,9,10,10a-octahydrophenanthrene-2,3-diol;

(2R,3R,4aR,10aR)-4a-Ethyl-3,9,9-trimethyl-7-(2-methylpyridin-3-ylmethoxy)-2-phenyl-1,2,3,4,4a,9,10,10a-octahydrophenanthrene-2,3-diol;

(2R,3R,4aR,10aR)-4a-Ethyl-3,9,9-trimethyl-7-(2-methylpyridin-3-ylmethoxy)-2-thiazol-2-yl-1,2,3,4,4a,9,10,10a-octahydro-phenanthrene-2,3-diol;

(2R,3R,4aR,9R,10aR)-4a-Ethyl-3,9-dimethyl-7-(2-methyl-pyridin-3-ylmethoxy)-2-thiazol-2-yl-1,2,3,4,4a,9,10,10a-octahydro-phenanthrene-2,3-diol;

(2R,3R,4aR,9S,10aR)-4a-Ethyl-3,9-dimethyl-7-(2-methyl-pyridin-3-ylmethoxy)-2-thiazol-2-yl-1,2,3,4,4a,9,10,10a-octahydro-phenanthrene-2,3-diol;

(2R,3R,4aR,10aR)-4a-Ethyl-2,3-dihydroxy-3,10,10-trimethyl-7-(pyridin-4-ylmethoxy)-2-thiazol-2-yl-2,3,4,4a,10,10a-hexahydro-1H-phenanthren-9-one;

(2R,3R,4aR,10aR)-4a-Ethyl-3-methyl-2-(3-methyl-[1,2,4]oxadiazol-5-yl)-7-(2-methylpyridin-3-ylmethoxy)-1,2,3,4,4a,9,10,10a-octahydro-phenanthrene-2,3-diol; and (2R,3R,4aR,10aR)-4a-Ethyl-3-methyl-2-(5-methyl-[1,2,4]oxadiazol-3-yl)-7-(2-methylpyridin-3-ylmethoxy)-1,2,3,4,4a,9,10,10a-octahydro-phenanthrene-2,3-diol.

The compounds of the present invention are glucocorticoid modulators and as such are either GR agonists, partial agonists or antagonists. Thus, the compound of the present invention can be used to influence the basic, life sustaining systems of the body, including carbohydrate, protein and lipid metabolism, electrolyte and water balance, and the functions of the cardiovascular, kidney, central nervous, immune, skeletal muscle and other organ and tissue systems. In this regard, GR modulators are used for the treatment of diseases associated with an excess or a deficiency of glucocorticoids in the body. As such, they may be used to treat the following: obesity, diabetes, gastrointestinal diseases, cardiovascular disease, hypertension, hematologic diseases, neoplastic diseases, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, edematous states, inflammatory diseases (such as osteoarthritis, rheumatoid arthritis, psoriatic arthritis, ankylosing spondylitis, asthma and rhinitis), collagen diseases, tests of adrenal function, viral infection, immunodeficiency, immunomodulation, autoimmune diseases, endocrine disorders, allergies, wound healing, dermatological disorders, ophthalmic diseases, compulsive behavior, multi-drug resistance, addiction, psychosis, anorexia, cachexia, post-traumatic stress syndrome, post-surgical bone fracture, medical catabolism and prevention of muscle frailty.

More specifically, certain compounds of the present invention, isomers, prodrugs and pharmaceutically acceptable salts thereof are useful to induce weight loss in mammals needing or desiring to lose weight. While not intending to limit the present invention to a specific mechanism of action, the compounds of the present invention, isomers, prodrugs and salts thereof are able to induce weight loss by a variety of mechanisms, such as appetite suppression, decreasing food intake, and stimulation of the metabolic rate in peripheral tissue, thereby increasing energy expenditure. In addition, the compounds of the present invention, isomers, prodrugs and salts thereof are useful to induce a more favorable partitioning of nutrients from fat to muscle tissue in mammals. Thus, while not necessarily resulting in weight loss, this increase in muscle mass may be useful in preventing or treating diseases, such as obesity and frailty.

In addition, certain compounds of the present invention, isomers, prodrugs and pharmaceutically acceptable salts thereof may also be useful to increase lean meat deposition, improve lean meat to fat ratio, and trim unwanted fat from non-human animals, as described further below.

Another more specific embodiment of the present invention relates to administering the active compounds to treat endocrine disorders. Endocrine disorders include primary or secondary adrenocortical insufficiency (Addison's Disease), primary or secondary adrenocortical excess (Cushing Syndrome); congenital adrenal hyperplasia, adrenal tumors, nonsuppurative thyroiditis and hypercalcemia associated with cancer.

A preferred embodiment of the present invention relates to administering the active compounds to treat inflammatory disorders. Inflammatory disorders include arthritis, osteoarthritis, rheumatoid arthritis, juvenile rheumatoid arthritis and asthma.

Another more specific and more preferred embodiment of the present invention relates to administering the active compounds to treat a disorder selected from osteoarthritis; psoriatic arthritis; rheumatoid arthritis; juvenile rheumatoid arthritis; ankylosing spondylitis; acute and subacute bursitis; acute nonspecific tenosynovitis; acute gouty arthritis; post-traumatic osteoarthritis; synovitis of osteoarthritis and epicondylitis.

Another embodiment of the present invention relates to administering the active compounds to treat collagen diseases. Collagen diseases include the treatment of exacerbation or maintenance therapy in systemic lupus erythematosus, acute rheumatic carditis and systemic dermatomyositis (polymyositis).

Another embodiment of the present invention relates to administering the active compounds to treat dermatologic diseases. Dermatologic diseases include pemphigus, bullous dermatitis herpetiformis, erythema multiforme, Stevens-Johnson syndrome, exfoliative dermatitis, mycosis fungoides; psoriasis and seborrheic dermatitis.

Another embodiment of the present invention relates to administering the active compounds so as to treat allergic states. Allergic states include control of severe or incapacitating allergic conditions intractable to adequate trials of conventional treatment, seasonal or perennial allergic rhinitis, bronchial asthma, contact dermatitis, atopic dermatitis, serum sickness, food allergies and drug hypersensitivity reactions.

Another embodiment of the present invention relates to administering the active compounds so as to treat ophthalmic diseases. Ophthalmic diseases include the treatment of severe acute and chronic allergic and inflammatory processes involving the eye and its adnexa, such as allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis and sympathetic ophthalmia.

Another embodiment of the present invention relates to administering the active compounds so as to treat respiratory diseases. Respiratory diseases include chronic obstructive pulmonary disease, asthma, acute respiratory distress syndrome, symptomatic sarcoidosis, Loeffler's syndrome; berylliosis, fulminating or disseminated pulmonary tuberculosis and aspiration pneumonitis, preferably chronic obstructive pulmonary disease and asthma.

Another embodiment of the present invention relates to administering the active compounds so as to treat hematologic disorders. Hematologic disorders include idiopathic thrombocytopenic purpura, secondary thrombocytopenia, acquired (autoimmune) hemolytic anemia, erythroblastopenia (RBC anemia) and congenital (erythroid) hypoplastic anemia.

Another embodiment of the present invention relates to administering the active compounds so as to treat neoplastic diseases. Neoplastic diseases include leukemias and lymphomas.

Another embodiment of the present invention relates to administering the active compounds so as to treat edematous states. Edematous states includes the induction of a diuresis or remission of proteinuria in the nephrotic syndrome, without uremia, of the idiopathic type or that due to lupus erythematosus.

Another embodiment of the present invention relates to administering the active compounds so as to treat gastrointestinal diseases. Gastrointestinal diseases include ulcerative colitis, inflammatory bowel diseases, Crohn's disease and regional enteritis.

Another embodiment of the present invention relates to administering the active compounds so as to treat a disorder selected from tuberculosis, tuberculosis meningitis, trichinosis with neurologic or myocardial involvement, graft vs. host transplant rejection, multiple sclerosis, glucocorticoid insufficiency; and systemic fungal infections.

It will be understood by those skilled in the art that while the compounds, isomers, prodrugs and pharmaceutically acceptable salts thereof of the present invention will typically be employed as selective agonists, partial agonists or antagonists, there may be instances where a compound with a mixed steroid receptor profile is preferred.

In addition, the present invention provides methods of treating a disorder selected from obesity, diabetes, gastrointestinal diseases, cardiovascular disease, hypertension, hematologic diseases, neoplastic diseases, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, edematous states, inflammatory diseases (such as osteoarthritis, rheumatoid arthritis, psoriatic arthritis, ankylosing spondylitis, asthma and rhinitis), collagen diseases, tests of adrenal function, viral infection, immunodeficiency, immunomodulation, autoimmune diseases, endocrine disorders, allergies, wound healing, dermatological disorders, ophthalmic diseases, compulsive behavior, multi-drug resistance, addiction, psychosis, anorexia, cachexia, post-traumatic stress syndrome, post-surgical bone fracture, medical catabolism and prevention of muscle frailty comprising administering to a mammal in need of such treatment.

a) an amount of a first compound, said first compound being a compound of formula I, an isomer thereof, a prodrug of said compound or isomer, or a pharmaceutically acceptable salt of said compound, isomer or prodrug; and b) a second compound selected from the group consisting of methotrexate, an analgesic (e.g. NSAIDS, CSAIDS COX-2 inhibitor), penicillamine, colloidal gold, phosphodiesterase inhibitors, cyclosporin, FK 506, biological inhibitors of TNFα or its receptor or IL-1 or its receptor (e.g. Enbrel or Remicade or Kineret), metalloprotease inhibitors, bronchodilators, antihistamines, pyrimidine synthesis inhibitors (leflunomide); and wherein the amounts of the first and second compounds result in a therapeutic effect. More particularly, it provides such methods wherein the second compound is celecoxib, rofecoxib, valdecoxib, etoricoxib, Enbrel, Remicade $D_2E_7$ or Kineret.

Non-dissociated agonists of the glucocorticoid receptor are efficacious agents for the treatment of various inflammatory diseases; however, treatment is often accompanied by undesirable side effects. These side effects include, but are not limited to, the following examples: metabolic effects, weight gain, muscle wasting, decalcification of the skeleton, osteoporosis, thinning of the skin and thinning of the skeleton. However, according to the present invention, glucocorticoid receptor modulators, preferably dissociated agonists of the glucocorticoid receptor, may be used in combination with glucocorticoid receptor agonists to block some of these side effects, without inhibiting the efficacy of the treatment. Thus, any glucocorticoid receptor agonist may be used as the second compound in the combination aspect of the present invention. This combination includes the treatment of various inflammatory diseases, such as arthritis (osteo and rheumatoid), asthma, rhinitis, or immunomodulation. Examples of glucocorticoid receptor modulators include those known in the art (many of which are described above) as well as the novel compounds of formula I of the present invention. More particularly, examples of glucocorticoid receptor modulators known in the art include, but are not limited to, certain nonsteroidal compounds, such as 5H-chromeno[3,4-f]quinolines, which are selective modulators of steroid receptors, as disclosed in U.S. Pat. No. 5,696,127; and certain steroid-compounds substituted at position 10, which possess antiglucocorticoid activity, and some of which have glucocorticoid activity, as disclosed in Published European Patent Application 0 188 396, published 23 Jul. 1986. Examples of glucocorticoid receptor agonists include those known in the art, such as prednisone (17,21-dihydroxypregnane-1,4-diene-3,11,20-trione), prednylidene ((11β)-11,17,21-trihydroxy-16-methylenepregna-1,4-diene-3, 20-dione), prednisolone ((11β)-11,17,21-trihydroxypregna-1,4-diene-3, 20-dione), cortisone (17α,21-dihydroxy-4-pregnene-3,11,20-trione), dexamethasone ((11β, 16α)-9-fluoro-11,17,21-trihydroxy-16-methylpregna-1,4-diene-3, 20-dione), and hydrocortisone (11β,17α,21-trihydroxypregn-4-ene-3, 20-dione). These compounds, which are glucocorticoid receptor agonists, will generally be administered in the form of a dosage unit at a therapeutically effective amount of such compound. For example, prednisone or an equivalent drug may be administered from about 5 to about 80 mg, depending on the condition; hydrocortisone may be administered from about 100 to about 400 mg, depending on the condition; and dexamethasone may be administered from about 4 to about 16 mg, depending on the condition. These doses are typically administered once to twice daily, and for maintenance purposes, sometimes on alternate days.

The present invention also relates to a pharmaceutical composition for treating a disorder, selected from the group consisting of obesity, diabetes, gastrointestinal diseases, cardiovascular disease, hypertension, hematologic diseases, neoplastic diseases, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, edematous states, inflammatory diseases (such as osteoarthritis, rheumatoid arthritis, psoriatic arthritis, ankylosing spondylitis, asthma and rhinitis), collagen diseases, tests of adrenal function, viral infection, immunodeficiency, immunomodulation, autoimmune diseases, endocrine disorders, allergies, wound healing, dermatological disorders, ophthalmic diseases, compulsive behavior, multi-drug resistance, addiction, psychosis, anorexia, cachexia, post-traumatic stress syndrome, post-surgical bone fracture, medical catabolism and prevention of muscle frailty in a mammal comprising a therapeutically effective amount of a compound of formula I, or a pharmaceutically acceptable salt or prodrug thereof and a pharmaceutically acceptable carrier.

In addition, the present invention provides for a pharmaceutical composition for treating a disorder selected from obesity, diabetes, gastrointestinal diseases, cardiovascular disease, hypertension, hematologic diseases, neoplastic diseases, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, edematous states, inflammatory diseases (such as osteoarthritis, rheumatoid arthritis, psoriatic arthritis, ankylosing spondylitis, asthma and rhinitis), collagen diseases, tests of adrenal function, viral infection, immunodeficiency, immunomodulation, autoimmune diseases, endocrine disorders, allergies, wound healing, dermatological disorders, ophthalmic diseases, compulsive behavior, multi-drug resistance, addiction, psychosis, anorexia, cachexia, post-traumatic stress syndrome, post-surgical bone fracture, medical catabolism and prevention of muscle frailty comprising, a) an amount of a first compound, said first compound being a compound of formula I, an isomer thereof, a prodrug of said compound or isomer, or a pharmaceutically acceptable salt of said compound, isomer or prodrug; and b) a second compound selected from the group consisting of methotrexate, an analgesic (e.g. NSAIDS, CSAIDS COX-2 inhibitor), penicillamine, colloidal gold, phosphodiesterase inhibitors, cyclosporin, FK 506, biological inhibitors of TNFα or its receptor or IL-1 or its receptor (e.g. Enbrel or Remicade or Kineret), metalloprotease inhibitors, bronchodilators, antihistamines, pyrimidine synthesis inhibitors (leflunomide); and wherein the amounts of the first and second compounds result in a therapeutic effect. More particularly, it provides such compositions wherein the second compound is celecoxib, rofecoxib, valdecoxib, etoricoxib, Enbrel, Remicade, $D_2E_7$ or Kineret.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein the term "mammals" is meant to refer to all mammals, including, for example, primates such as humans and monkeys. Examples of other mammals included herein are rabbits, dogs, cats, cattle, goats, sheep and horses. Preferably, the mammal is a human.

Active compounds as used herein refer to compounds of formula I described above, including all subgeneric and specific embodiments described herein. One skilled in the art will appreciate that since the compounds of the invention have differential glucocorticoid activity, (i.e. compounds are either agonists, partial agonist antagonists or mixtures thereof) that the use of any one compound for the treatment of a disorder is dependent on its specific glucocorticoid profile. For example, compounds with agonist activity are especially well suited for treating inflammation, primary or secondary adrenocortical insufficiency; systemic lupus erythematosus, dermatitis (Including seborrheic dermatitis), psoriasis, allergic states, allergic conjunctivitis, keratitis, iritis, iridocyclitis, chorioretinitis, diffuse posterior uveitis, choroiditis, optic neuritis, respiratory diseases, neoplastic diseases and inflammatory bowel diseases. Compounds with antagonist activity are especially well suited to treat obesity, diabetes and primary or secondary adrenocortical excess (Cushing Syndrome).

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

The present invention also relates to processes of preparing the compounds of formula I and intermediates used in such processes.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746, 530; indole and quinoline compounds such as MK-591, MK-886, and BAY×1005.

The present invention still further relates to the combination of a compound of the invention together with receptor antagonists for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists including cetirizine, loratadine, desloratadine, fexofenadine, astemizole, azelastine, and chlorpheniramine.

The present invention still further relates to the combination of a compound of the invention together with a gastroprotective $H_2$ receptor antagonist.

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents including ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with one or more (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; 0) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of NKP-608C; SB-233412 (talnetant); and D-4418; or (t) elastase inhibitors selected from the group consisting of UT-77 and ZD-0892.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the invention can also be used in combination with p38 inhibitors, P2X7 inhibitors, or $\alpha 2\Delta$ inhibitors (such as gabapentin or pregabalin).

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VegF inhibitors, COX-2 inhibitors and antimetabolites such as methotrexate antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline or fluoxetine); anti-Parkinsonian drugs (such as deprenyl, L-dopa, Requip, Mirapex, bromocriptine, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase); anti-anxiety drugs, such as benzodiazepine, valium, librium, or SSRI's; anti-psychotics, such as haloperidol, clozapine or ziprasidone; and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compounds of the present invention may also be used in combination with any aldose reductase inhibitor. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, Diabetes, 29:861–864, 1980, "Red Cell Sorbitol, an Indicator of Diabetic Control"). A variety of aldose reductase inhibitors are described and referenced below; however other aldose reductase inhibitors will be known to those skilled in the art. Examples of aldose reductase inhibitors useful in the compositions and methods of this invention include, for example, zopolrestat, and other such compounds as disclosed and described in PCT/IB99/00206, filed 5 Feb. 1999 (the disclosure of which is hereby incorporated by reference), and assigned to the assignee hereof.

Any glycogen phosphorylase inhibitor may be used in the combination aspect of this invention. The term glycogen phosphorylase inhibitor refers to any substance or agent or any combination of substances and/or agents which reduces, retards or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described in PCT/IB99/00206, filed 5 Feb. 1999). A variety of these compounds are described in the following published international patent applications: WO 96/39384, published 12 Dec. 1996, and WO 96/39385, published 12 Dec. 1996; and in the following filed international patent application: PCT/IB99/00206, filed 5 Feb. 1999; the disclosures of all of these applications are hereby incorporated by reference herein.

Any sorbitol dehydrogenase inhibitor may be used in the combination aspect of this invention. The term sorbitol dehydrogenase inhibitor refers to a compound which inhibits the enzyme sorbitol dehydrogenase, which catalyzes the oxidation of sorbitol to fructose. Such inhibition is readily determined by those skilled in the art according to standard assays (as described in U.S. Pat. No. 5,728,704 and references cited therein). A variety of these compounds are described and referenced below; however other sorbitol dehydrogenase inhibitors will be known to those skilled in the art. U.S. Pat. No. 5,728,704 (the disclosure of which is hereby incorporated by reference) discloses substituted pyrimidines which inhibit sorbitol dehydrogenase, lower fructose levels, and/or treat or prevent diabetic complications, such as diabetic neuropathy, diabetic retinopathy, diabetic nephropathy, diabetic microangiopathy and diabetic macroangiopathy.

Any known, commercially marketed antidiabetic compound may be used in the combination aspect of this invention. A variety of such compounds are described and referenced below; however other such compounds will be known to those skilled in the art. Examples of such compounds useful in the compositions and methods of this invention include, for example, insulin, metformin, troglitazone (REZULIN®) and sulfonylureas, such as glipizide (GLUCOTROL®), glyburide (GLYNASE®, MICRONASE®) and chlorpropamide (DIABINASE®).

Any $\beta$-adrenergic agonist may be used in the combination aspect of this invention. $\beta$-Adrenergic agents have been categorized into $\beta_1$, $\beta_2$, and $\beta_3$ subtypes. Agonists of $\beta$-receptors promote the activation of adenyl cyclase. Activation of $\beta_1$, receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate $\beta$ receptors are therefore useful as anti-obesity agents. Compounds which are $\beta_3$-receptors agonists have hypoglycemic and/or anti-diabetic activity. Such activity is readily determined by those skilled in the art according to standard assays (International Patent Application, Publication No. WO 96/35671). Several compounds are described and referenced below; however, other $\beta$-adrenergic agonists will be known to those skilled in the art. International Patent Application, Publication No. WO 96/35671 (the disclosure of which is incorporated herein by reference) discloses compounds, such as substituted aminopyridines, which are $\beta$-adrenergic agonists. International Patent Application, Publication No. 93/16189 (the disclosure of which is incorporated herein by reference) discloses the use of selective $\beta_3$ receptor agonists in combination with compounds which modify eating behavior for the treatment of obesity.

Any thyromimetic antiobesity agent may be used in the combination aspect of this invention. These compounds are tissue selective thyroid hormone agonists. These compounds are able to induce weight loss by mechanisms other than appetite suppression, e.g., through stimulation of the metabolic rate in peripheral tissue, which, in turn, produces weight loss. Such metabolic effect is readily measured by those skilled in the art according to standard assays. A variety of these compounds are described and referenced below; however other thyromimetic antiobesity agents will be known to those skilled in the art. It is well known to one of ordinary skill in the art that selectivity of thermogenic effect is an important requirement for a useful therapeutic agent in the treatment of, for example, obesity and related conditions.

Any eating behavior modifying compound may be used in the combination aspect of this invention. Compounds which modify eating behavior include anorectic agents, which are compounds which diminish the appetite. Such classes of anorectic agents are well known to one of ordinary skill in the art. A variety of these compounds are described in and referenced below; however, other anorectic agents will be known to those skilled in the art. Also, the following are antiobesity agents: phenylpropanolamine, ephedrine, pseudoephedrine, phentermine, a Neuropeptide Y (hereinafter also referred to as "NPY") antagonist, a cholecystokinin-A (hereinafter referred to as CCK-A) agonist, a monoamine reuptake inhibitor (such as sibutramine), a sympathomimetic agent, a serotoninergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a galanin antagonist or a GI lipase inhibitor or decreaser (such as orlistat). Other antiobesity agents include phosphatase 1B inhibitors, bombesin agonists, dehydroepiandrosterone or analogs thereof, glucocorticoid receptor modulators, orexin receptor antagonists, urocortin binding protein antagonists or glucagon-like peptide-1 (insulinotropin) agonists. A particularly preferred monoamine reuptake inhibitor is sibutramine, which can be prepared as disclosed in U.S. Pat. No. 4,929,629, the disclosure of which is incorporated herein by reference. Preferred serotoninergic agents include fenfluramine and dexfenfluramine, which can be prepared as disclosed in U.S. Pat. No. 3,198,834, the disclosure of which is incorporated herein by reference. A particularly preferred dopamine agonist is bromocriptine, which can be prepared as disclosed in U.S. Pat. Nos. 3,752,814 and 3,752,888, the disclosures of which are incorporated herein by reference. Another preferred anorectic agent is phentermine, which can be prepared as disclosed in U.S. Pat. No. 2,408,345, the disclosure of which is incorporated herein by reference.

Any NPY receptor antagonist may be used in the combination aspect of this invention. The term NPY receptor antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays (such as those described in International Patent Application, Publication No. WO 99/07703). In addition, the compounds described and referenced below are NPY receptor antagonists; however, other NPY receptor antagonists will also be known to those skilled in the art. International Patent Application, Publication No. WO 99/07703 (the disclosure of which is hereby incorporated by reference) discloses certain 4-aminopyrrole (3,2-d) pyrimidines as neuropeptide Y receptor antagonists. International patent application, Publication No. WO 96/14307, published 17 May 1996; International patent application, Publication No. WO 96/40660, published 19 Dec. 1996; International patent application, Publication No. WO 98/03492; International patent application, Publication No. WO 98/03494; International patent application, Publication No. WO 98/03493; International patent application, Publication No. WO 96/14307, published 17 May 1996; International patent application, Publication No. WO 96/40660, published 19 Dec. 1996; (the disclosures of which are hereby incorporated by reference) disclose additional compounds, such as substituted benzylamine derivatives, which are useful as neuropeptide Y specific ligands.

DETAILED DESCRIPTION OF THE INVENTION

The compounds of formula I of the present invention are prepared as described in the Schemes, Preparations and Examples below, or are prepared by methods analogous thereto, which are readily known and available to one of ordinary skill in light of this disclosure. Unless otherwise indicated, A, X, Y, n and $R^1$ through $R^{25}$ and structural formula I in the reaction Schemes and discussion that follow are as defined above. However, it will be understood by those skilled in the art that other functionalities disclosed herein at the indicated positions of compounds of Formula I also comprise potential substituents for the analogous positions on the structures within the Schemes.

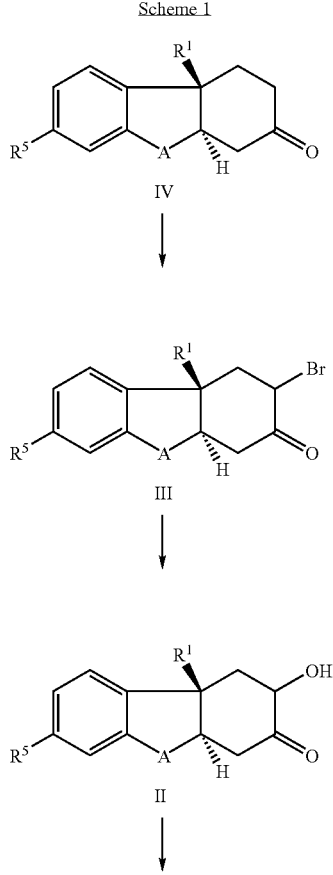

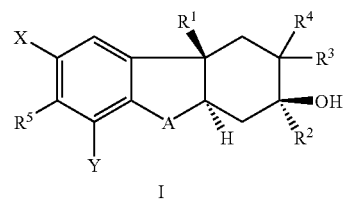

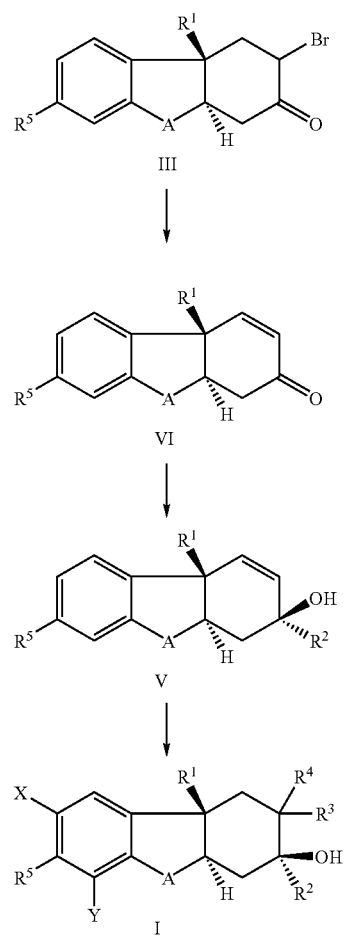

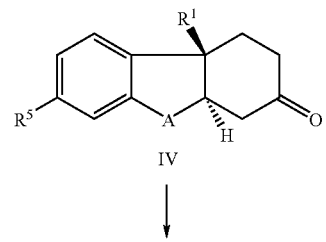

-continued
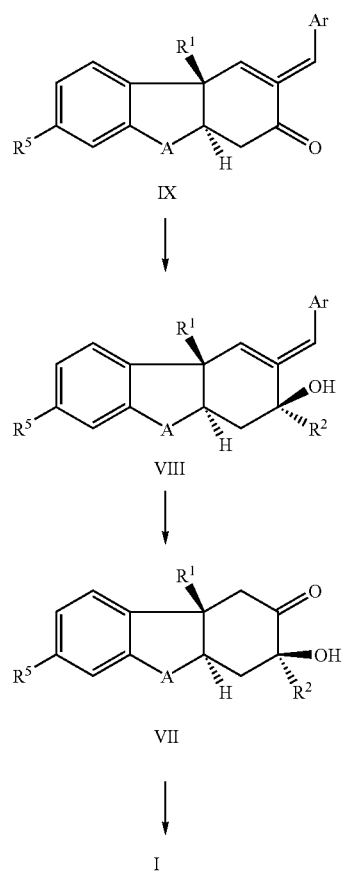
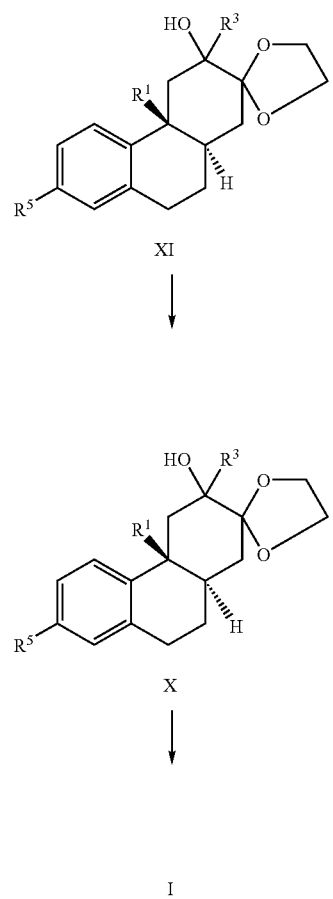
Scheme 4
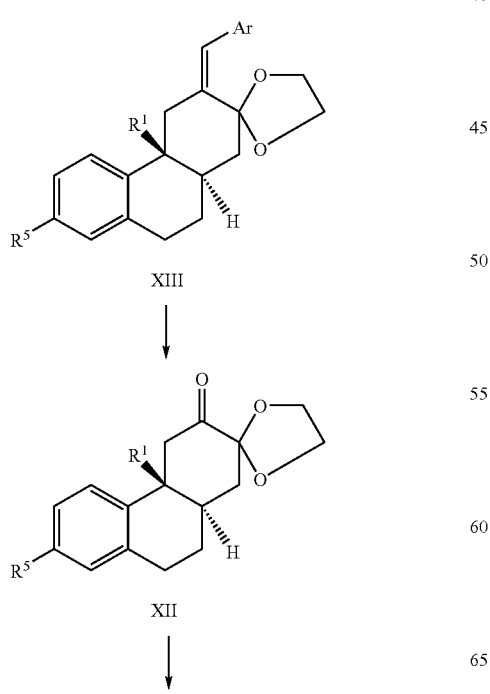
Scheme 5
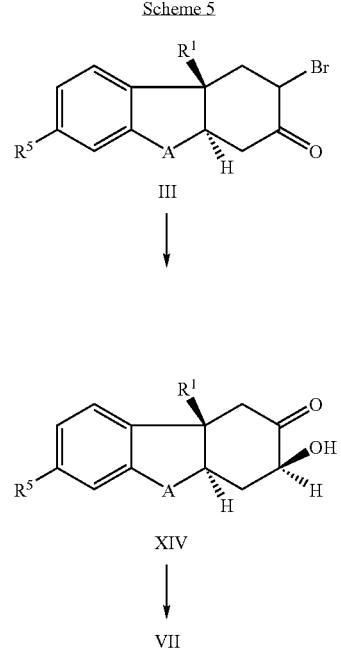

Scheme 5
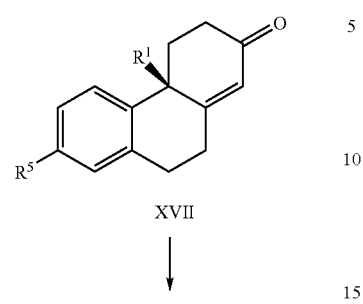
XVII
↓
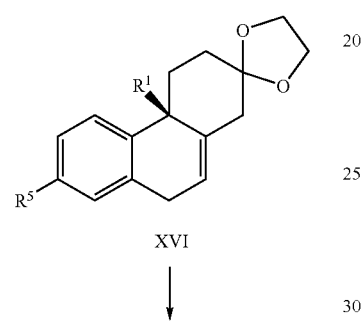
XVI
↓
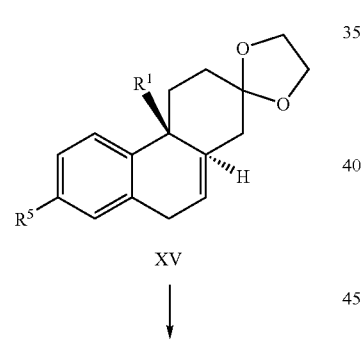
XV
↓
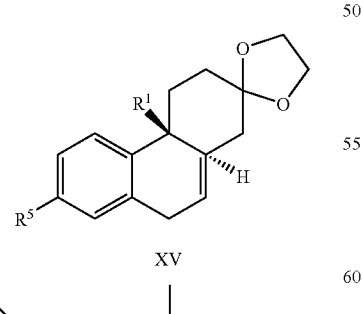
XV
↓
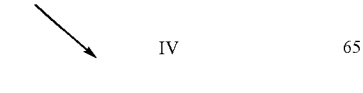
IV
Scheme 7
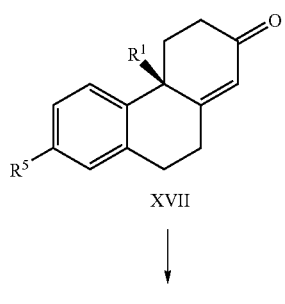
XVII
↓
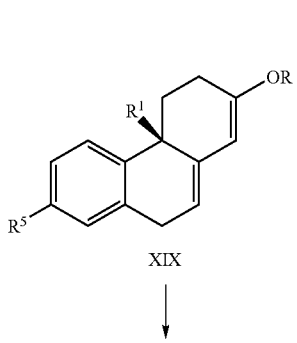
XIX
↓
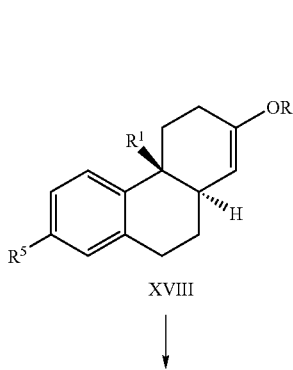
XVIII
↓
IV
Scheme 8
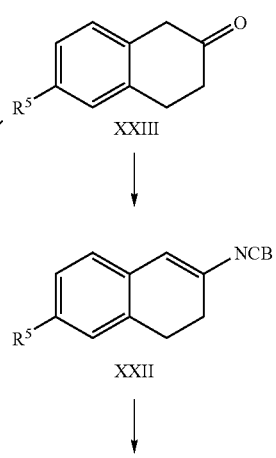
XXIII
↓
XXII
↓

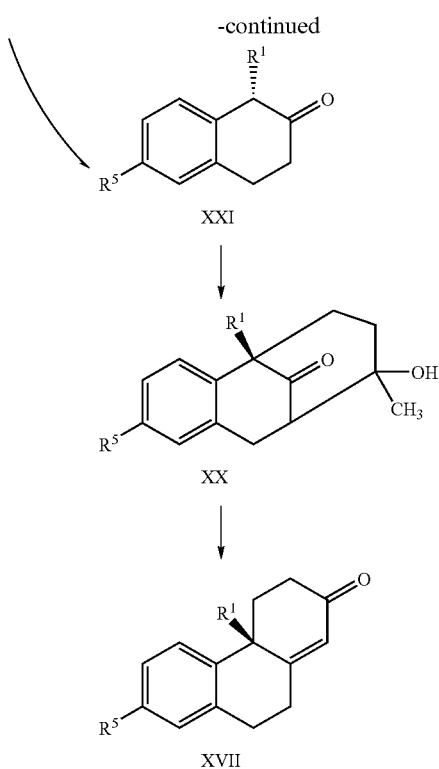

-continued

XXI

↓

XX

↓

XVII

Scheme 1 refers to the preparation of compounds of formula I. Compounds of formula I, wherein X and Y are each hydrogen, $R^5$ is hydrogen, OH, halo, —CN, or $(C_1-C_6)$alkyl-O—; one of $R^3$ or $R^4$ is OH and the other of $R^3$ or $R^4$ is hydrogen, and A is —$CH_2CH_2$—, can be prepared from compounds of formula II, wherein $R^5$ is hydrogen, —OH, halo, —CN, or $(C_1-C_6)$alkyl-O—; $R^3$ or $R^4$ is OH and A is —$CH_2CH_2$—, by the addition of a nucleophile of the formula $R^2$-M, wherein M is a metal, preferably lithium or magnesium. In certain instances it is advantageous to add an equivalent (relative to the organometallic species) of anhydrous cerium chloride to suppress enolization. The reaction is run in the presence of a solvent such as tetrahydrofuran, 1,2-dimethoxyethane or diethyl ether, preferably tetrahydrofuran at a temperature from about −78° C. to about 23° C. for a period from about 1 hour to about 18 hours. Additionally, when $R^5$ is OH, it is sometimes preferred to protect this group prior to addition of the organometallic species and subsequently deprotect to form the compound of formula I. Suitable protecting groups include trialkylsilyl, benzyl, tetrahydropyran-2-yl, methoxymethyl, preferably trialkylsilyl. See T. W. Green and Wuts, *Protective Groups in Organic Synthesis*, John Wiley & Sons, New York, 1991 especially Chapter 3 dealing with protecting groups of phenols. Preferably, the aforesaid protection or deprotection reaction is run in the presence of a solvent such as tetrahydrofuran, 1,2-dimethoxyethane or diethyl ether, preferably tetrahydrofuran. The aforesaid reaction is run at a temperature from about −78° C. to about 23° C. for a period from about 1 hour to about 18 hours.

Compounds of formula II can be prepared from compounds of formula III by reaction with an aqueous base. Suitable bases include aqueous alkali metal carbonates or hydroxide bases, preferably aqueous sodium hydroxide. Suitable co-solvents for the aforesaid reaction include water miscible solvents, such as dimethylformamide (DMF), or acetone. The aforesaid reaction may be run at a temperature between about 0° C. and 50° C. for about 1 to 24 hours.

Compounds of formula III can be prepared from compounds of formula IV by reaction with a suitable bromination reagent such as phenyl trimethylammonium tribromide, N-bromosuccinamide, pyridinium bromide perbromide, $Br_2$ or $Br_2$-$Ph_3P$. The bromination may be carried out in an inert solvent such as diethyl ether or tetrahydrofuran, preferably tetrahydrofuran. The aforesaid reaction is conducted at a temperature of about −78° C. to about 40° C., preferably about −78° C. to about 0° C., for a time period between about 1 hour to about 16 hours.

Compounds of the formula IV can be made by the methods of Schemes 6 or 7 or can be made by methods well known to those skilled in the art.

Compounds of formula I, wherein $R^5$ is other than hydrogen, OH, halo, —CN, or $(C_1-C_6)$alkyl-O—; $R^3$ or $R^4$ is other than OH and A is other than —$CH_2CH_2$—, can be prepared from compounds of formula I, wherein $R^5$ is hydrogen, OH, halo, —CN, or $(C_1-C_6)$alkyl-O—; $R^3$ or $R^4$ are OH and A is —$CH_2CH_2$—, by methods well known to those skilled in the art. Specifically, compounds of formula I, wherein $R^5$ is $(C_3-C_{10})$cycloalkyl-O—, $(C_1-C_9)$heterocyclic-O—, $(C_3-C_{10})$cycloalkyl-$(C_1-C_6)$alkyl-O—, $(C_6-C_{10})$aryl-$(C_1-C_6)$alkyl-O—, $(C_1-C_9)$heteroaryl-$(C_1-C_6)$alkyl-O—, and $(C_1-C_9)$heterocyclic-$(C_1-C_6)$alkyl-O—, can be prepared by alkylation conditions well known to those skilled in the art. An example of such methods include reaction with a compound of the formula $R^{5a}$L wherein L is a leaving group, and $R^{5a}$ is $(C_3-C_{10})$cycloalkyl-, $(C_1-C_9)$heterocyclic-, $(C_3-C_{10})$cycloalkyl-$(C_1-C_6)$alkyl-, $(C_6-C_{10})$aryl-$(C_1-C_6)$alkyl-, $(C_1-C_9)$heteroaryl-$(C_1-C_6)$alkyl-, and $(C_1-C_9)$heterocyclic-$(C_1-C_6)$alkyl-, in the presence of a base such as sodium carbonate $(Na_2CO_3)$, cesium carbonate, sodium hydride or potassium carbonate $(K_2CO_3)$, in a polar solvent such as acetone, dimethyl formamide or tetrahydrofuran at a temperature of about 10° C. to about the reflux temperature of the solvent.

Compounds of the formula I, wherein $R^5$ is $R^{18}$—(C=O)—O—, $R^{16}R^{17}N$—(C=O)—O— and $R^{16}R^{17}$—O—(C=O)—O— can be prepared by acylation conditions well known to those skilled in the art. An example of such methods include reaction with an acid chloride in the presence of a base such as triethylamine in a solvent such as dichloromethane or tetrahydrofuran, preferably dichloromethane, for a time period between about 10 minutes to about 120 minutes, preferably about 30 minutes, at a temperature of about 0° C. to about 22° C., preferably at about 0° C. Alternatively, a carboxylic acid can be reacted using amide coupling agents in a manner well known to one skilled in the art. One of ordinary skill in the art will appreciate that such reactions can be performed in the presence of a catalyst, such as a hydroxytriazole or pyridine based acylation catalyst, preferably HOBT, in an aprotic polar solvent, preferably methylene chloride, at a temperature range from 0–50° C. Alternatively, compounds of formula I, wherein $R^5$ is $R^{16}R^{17}N$—(C=O)—O—, can be prepared from compounds of formula I wherein $R^5$ is hydroxy by reaction with phosgene and a base to form an in situ carbamoyl chloride followed by reaction with an amine. Suitable bases include DMAP or triethylamine. Suitable solvents include toluene, benzene or cyclohexane. The reaction is conducted at a temperature from about 0° C. to about 30° C., preferably at about 22° C.

Compounds of formula I, wherein $R^5$ is $(C_6-C_{10})$aryl- or $(C_1-C_9)$heteroaryl-, can also be prepared by conversion of the compound of formula I, wherein $R^5$ is hydroxy, to the corresponding triflate followed by an organometallic coupling reaction. One such method is an aryl palladium coupling reaction, which is well known to those skilled in the art. One well known coupling method, so called Buchwald and Hartwig conditions, involves the coupling of a compound of the formula heteroaryl-H, wherein H is a hydrogen on a nitrogen ring atom, with the triflate of formula I in the presence of a palladium (0) catalyst and a base. Palladium (0) catalysts include tris(dibenzylidene acetone)dipalladium (O) ($Pd_2(dba)_3$), di(dibenzylidene acetone) palladium(O) ($Pd(dba)_2$), palladium acetate ($Pd(OAc)_2$), and a suitable ligand, such as a triaryl phosphine ligand, tri(t-butyl)phosphine, 1,1-bis(diphenylphosphanyl)ferrocene (DPPF), 2,2'-bis(diphenylphosphanyl)-1,1'-binaphthyl (BINAP), or PHANEPHOS, preferably tri(ortho-tolyl)phosphine. Suitable bases include $K_2CO_3$, $K_2PO_4$, $CsCO_3$, $LiN(TMS)_2$ or an alkoxide base such as sodium methoxide, sodium ethoxide, potassium t-butoxide, preferably sodium tert-butoxide. Suitable solvents include toluene or an ethereal solvent, preferably dioxane. The aforesaid reaction may be run at a temperature of about 40° C. to 110° C. for about 1 to 48 hours. Such conditions are reviewed in *Angew. Chem. Int. Ed. Engl.* 1998, 37, 2046–2067 and are well known to those of ordinary skill in the art. Preferred Buchwald conditions use palladium acetate ($Pd(OAc)_2$) or palladium tetra-triphenylphosphine ($Pd(PPh_3)_4$) as the source of the palladium. Suitable solvents include THF, toluene or ethereal solvents. The aforesaid reaction may be run at a temperature of about 25° C. to 110° C. for about 1 to 4 hours, preferably 2 hours. Nickel catalysts, such as Ni(cod) (nickel 1,5-cyclooctadiene), are also well known.

Alternatively, compounds of formula I, wherein $R^5$ is ($C_1$–$C_6$)alkyl, ($C_2$–$C_6$)alkenyl, ($C_3$–$C_{10}$)cycloalkyl, ($C_6$–$C_{10}$)aryl-, ($C_1$–$C_9$)heteroaryl-, ($C_1$–$C_9$)heterocyclic-, ($C_6$–$C_{10}$)aryl-($C_1$–$C_6$)alkyl, ($C_1$–$C_9$)heteroaryl-($C_1$–$C_6$)alkyl, or ($C_1$–$C_9$)heterocyclic-($C_1$–$C_6$)alkyl, can also be prepared by a so called Suzuki coupling reaction of said compound of formula I, wherein $R^5$ is a triflate, with an $R^5$-boronate or boronic acid, wherein $R^5$ is ($C_6$–$C_{10}$)aryl- or ($C_1$–$C_9$)heteroaryl-, a catalyst, and a base. Suitable borates include $(HO)_2B$—, 9-BBN, and alkylboranes. Suitable catalysts include copper or palladium (such as palladium acetate ($Pd(OAc)_2$), palladium triphenylphosphine or $Pd(dppf)Cl_2$), preferably copper (II) acetate. Suitable bases include tertiary amine bases, such as triethylamine or pyridine, $Na_2CO_3$, sodium ethoxide, and $K_3PO_4$. Suitable solvents include methylene chloride, dimethyl sulfoxide (DMSO) or tetrahydrofuran (THF). The aforesaid reaction is typically performed under an atmosphere of oxygen gas at a temperature of about 10° C. to 50° C., preferably about 23° C. for about 6 to 72 hours. Palladium-catalyzed boronic acid couplings are described in Miyaura, N.; Yanagi, T., Suzuki, A. *Syn. Comm.* 1981, 11, 7, p. 513.

Alternatively, compounds of formula I, wherein $R^5$ is ($C_3$–$C_6$)alkynyl, can be prepared by a so called Castro-Steven reaction, wherein a compound of formula I, wherein $R^5$ is a triflate, is reacted with a ($C_3$–$C_6$)alkynyl in the presence of a base and a catalyst in a suitable solvent. Suitable bases include alkylamines such as diethylamine. Suitable catalysts include copper iodide (CuI) with palladium terta-triphenylphosphine ($Pd(PPh_3)_4$). Suitable solvents include dimethyl formamide. The aforesaid reaction is run at a temperature from about 0° C. to about 30° C., preferably about 20–22° C., for a period from about 1 to about 6 hours, preferably about 4 hours. Other examples of similar reaction conditions can found in Arcadi et al., *Tetrahedron*, 50, 2, 437–452 (1994).

Compounds of formula I, wherein $R^5$ is ($C_6$–$C_{10}$)aryl-O— or ($C_1$–$C_9$)heteroaryl-O—, can be prepared according to a so called Ullmann reaction by reaction of a compound of the formula I, wherein $R^5$ is —OH, with a compound of the formula $R^5$—X, wherein X is a triflate or a halide and $R^5$ is ($C_6$–$C_{10}$)aryl- or ($C_1$–$C_9$)heteroaryl-, in the presence of a suitable base and a suitable catalyst. Suitable bases include alkali metal carbonates or hydroxide bases, preferably potassium carbonate. Suitable catalysts include copper (0) catalyst, preferably finely powdered copper bronze. Suitable solvents for the aforesaid reaction include neat or polar aprotic solvents, such as dimethylformamide (DMF), N,N dimethylacetamide or N-methylpyrrolidinone (NMP). The aforesaid reaction may be run at a temperature between about 80° C. and 180° C. for about 6 to 24 hours.

Compounds of the formula I, wherein $R^5$ is $R^{16}R^{17}N$—(C=O)—, can be prepared by hydrolysis of the compound of formula I, wherein $R^5$ is —C≡N, to the acid followed by amidation reactions well known to those skilled in the art. The intermediate acid may alternatively be used to prepare compounds of formula I, wherein $R^5$ is $R^{19}$—O—(C=O)— and $R^{19}$ is ($C_1$–$C_6$)alkyl, by esterification. Compounds of the formula I, wherein $R^5$ is $R^{18}$—(C=O)—, can be prepared from compounds of formula I, wherein R is nitrite, by reaction with an organometallic reagent of the formula $R^{18}$-M, wherein M is a metal, preferably lithium or magnesium.

Compounds of the formula I, wherein X and Y are fluoro, chloro or bromo, can be prepared from compounds of formula I, wherein X and Y are each hydrogen, by reaction with a halogenating reagent such as phenyl trimethylammonium tribromide, N-bromosuccinimide, N-chlorosuccinimide, pyridinium bromide perbromide, $Br_2$, $Cl_2$, or $Br_2$-$Ph_3P$, according to methods well known to those skilled in the art.

Compounds of the formula I, wherein one or both of X and Y are alkyl, can be prepared from compounds of formula I, wherein X and Y are chloro or bromo, by reaction with an alkyl-metal in the presence of a catalyst. Suitable metals and catalysts as well as solvents and conditions are well known to those skilled in the art.

Compounds of formula I, wherein each of the aforesaid ($C_1$–$C_6$)alkyl, ($C_3$–$C_{10}$)cycloalkyl, ($C_6$–$C_{10}$)aryl, ($C_1$–$C_9$) heteroaryl, ($C_1$–$C_9$)heterocyclic moieties of said ($C_1$–$C_6$) alkyl-O—, ($C_3$–$C_{10}$)cycloalkyl-O—, ($C_6$–$C_{10}$)aryl-O—, ($C_1$–$C_9$)heteroaryl-O—, ($C_1$–$C_9$)heterocyclic-O—, ($C_3$–$C_{10}$)cycloalkyl-($C_1$–$C_6$)alkyl-O—, ($C_6$–$C_{10}$)aryl-($C_1$–$C_6$)alkyl-O—, ($C_1$–$C_9$)heteroaryl-($C_1$–$C_6$)alkyl-O— and ($C_1$–$C_9$)heterocyclic-O— radicals, are optionally substituted with one to three substituents independently selected from the group consisting of ($C_1$–$C_6$)alkyl, ($C_2$–$C_6$)alkenyl, ($C_2$–$C_6$)alkynyl, ($C_3$–$C_{10}$)cycloalkyl, ($C_6$–$C_{10}$)aryl, ($C_1$–$C_9$) heteroaryl, ($C_1$–$C_9$)heterocyclic, halo, HO—, HO—(C=O)—, $R^{18}$—(C=O)—, $R^{18}$—$CO_2$—, N≡C—, $R^{18}R^{19}N$—, $R^{18}R^{19}N$—(C=O)—, $R^{18}(C=O)$—NH—, and $R^{18}(C=O)$—N[($C_1$–$C_6$)alkyl]-; can be prepared by additional methods well known to those skilled in the art or can be added in during the aforesaid reactions as pre-existing functional groups.

Scheme 2 refers to an alternative preparation of compounds of the formula I, wherein A is —$CH_2CH_2$—, one of $R^3$ or $R^4$ is hydroxy and the other of $R^3$ or $R^4$ is hydrogen and $R^1$ is other than alkenyl, from compounds of the formula III, wherein A is —$CH_2CH_2$—, and $R^1$ is other than alkenyl. Referring to Scheme 2, a compound of the formula I, wherein $R^3$ is hydrogen, can be prepared from a compound of the formula V by reaction with a hydroboration reagent, such as $BH_3$ in THF, in an aprotic solvent, such as THF or dioxane, at a temperature from about 0° C. to about 60° C. and then treated with an oxidizing agent, such as hydrogen peroxide or sodium perborate, at a temperature from about 0° C. to about 60° C. Other comparable methods known in the art, are exemplified in *Comprehensive Organic Transformations*, R. C. Larock, VCH Publishers Inc. (1989), pp. 497–498.

A compound of the formula V can be prepared from a compound of the formula VI by reaction with a Grignard reagent or organolithium reagent as described above in Scheme 1 for the conversion of a compound of formula II to a compound of formula I.

A compound of the formula VI can be prepared from a compound of formula III by reaction with a base such as calcium carbonate or a tertiary amine base. Illustrative examples of tertiary organic amine bases include triethylamine, diisopropylethylamine, benzyl diethylamino, dicyclohexylmethyl-amine, 1,8-diazabicyclo[5.4.0]undec-7-ene ("DBU"), 1,4-diazabicyclo[2.2.2]octane ("TED"), and 1,5-diazabicycle[4.3.0]non-5-ene. Suitable solvents for the aforesaid reaction include aprotic solvents, such as dimethylformamide (DMF), toluene, N,N dimethylacetamide or N-methylpyrrolidinone (NMP). The aforesaid reaction may be run at a temperature between about 100° C. and 180° C. for about 1 to 12 hours.

Compounds of the formula III can be prepared according to the methods of Scheme 1 or can be made by methods well known to those skilled in the art.

Scheme 3 refers to an alternate preparation of compounds of formula I; wherein A is —$CH_2$—$CH_2$—; $R^1$ is other than alkenyl; and $R^5$ is —OH, —CN or alkoxy; from compounds of the formula IV; wherein A is —$CH_2$—$CH_2$—; $R^1$ is other than alkenyl and $R^5$ is —OH, —CN or alkoxy. Referring to Scheme 3, a compound of the formula I can be prepared from a compound of formula VII by reaction with an organometallic reagent according to methods analogous to those described above for the conversion of compounds of formula II to formula I in Scheme 1.

A compound of the formula VII can be prepared by ozonolysis of a compound of the formula VII in a solvent such as methanol or in a methanol/methylene chloride mixture, preferably in methanol, at a temperature of from −78° C. to 0° C., preferably about −78° C., for a period of time from about 5 minutes to about 2 hours, preferably about 10 minutes. The reaction is worked up by quenching with a reductant, such as dimethylsulfide or triphenylphosphine, preferably dimethylsulfide. One skilled in the art will appreciate that when $R^5$ is —OH that it is preferable to protect the phenol as an acyl derivative before ozonolysis and then remove it by saponification after the reductive quench.

A compound of the formula VIII can be prepared from a compound of the formula IX by reaction with a Grignard or organometallic reagent according to methods analogous to those described above for the conversion of compounds of formula II to formula I in Scheme 1.

A compound of the formula IX can be prepared from a compound of the formula IV by an aldol condensation. For example, a compound of the formula IV can be reacted with an aldehyde of the formula Ar—(C=O)—H (wherein Ar is aryl) in the presence of a base to form an aldol intermediate, which may be isolated or converted directly in the same reaction step to a compound of the formula IX by the loss of water. In such case, the aldol intermediate may be converted into the compound of formula IX by the elimination of water using techniques which are familiar to those skilled in the art, for example, by heating to the reflux temperature a solution of the aldol intermediate in a solvent such as benzene, toluene or xylene, in the presence of a catalytic amount of benzene- or p-toluene-sulfonic acid with provision for the removal of the water generated. Such water removal techniques may involve the use of molecular sieves or a Dean-Stark trap to isolate the water created as an azeotrope with the solvent. The aldol reaction is typically carried out in a polar solvent such as dimethylformamide (DMF), tetrahydrofuran (THF), methanol or ethanol, at a temperature from about −78° C. to about 80° C. Preferably, this reaction is carried out in THF at about 25° C. Suitable bases for use in the aldol formation step include sodium hydride (NaH), sodium methoxide, sodium methoxide, potassium-tert.-butoxide, lithium diisopropylamide, pyrrolidine and piperidine. Sodium ethoxide is preferred. Aldol condensations are described in "*Modern Synthetic Reactions*," Herbert O. House, 2d. Edition, W. A. Benjamin, Menlo Park, Calif., 629–682 (1972) and *Tetrahedron*, 38 (20), 3059 (1982).

Compounds of the formula IV can be prepared according to the methods of Schemes 6 and 7 or can be made by methods well known to those skilled in the art.

Compounds of formula I, wherein $R^1$ is other than alkenyl and A is —$CH_2$—$CH_2$—, can be converted to compounds of formula I, wherein $R^1$ is other than alkenyl and A is —(C=O)—$CH_2$—, by oxidation using ozone in an inert solvent such as dichloromethane, methanol or a mixture of dichloromethane and methanol at a temperature from about −78° C. to about 0° C., preferably about −78° C. The reaction is worked up by quenching with a reductant such as dimethylsulfide or triphenylphosphine, preferably dimethylsulfide. One skilled in the art will appreciate that when $R^5$ is —OH that it is preferable to protect the phenol as an acyl derivative before the ozonolysis and then remove it by saponification after the reductive quench. Furthermore, in cases where the group $R^5$ is reactive towards ozone, it may be preferable to carry out the oxidation prior to full elaboration of the $R^5$ group, i.e. at the stage wherein $R^5$ is —OH, CN, or bromo. In other cases, e.g. wherein $R^1$ is alkenyl, alternative oxidation conditions can be used such as chromium trioxide in pyridine.

Compounds of formula I, wherein A is —(C=O)—$CH_2$—, can be converted to compounds of formula I, wherein A is —(C=O)—$CHR^{10}$— and $R^{10}$ is alkyl, by reaction with a base such as lithium diisopropylamide and an alkylating agent of the formula $R^{10}X$, wherein X is a leaving group such as bromo, iodo or methanesulfonate, in an inert solvent such as THF at a temperature from about −78° C. to about 0° C., preferably around −78° C.

Compounds of formula I, wherein A is —(C=O)—$CHR^{10}$— and $R^{10}$ is hydrogen or alkyl, can be converted to compounds of formula I, wherein A is —(C=O)—$CR^{10}R^{11}$—, $R^{10}$ is hydrogen or alkyl and $R^{11}$ is alkyl, by reaction with a base such as lithium diisopropylamide and an alkylating agent of the formula $R^{11}X$, wherein X is a leaving group such as bromo, iodo or methanesulfonate, in an inert solvent such as THF at a temperature from about −78° C. to about 0° C., preferably around −78° C.

Compounds of the formula I, wherein A is —(C=O)—$CR^{10}R^{11}$— and $R^{10}$ and $R^{11}$ are independently hydrogen or alkyl, can be converted to compounds of the formula I, wherein A is —CH(OH)—$CR^8R^9$—and $R^8$ and $R^9$ are independently hydrogen or alkyl, by treatment with a hydride donor such as sodium borohydride or lithium aluminum hydride in an inert solvent such as THF or diethyl ether at a temperature from about −20° C. to about 50° C.

Compounds of the formula I, wherein A is —(C=O)—CR$^{10}$R$^{11}$— and R$^{10}$ and R$^{11}$ are independently hydrogen or alkyl, can be converted to compounds of the formula I, wherein A is —CR$^6$(OH)—CR$^8$R$^9$—, R$^6$ is alkyl and R$^8$ and R$^9$ are independently hydrogen or alkyl, by treatment with an organometallic species of the formula R$^6$M, wherein M is a metal such as lithium or magnesium, in an inert solvent such as THF or diethyl ether at a temperature from about −78° C. to about 25° C.

Compounds of the formula I, wherein A is —CR$^6$(OH)—CHR$^8$— and R$^6$ and R$^8$ are independently hydrogen or alkyl, can be converted to compounds of the formula I, wherein A is —CR$^{12}$=CR$^{13}$— and R$^{12}$ and R$^{13}$ are independently hydrogen or alkyl, by treatment with an acid such as trifluoroacetic acid or hydrochloric acid in an appropriate solvent such as dichloromethane or tetrahydrofuran. Alternatively the conversion can be accomplished by use of the Burgess reagent (methoxycarbonylsulfamoyl)triethylammonium hydroxide, inner salt).

Compounds of the formula I, wherein R$^1$ is other than alkenyl, A is —CR$^{12}$=CR$^{13}$— and R$^{12}$ and R$^{13}$ are independently hydrogen or alkyl, can be converted to compounds of the formula I, wherein A is —CHR$^6$—C(OH)R$^8$—, R$^6$ and R$^8$ are independently hydrogen or alkyl and R$^1$ is other than alkenyl, by treatment with a hydroboration reagent such as diborane in an aprotic solvent such as THF or dioxane at a temperature from about 0° C. to about 60° C. followed by oxidation of the alkyl borane intermediate with hydrogen peroxide or sodium perborate at a temperature from about 0° C. to about 60° C.

Compounds of the formula I, wherein A is —CHR$^6$—CH(OH)— and R$^6$ is hydrogen or alkyl, can be converted to compounds of the formula I, wherein A is —CHR$^6$—(C=O)— and R$^6$ is hydrogen or alkyl, by oxidation under Swern conditions or by treatment with pyridinium chlorochromate in an inert solvent such as dichloromethane.

Compounds of the formula I wherein A is —CHR$^6$—(C=O)— and R$^6$ is hydrogen or alkyl, can be converted to compounds of the formula I, wherein A is —CR$^6$R$^7$—(C=O)—, R$^6$ is hydrogen, or alkyl and R$^7$ is alkyl, by reaction with a base such as lithium diisopropylamide and an alkylating agent of the formula R$^7$X, wherein X is a leaving group such as bromo, iodo or methanesulfonate, in an inert solvent such as THF at a temperature from about −78° C. to about 0° C., preferably around −78° C.

Compounds of the formula I, wherein A is —CR$^6$R$^7$—(C=O)— and R$^6$ and R$^7$ are independently hydrogen or alkyl, can be converted to compounds of the formula I, wherein A is —CR$^6$R$^7$—C(OH)R$^8$—, R$^6$ and R$^7$ are independently hydrogen or alkyl and R$^8$ is alkyl, by treatment with an organometallic species of the formula R$^8$M, wherein M is a metal such as lithium or magnesium, in an inert solvent such as THF or diethyl ether at a temperature from about −78° C. to about 25° C.

Compounds of the formula I, wherein A is —CR$^6$R$^7$—(C=O)— and R$^6$ and R$^7$ are independently hydrogen or alkyl, can be converted to compounds of the formula I, wherein A is —CR$^6$R$^7$—CH(OH)— and R$^6$ and R$^7$ are independently hydrogen or alkyl, by treatment with a hydride donor such as lithium aluminum hydride in an inert solvent such as THF or diethyl ether at a temperature from about −20° C. to about 50° C.

Compounds of the formula I, wherein R$^1$ is other than alkenyl, A is —CR$^{12}$=CR$^{13}$— and R$^{12}$ and R$^{13}$ are independently hydrogen or alkyl, can be converted to compounds of the formula I, wherein A is —C(OH)R$^6$—C(OH)R$^8$— and R$^6$ and R$^8$ are hydrogen or alkyl and R$^1$ is other than alkenyl, by reaction with N-methylmorpholine-N-oxide and a catalytic quantity of osmium tetraoxide in a solvent such as a mixture of acetonitrile, acetone and water at a temperature from about 0° C. to about 50° C.

Other compounds of the formula I, wherein R$^4$ is R$^{14}$R$^{15}$N, can be prepared from a compound of formula VII or VIIa by reaction with ammonium chloride followed by reduction in the presence of reducing agent such as sodium borohydride.

One skilled in the art will appreciate that in the aforesaid preparations of compounds of formula I that R$^5$ may be suitably protected. Additionally, one skilled in the art will appreciate that the compounds of formula I so formed may be additionally derivatized to other compounds of formula I by methods well known to those skilled in the art. Specifically, compounds of formula I, wherein A is

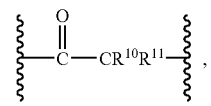

or wherein at least one of R$^{10}$ or R$^{11}$ is hydrogen, can be alkylated by methods well known to those skilled in the art.

Scheme 4 refers to an alternate preparation of compounds of the formula I; wherein A is —CH$_2$—CH$_2$—, R$^1$ is other than alkenyl, and R$^5$ is —OH, —CN or alkoxy; from compounds of the formula XIII. Referring to Scheme 4, a compound of the formula I can be prepared from a compound of the formula X, by reaction with an organometallic reagent according to methods analogous to those described above for the conversion of compounds of formula II to formula I in Scheme 1.

A compound of the formula X can be prepared from a compound of the formula XI by hydrolysis in the presence of aqueous acid. Suitable acids include sulfuric acid or hydrochloric acid, preferably hydrochloric acid. The reaction is carried out at a temperature ranging from about 20° C. to about 100° C.; preferably the temperature is about 70° C. The reaction is conducted over a period of about 0.5 hours to about 6 hours, preferably about 1 hour. A co-solvent such as dioxane or tetrahydrofuran may optionally be used.

The compound of formula XI can be prepared from a compound of formula XII by reaction with an organometallic reagent according to methods analogous to those described above for the conversion of compounds of formula II to formula I in Scheme 1.

The compound of formula XII can be prepared from a compound of formula XIII by methods analogous to those for the conversion of compounds of formula VIII to VII in Scheme 3.

The compound of formula XIII can be prepared from a compound of formula IX, from Scheme 3 by methods analogous to those for the conversion of compounds of formula XVII to formula XVI in Scheme 6.

Scheme 5 refers to an alternate preparation of compounds of the formula VII; wherein R$^2$ is benzyl or allyl, A is —CH$_2$—CH$_2$—, and R$^5$ is —OH, —CN or alkoxy; from compounds of formula III; wherein A is —CH$_2$—CH$_2$—, and R$^5$ is —OH, —CN or alkoxy. Compounds of formula VII are intermediates in the preparation of compounds of formula I, in Scheme 3. Referring to Scheme 5, a compound of the formula VII can be prepared from a compound of the formula XIV by reaction an R$^2$-halide, preferably the iodide derivative, in the presence of a base, such as potassium hexamethyldisilazide, or lithium diisopropylamide, preferably potassium hexamethyldisilazide. The reaction is stirred in an aprotic solvent, such as THF or diethyl ether, at room temperature, for a time period between about 2 hours to about 48 hours, preferably about 18 hours.

A compound of the formula XIV can be prepared from a compound of the formula III by reaction with an aqueous base. Suitable bases include aqueous alkali metal carbonates or hydroxide bases, preferably sodium hydroxide. Suitable co-solvents for the aforesaid reaction include water miscible solvents, such as dimethylformamide (DMF) or acetone. The aforesaid reaction may be run at a temperature between about 0° C. and 50° C. for about 6 to 24 hours.

Compounds of the formula III can be prepared according to the methods of Scheme 1 or can be made by methods well known to those skilled in the art.

Scheme 6 refers to the preparation of compounds of the formula IV; wherein A is —$CH_2$—$CH_2$—, and $R^5$ is —OH, —CN or alkoxy; which are intermediates in Schemes 1 and 3. Referring to Scheme 6, a compound of the formula IV can be prepared from a compound of formula XVII by a dissolving metal reduction wherein the compound of formula XVII is treated with a metal, such as sodium or lithium, preferably lithium, in liquid ammonia. Preferably a co-solvent such as tetrahydrofuran (THF) is used. The aforesaid reaction may be run at a temperature from about −78° C. to about −33° C., for a period from about 30 minutes to about 16 hours.

Alternatively, a compound of the formula IV, wherein $R^5$ is halo, OH, —CN or alkoxy, and $R^1$ is other than alkenyl, can be prepared from a compound of the formula XV by hydrolysis in the presence of aqueous acid and a co-solvent such as dioxane. Suitable acids include hydrochloric and sulfuric acid, preferably hydrochloric acid. The reaction is carried out at a temperature ranging from about 0° C. to 50° C.; preferably the temperature may range from about 20° C. to about 25° C. (i.e. room temperature). The reaction is conducted over a period of about 2 hours to about 48 hours, preferably about 16 hours.

A compound of the formula XV, wherein $R^5$ is OH, —CN or alkoxy, can be prepared from a compound of the formula XVI by reaction with hydrogen gas ($H_2$), using catalysts such as palladium on carbon (Pd/C), palladium on barium sulfate (Pd/$BaSO_4$), platinum on carbon (Pt/C), or tris(triphenylphosphine) rhodium chloride (Wilkinson's catalyst), in an appropriate solvent such as methanol, ethanol, THF, dioxane or ethyl acetate, at a pressure from about 1 to about 100 atmospheres and a temperature from about 10° C. to about 150° C., as described in *Catalytic Hydrogenation in Organic Synthesis*, Paul Rylander, Academic Press Inc., San Diego, 31–63 (1979). The following conditions are preferred: Pd(OH)$_2$ on carbon, toluene at 70° C. and 50 psi of hydrogen gas pressure. This method also provides for introduction of hydrogen isotopes (i.e., deuterium, tritium) by replacing $^1H_2$ with $^2H_2$ or $^3H_2$ in the above procedure. Compounds of the formula XV, wherein $R^5$ is halo, can be prepared by reduction with diimide or by reaction with copper(I) hydride triphenylphosphine complex (See Tetrahedron Letters, (31) 3237 (1990)).

A compound of the formula XVI can be prepared from a compound of the formula XVII by reaction with ethylene glycol in the presence of a solvent such as benzene or toluene and a catalytic amount of an acid such as p-toluenesulfonic acid. The reaction is heated to about the boiling point of the solvent for a period of time between 2 hours and 24 hours to give the ketal.

Compounds of the formula XVII can be prepared according to the methods of Scheme 8 or can be made by methods well known to those skilled in the art.

Scheme 7 refers to an alternate preparation of compounds of the formula IV; wherein A is —$CH_2$—$CH_2$—, $R^1$ is other than alkenyl, and $R^5$ is —OH, —CN or alkoxy. Compounds of formula IV are intermediates in the preparation of compounds of formula I in Schemes 1 and 3. Referring to Scheme 7, a compound of formula IV is prepared from a compound of formula XVIII by aqueous acid hydrolysis according to methods analogous to those described in Scheme 6 for the conversion of compounds of formula XV to formula IV.

A compound of formula XVIII can be prepared from a compound of formula XIX by hydrogenation according to methods analogous to those described in Scheme 6, for the conversion of compounds of formula XVI to formula XV.

A compound of formula XIX can be prepared from a compound of formula XVII by reaction with a trialkyl orthoformate in the presence of a catalytic amount of acid, in a reaction inert solvent at a temperature in the range from 0° C. to the reflux temperature of the reaction mixture for from 1 minutes to 120 hours. Suitable solvents include alcohols (such as methanol, ethanol or propanol), toluene or tetrahydrofuran. Suitable acids include para-toluene sulfonic acid or a dry mineral acid, preferably p-toluene sulfonic acid.

Compounds of the formula XVII can be prepared according to the methods of Scheme 8 or are commercially available or can be made by methods well known to those skilled in the art.

Scheme 8 refers to the preparation of a compound of formula XVII which is an intermediate in Schemes 6 and 7. Referring to Scheme 8, a compound of formula XVII, wherein $R^5$ is halogen, hydrogen, alkoxy, or benzyloxy, can be prepared by reaction of a compound of the formula XX with a base, such as sodium methoxide or KOH, in a solvent, such as methanol, or is reacted with an acid such as p-toluenesulfonic acid in a solvent such as toluene.

Alternatively, compounds of formula XVII are prepared from the compound of formula XX, by other reported, annulation methods, some of which are described in M. E. Jung, *Tetrahedron,* 1976, 32, pp. 3–31 and PCT Publication WO 00/66522.

Compounds of the formula XVII, wherein $R^5$ is hydroxy, can be prepared from other compounds of the formula XVII, wherein $R^5$ is methoxy, by reaction with $BBr_3$ or $BCl_3$ and tetrabutylammonium iodide or dimethylboron bromide in an aprotic solvent, such as dichloromethane or toluene at −78° C. to room temperature. Alternatively, the aforesaid reaction can be run with methionine in methanesulfonic acid at a temperature from about 0° C. to about 50° C., preferably at about room temperature.

Alternatively, compounds of the formula XVII, wherein $R^5$ is hydroxy, can be prepared from compounds of the formula XVII, wherein $R^5$ is methoxy, by reaction with sodium ethanethiol in DMF or reaction with methionine in methanesulfonic acid.

Compounds of the formula XVII, wherein $R^5$ is —CN, can be prepared from other compounds of the formula XVII, wherein $R^5$ is bromo, by reaction with zinc cyanide in the presence of a catalyst such as tetrakis(triphenylphosphine) palladium (0) in a solvent such as dimethylformamide or N,N-dimethylacetamide.

Also, the compound of formula XVII, wherein $R^5$ is hydroxy may be prepared by other literature methods as described in *Protecting Groups in Organic Synthesis*, Second Edition, T. W. Greene and P. G. M. Wuts, John Wiley and Sons, Inc. (1991) or as illustrated in *Comprehensive Organic Transformation*, R. C. Larock, VCH Publishers Inc. (1989), pp. 501–527.

The compound of Formula XX is prepared by reaction of a compound of formula XXI with (S)-(−)-α-methylbenzylamine to form an in situ intermediate imine that is then reacted with methyl vinyl ketone (see Francis A. Carey, in *Advanced Organic Chemistry*, Part A, Chapter 5.6 for examples), in an aprotic solvent such as toluene. The intermediates of formula XX may be ring closed or ring opened as illustrated below.

tection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The subject invention also includes isotopically-labelled compounds, which are identical to those recited in Formula

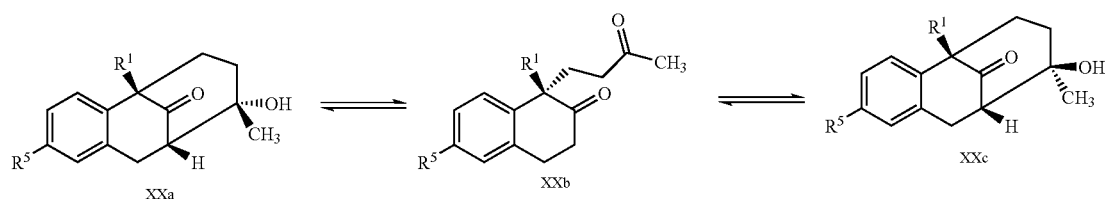

Alternatively, the racemic compound of formula XX is prepared by reaction of a compound of formula XXI with methyl vinyl ketone and a base, such as sodium methoxide or KOH, in a solvent, such as methanol. This reaction may also give directly a racemic mixture of the products of formula XVII, which mixtures may be resolved by chiral HPLC or by other literature methods.

The compound of formula XXI can be prepared by reaction of a compound of the formula XXIII with a nitrogen-containing base (NCB), such as pyrrolidine, piperidine or morpholine, at a refluxing temperature in an aprotic solvent such as toluene, benzene, dichloromethane or dioxane, to form an intermediate of the formula XXII, wherein NCB is a nitrogen containing base. The intermediate of formula XXII can then be reacted with the alkylating agent of formula $R^1$-L wherein $R^1$ is as defined above except that $R^1$ cannot have a double bond connected directly to L and L is a leaving group (see Francis A. Carey, in *Advanced Organic Chemistry*, Part A, Chapter 5.6 for examples) in dioxane, methanol, ethanol, isopropanol, DMF, DMSO or THF. Typical alkylating agents are primary, secondary, benzylic or allylic halides and are preferably alkyl bromides or alkyl iodides.

Alternatively, the compound of formula XXI can be prepared from a compound of formula XXIII by conversion of the compound of formula XXIII to its anion with a strong base, such as sodium hydride, sodium methoxide, lithium diisopropylamide, lithium bis(trimethylsilyl)amide, potassium bis(trimethylsilyl)amide, potassium t-butoxide or others, in an aprotic solvent, such as dimethylformamide (DMF) or tetrahydrofuran (THF). This reaction is conducted at −78° C. to room temperature depending on the nature of the base used. The resulting anion is alkylated with the appropriate alkylating agent of formula $R^1$-L as defined previously.

The compound of formula XXIII can be prepared by methods known to those skilled in the art. Specifically, a compound of the formula XXIII (wherein $R^5$ is halogen, hydrogen, methyl ether, or benzyl ether) can be prepared as described in Org. Syn. 1971, 51, 109–112.

Some of the preparation methods useful for the preparation of the compounds described herein may require pro- I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^5$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

In addition, when the active compounds and prodrugs form hydrates or solvates, they are also within the scope of the present invention.

The active compounds and prodrugs also includes racemates, stereoisomers and mixtures of these compounds, including isotopically-labeled and radio-labeled compounds. Such isomers can be isolated by standard resolution techniques, including fractional crystallization and chiral column chromatography.

For instance, the active compounds have asymmetric carbon atoms and are therefore enantiomers or diastereomers. Diastereomeric mixtures can be separated into their individual diastereomers on the basis of their physical/chemical differences by methods known in the art, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

The following configurations of the active compounds (as represented by simplified structures) are preferred, with the first configuration being more preferred:

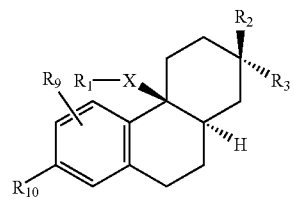

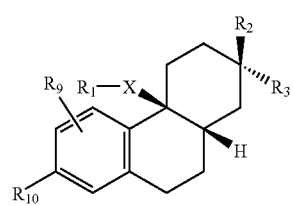

Also, the active compounds and prodrugs can exist in several tautomeric forms, including the enol form, the keto form and mixtures thereof. All such tautomeric forms are included within the scope of the present invention. Tautomers exist as mixtures of tautomers in solution. In solid form, usually one tautomer predominates. Even though one tautomer may be described the present invention includes all tautomers of the active compounds.

The GR agonists of the present invention can be used to influence the basic, life sustaining systems of the body, including carbohydrate, protein and lipid metabolism, electrolyte and water balance, and the functions of the cardiovascular, kidney, central nervous, immune, skeletal muscle and other organ and tissue systems. In this regard, GR agonists are useful for the treatment of diseases associated with an excess or a deficiency of glucocorticoids in the body. As such, they may be used to treat the following: obesity, diabetes, gastrointestinal diseases, cardiovascular disease, hypertension, hematologic diseases, neoplastic diseases, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, edematous states, inflammatory diseases (such as osteoarthritis, rheumatoid arthritis, psoriatic arthritis, ankylosing spondylitis, asthma and rhinitis), collagen diseases, tests of adrenal function, viral infection, immunodeficiency, immunomodulation, autoimmune diseases, endocrine disorders, allergies, wound healing, dermatological disorders, ophthalmic diseases, compulsive behavior, multi-drug resistance, addiction, psychosis, anorexia, cachexia, post-traumatic stress syndrome, post-surgical bone fracture, medical catabolism and prevention of muscle frailty.

Furthermore, it will be understood by those skilled in the art that the active compounds, isomers, prodrugs and pharmaceutically acceptable salts thereof including pharmaceutical compositions and formulations containing these compounds, isomers, prodrugs and salts can be used in a wide variety of combination therapies to treat the conditions and diseases described above. Thus, the compounds, isomers, prodrugs and pharmaceutically acceptable salts thereof of the present invention can be used in conjunction with other pharmaceutical agents for the treatment of the disease/conditions described herein.

For instance, glucocorticoid receptor agonists are efficacious agents for the treatment of various inflammatory diseases; however, treatment is often accompanied by undesirable side effects. These side effects include, but are not limited to, the following examples: metabolic effects, weight gain, muscle wasting, decalcification of the skeleton, osteoporosis, thinning of the skin and thinning of the skeleton. However, according to the present invention, glucocorticoid receptor agonists may be used in combination with certain nonsteroidal compounds, such as 5H-chromeno[3,4-f]quinolines, which are selective modulators of steroid receptors, as disclosed in U.S. Pat. No. 5,696,127; and certain steroid compounds substituted at position 10, which possess antiglucocorticoid activity, and some of which have glucocorticoid activity, as disclosed in Published European Patent Application 0 188 396, published 23 Jul. 1986. Examples of glucocorticoid receptor agonists include those known in the art, such as prednisone (17,21-dihydroxypregnane-1,4-diene-3,11,20-trione), prednylidene ((11β)-11,17,21-trihydroxy-16-methylenepregna-1,4-diene-3,20-dione), prednisolone ((11β)-11,17,21-trihydroxypregna-1,4-diene-3,20-dione), cortisone (17α,21-dihydroxy-4-pregnene-3,11,20-trione), dexamethasone ((11β,16α)-9-fluoro-11,17,21-trihydroxy-16-methylpregna-1,4-diene-3,20-dione), and hydrocortisone (11β,17α,21-trihydroxypregn-4-ene-3,20-dione). These compounds, which are glucocorticoid receptor agonists, will generally be administered in the form of a dosage unit at a therapeutically effective amount of such compound. For example, prednisone or an equivalent drug may be administered from about 5 to about 80 mg, depending on the condition; hydrocortisone may be administered from about 100 to about 400 mg, depending on the condition; and dexamethasone may be administered from about 4 to about 16 mg, depending on the condition. These doses are typically administered once to twice daily, and for maintenance purposes, sometimes on alternate days.

In combination therapy treatment, both the compounds of this invention and the other drug therapies are administered to mammals (e.g., humans, male or female) by conventional methods. As recognized by those skilled in the art, the therapeutically effective amounts of the compounds of this invention and the other drug therapies to be administered to a patient in combination therapy treatment will depend upon a number of factors, including, without limitation, the biological activity desired, the condition of the patient, and tolerance for the drug.

As noted above, the compounds, isomers, prodrugs and pharmaceutically acceptable salts of the present invention can be combined in a mixture with a pharmaceutically acceptable carrier, vehicle or diluent to provide pharmaceutical compositions useful for treating the biological conditions or disorders noted herein in mammalian, and more preferably, in human, patients. The particular carrier, vehicle or diluent employed in these pharmaceutical compositions may take a wide variety of forms depending upon the type of administration desired, for example, intravenous, oral, topical, buccal, suppository or parenteral. Also, the compounds, isomers, prodrugs and salts thereof of this invention can be administered individually or together in any conventional dosage form, such as an oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds, prodrugs and pharmaceutically acceptable salts thereof of this invention can be combined with various sweetening agents, flavoring agents, coloring agents, emulsifying agents and/or suspending agents, as well as such diluents as water, ethanol, propylene glycol, glycerin and various like combinations thereof.

Due to their ease of administration, tablets and capsules represent the most advantageous oral dosage form for the pharmaceutical compositions of the present invention.

As with the other routes of administration and corresponding dosage forms described herein, dosage forms intended for oral administration are also suitably formulated to provide controlled-, sustained-, and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms would include sustained-release oral tablets, capsules, and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For aerosol formulations for treatment of the conditions referred to above (eg., asthma) in the average adult human are preferably arranged so that each metered dose or "puff" of aerosol contains 1 mg to 1000 mg of the compound of the invention, preferably 1–10 mg. The overall daily dose with an aerosol will be within the range 10 mg to 100 mg. Administration may be several times daily, for example 2, 3, 4 or 8 times, giving for example, 1, 2 or 3 doses each time.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

The pharmaceutical compositions and compounds, isomers, prodrugs and pharmaceutically acceptable salts thereof of the active compounds for treatment of the methods of the present invention will generally be administered in the form of a dosage unit (e.g., tablet, capsule, etc.) at a therapeutically effective amount of such compound, prodrug or salt thereof from about 0.1 µg/kg of body weight to about 500 mg/kg of body weight, more particularly from about 1 µg/kg to about 250 mg/kg, and most particularly from about 2 µg/kg to about 100 mg/kg. More preferably, an active compound will be administered at an amount of about 0.1 mg/kg to about 500 mg/kg of body weight, and most preferably from about 0.1 mg/kg to about 50 mg/kg of body weight. As recognized by those skilled in the art, the particular quantity of pharmaceutical composition administered to a patient will depend upon a number of factors, including, without limitation, the biological activity desired, the condition of the patient, and tolerance for the drug.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of formula I, an isomer thereof, a prodrug thereof or a salt of such compound, isomer or prodrug and a second compound as described above. The kit comprises a container, such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also, a daily dose of formula I compound (or an isomer, prodrug or pharmaceutically acceptable salt thereof) can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following paragraphs describe exemplary formulations, dosages etc. useful for non-human animals. The administration of compounds of this invention can be effected orally or non-orally, for example by injection. An amount of a compound of formula I, an isomer, prodrug or pharmaceutically acceptable salt thereof, is administered such that a therapeutically effective dose is received, generally a daily dose which, when administered orally to an animal is usually between 0.01 and 500 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

The present invention has several advantageous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred feed of domestic pets, such as cats and dogs, usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of a compound of the present invention to provide the animal with 0.01 to 500 mg/kg/day of body weight of the active ingredient. The preferred dosage for poultry, swine, cattle, sheep, goats and domestic pets is in the range of from 0.1 to 50 mg/kg/day of body weight of active ingredient.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

The activity of the compounds of the present invention are demonstrated by one or more of the assays described below:

The following is a description of an assay for the identification of glucocorticoid receptor antagonists/agonists: SW 1353 human chondrosarcoma cells containing endogenous human glucocorticoid receptors are transfected with a 3×GRE-luciferase plasmid generated by standard procedures and a plasmid conferring neomycin resistance. Novel glucocorticoid responsive cell lines are generated and characterized. One such cell line designated SW 1353 human chondrosarcoma is used for determining the activity of compounds at the glucocorticoid receptor. Cells are maintained in charcoal-stripped serum and transferred to 96-well microtiter plates one day prior to treatment with various concentrations ($10^{-12}$ to $10^{-5}$) of test compounds in the absence (for agonists) and presence (for antagonists) of known glucocorticoid receptor agonists (i.e., dexamethasone, hydrocortisone) for up to 24 hours. Treatments are performed in triplicate. Cell lysates are prepared and luciferase activity is determined using a luminometer. Agonist activity is assessed by comparing the luciferase activity from cells treated with test compound to cells treated with the agonist dexamethasone. Antagonist activity is assessed by comparing the luciferase activity of an $EC_{50}$ concentration of dexamethasone in the absence and presence of test compound. The $EC_{50}$ (concentration that produced 50% of the maximal response) for dexamethasone is calculated from dose response curves.

The following is a description of an assay for determining the competitive inhibition binding of the Human Type II Glucocorticoid receptor expressed in Sf9 cells:

Binding protocol: Compounds are tested in a binding displacement assay using human glucocorticoid receptor expressed in Sf9 cells with $^3$H-dexamethasone as the ligand. Human glucocorticoid receptor is expressed in Sf9 cells as described in Mol. Endocrinology 4: 209, 1990. Pellets containing Sf9 cells expressing the human GR receptor from 1 L vats are lysed with 40 ul of 20 mM AEBSF stock (Calbiochem, LaJolla, Calif.) containing 50 mg/ml leupeptin and 40 ml of homogenization buffer is added. The assay is carried out in 96-well polypropylene plates in a final volume of 130 ul containing 200 ug Sf9 lysate protein, 6.9 nM $^3$H-dexamethasone (Amersham, Arlington Heights, Ill.) in presence of test compounds, test compound vehicle (for total counts) or excess dexamethasone (7 uM non-radioactive, to determine non-specific binding) in an appropriate volume of assay buffer. All compounds are tested at 6 concentrations in duplicate (concentration range 0.1–30 nM or 3–1000 nM). Test compounds are diluted from a 25 mM stock in 100% DMSO with 70% EtOH and added in a volume of 2 μl. Once all additions are made the plates are shaken, sealed with sealing tape and incubated at 4° C. overnight.

After the overnight incubation, unbound counts are removed with dextran coated charcoal as follows: 75 μl of dextran coated charcoal (5.0 g activated charcoal, 0.5 g dextran adjusted to volume of 100 ml with assay buffer) is added, plates are shaken and incubated for five minutes at 4° C. Plates are then centrifuged in a refrigerated benchtop centrifuge at top speed for 15 minutes. 100 μl of the supernatant from each well is placed into a 96-well PET plate with 200 μl of scintillation cocktail and counted on a beta counter (1450 MicroBetaTrilux, from Wallac, Turku, Finland).

Data analysis: After subtracting non-specific binding, counts bound are expressed as % of total counts. The concentration response for test compounds are fitted to a sigmoidal curve to determine the IC50 (concentration of compound that displaces 50% of the bound counts).

Reagents: Assay Buffer: 2.0 ml 1M Tris, 0.2 ml 0.5 mM EDTA, 77.1 mg DTT, 0.243 g sodium molybdate in a volume of 100 ml water; Homogenization buffer: 2.0 ml 0.5 M $K_2HPO_4$ (pH 7.6), 20 µl 0.5 M EDTA (pH 8.0), 77.1 mg DTT, 0.486 g sodium molybdate in a volume of 100 ml water.

The following is a description of an assay for determining receptor selectivity: T47D cells from ATCC containing endogenous human progesterone and mineralocorticoid receptors are transiently transfected with a 3×GRE-luciferase using Lipofectamine Plus (GIBCO-DRL, Gaithersburg, Md.). Twenty-four hours post-transfection cells are maintained in charcoal-stripped serum and transferred to 96-well microtiter plates. The next day cells are treated with various concentrations ($10^{-12}$ to $10^{-5}$) of test compounds in the absence and presence of a known progesterone receptor agonist (progesterone) and a known mineralocorticoid receptor agonist (aldosterone) for up to 24 hours. Treatments are performed in triplicate. Cell lysates are prepared and luciferase activity is determined using a luminometer. Agonist activity is assessed by comparing the luciferase activity from cells treated with compound alone to cells treated with either the agonist progesterone or aldosterone. Antagonist activity is assessed by comparing the luciferase activity of an $EC_{50}$ concentration of progesterone or aldosterone in the absence and presence of compound. The $EC_{50}$ (concentration that produced 50% of maximal response) for progesterone and aldosterone is calculated from dose response curves.

The following is a description of an assay for determining the ability of a compound to inhibit glucocorticoid agonist induction of liver tyrosine amino transferase (TAT) activity in conscious rats:

Animals: Male Sprague Dawley rats (from Charles River, Wilimington Mass.) (adrenal-intact or adrenalectomized at least one week prior to the screen) b.w. 90 g are used. The rats are housed under standard conditions for 7–10d prior to use in the screen.

Experimental protocol: Rats (usually 3 per treatment group) are dosed with test compound, vehicle or positive control (Ru486) either i.p., p.o., s.c. or i.v. (tail vein). The dosing vehicle for the test compounds is typically one of the following: 100% PEG 400, 0.25% methyl cellulose in water, 70% ethanol or 0.1 N HCl and the compounds are tested at doses ranging from 10 to 125 mg/kg. The compounds are dosed in a volume of 1.0 ml/100 g body weight (for p.o.) or 0.1 ml/100 g body weight for other routes of administration. Ten minutes after the administration of the test compound, the rats are injected with dexamethasone (0.03 mg/kg i.p. in a volume of 0.1 ml/100 g) or vehicle. To prepare the dexamethasone dosing solution, dexamethasone (from Sigma, St. Louis, Mo.) is dissolved in 100% ethanol and diluted with water (final: 10% ethanol:90% water, vol:vol). Groups treated with vehicle-vehicle, vehicle-dexamethasone, and Ru486-dexamethasone are included in each screen. The compounds are tested vs. dexamethasone only. Three hours after the injection of dexamethasone the rats are sacrificed by decapitation. A sample of liver (0.3 g) is excised and placed in 2.7 ml of ice cold buffer and homogenized with a polytron. To obtain cytosol the liver homogenate is centrifuged at 105,000 g for 60 min and the supernatant is stored at −80° C. until analysis. TAT is assayed on 100 ul of a 1:20 dilution of the 105,000 g supernatant using the method of Granner and Tomkins (Methods in Enzymology 17A: 633–637, 1970) and a reaction time of 8–10 minutes. TAT activity is expressed as umol product/min/g liver.

Interpretation: Treatment data are analyzed by using analysis of variance (ANOVA) with protected least significant difference (PLSD) post-hoc analysis. Compounds are considered active in this test if the TAT activity in the group pretreated with compound prior to dexamethasone administration is significantly (P<0.05) decreased relative to the TAT activity in the vehicle-dexamethasone treated group.

The following is a description of an assay for determining the effect of a compound on two typical genes that are upregulated during an inflammatory response. This assay, the glucocorticoid inhibition of IL-1 (Interleukin-1) induced MMP-1 (Matrix Metalloproteinase-1) and IL-8 (Interleukin-8) production in human chondrosarcoma cells, is conducted as follows: SW1353 human chondrosarcoma cells (obtained from ATCC) from passage 12 through passage 19 are used in a 96 well format assay. Cells are plated at confluence into 96 well plates in DMEM (Dulbecco's Modified Eagle Medium) with 10% fetal bovine serum and incubated at 37° C., 5% $CO_2$. After 24 hours, serum containing media is removed and replaced with 200 ul/well DMEM containing 1 mg/L insulin, 2 g/L lactalbumin hydrosylate, and 0.5 mg/L ascorbic acid and returned to incubation at 37° C., 5% $CO_2$. The following morning, the serum free media is removed and replaced with 150 ul/well fresh serum free media containing +/−20 ng/ml IL-1 beta, +/−5 nM dexamethasone, +/− compound. All conditions are completed in triplicate using only the inner 60 wells of the 96 well plate. Outside surrounding wells of plate contain 200 ul of serum free DMEM. Plates are incubated at 37° C., 5% $CO_2$. At 24 hours after addition of IL-1, 25 ul of sample from each well is removed under aseptic conditions for IL-8 production analysis. Samples are stored at −20° C. until time of analysis. IL-8 production is assessed using the Quantikine human IL-8 ELISA kit from R&D Systems (D8050) on samples diluted 60-fold in RD5P Calibrator Diluent, following the manufacturer's protocol. The percent of the average IL-1 control is determined for the average of each of the triplicate samples following subtraction of the average signal from untreated cells. $IC_{50}$'s are determined from log linear plots of the percent of control versus the concentration of inhibitor. At 72 hours after IL-1 addition, the remaining media is removed and stored at −20° C. until time of MMP-1 production analysis. MMP-1 production is assessed via the Bio-Trak MMP-1 ELISA kit from Amersham (RPN2610) on 100 ul of neat sample following the manufacturer's protocol.

The percent of the average IL-1 control is determined for the average of each of the triplicate samples following subtraction of the average signal from untreated cells. $IC_{50}$'s are determined from log linear plots of the percent of control versus the concentration of inhibitor. Dexamethasone has proven to be a good positive control inhibitor of both IL-8 and MMP1 expression ($IC_{50}$=5 nM).

Active compounds are defined as those compounds with: 1) an $ED_{50}$ of less than 3 µM in the SW 1353 chondrosarcoma GRE luciferase assay; 2) comparatively less than 50% of the maximal activation of dexamethasone at 100 nM in the SW 1353 chondrosarcoma GRE luciferase assay; 3) an average $IC_{50}$ of less than 3 µM in the IL-8 and MMP-13 production assays; or 4) comparatively greater than 50% of the maximal inhibition of dexamethasone at 100 nM in the IL-8 and MMP-13 production assays.

More preferred active compounds are defined as those compounds with: 1) an $ED_{50}$ of less than 3 µM in the SW 1353 chondrosarcoma GRE luciferase assay; 2) comparatively less than 40% of the maximal activation of dexamethasone at 100 nM in the SW 1353 chondrosarcoma GRE luciferase assay; 3) an average $IC_{50}$ of less than 3 µM in the IL-8 and MMP-13 production assays; or 4) comparatively greater than 60% of the maximal inhibition of dexamethasone at 100 nM in the IL-8 and MMP-13 production assays.

Even more preferred active compounds are defined as those compounds with: 1) an $ED_{50}$ of less than 3 µM in the SW 1353 chondrosarcoma GRE luciferase assay; 2) comparatively less than 30% of the maximal activation of dexamethasone at 100 nM in the SW 1353 chondrosarcoma GRE luciferase assay; 3) an average $IC_{50}$ of less than 3 µM in the IL-8 and MMP-13 production assays; or 4) comparatively greater than 70% of the maximal inhibition of dexamethasone at 100 nM in the IL-8 and MMP-13 production assays.

Even more preferred active compounds are defined as those compounds with: 1) an $ED_{50}$ of less than 3 µM in the SW 1353 chondrosarcoma GRE luciferase assay; 2) comparatively less than 20% of the maximal activation of dexamethasone at 100 nM in the SW 1353 chondrosarcoma GRE luciferase assay; 3) an average $IC_{50}$ of less than 3 µM in the IL-8 and MMP-13 production assays; or 4) comparatively greater than 80% of the maximal inhibition of dexamethasone at 100 nM in the IL-8 and MMP-13 production assays.

Another embodiment of the invention is directed to those active compounds defined as those compounds with comparatively less than 10% of the maximal activation of dexamethasone at 100 nM in the SW 1353 chondrosarcoma GRE luciferase assay.

Another embodiment of the invention is directed to those active compounds defined as those compounds with comparatively less than 5% of the maximal activation of dexamethasone at 100 nM in the SW 1353 chondrosarcoma GRE luciferase assay.

Other preferred active compounds are defined as those compounds with comparatively greater than 80% of the maximal inhibition of dexamethasone at 100 nM in the IL-8 and MMP-13 production assays.

Other preferred active compounds are defined as those compounds with comparatively greater than 90% of the maximal inhibition of dexamethasone at 100 nM in the IL-8 and MMP-13 production assays.

Other preferred active compounds are defined as those compounds with comparatively greater than 100% of the maximal inhibition of dexamethasone at 100 nM in the IL-8 and MMP-13 production assays.

Another embodiment of the invention is directed to those active compounds defined as those compounds with comparatively greater than 110% of the maximal inhibition of dexamethasone at 100 nM in the IL-8 and MMP-13 production assays.

EXAMPLES

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Atmospheric pressure chemical ionization mass spectra ($AP_c1$) and electrospray ionization (ESI) mass spectra were obtained on a Micromass ZMD spectrometer (carrier gas: nitrogen, available from Micromass Ltd., Manchester, UK) Commercial reagents were utilized without further purification. THF refers to tetrahydrofuran. DMF refers to N,N-dimethylformamide. Flash chromatography was performed with either Baker™ silica gel (40 µm; J. T. Baker, Phillipsburg, N.J.) or silica Gel 50 (EM Sciences™, Gibbstown, N.J.) in glass columns or in Flash 12 and 40 Biotage™ columns (Cyax Corp., Charlottesville, Va.) under low pressure. Purification of compounds by HPLC was performed on Waters Symmetry C-8 19 mm×50 mm or 30 mm×50 mm columns, using as eluant various mixtures of acetonitrile and water (each containing 0.1% formic acid) at a flow rate of 25 mL/minute. Room or ambient temperature refers to 20–25° C. All non-aqueous reactions were run under a nitrogen atmosphere for convenience and to maximize yields. Concentration at reduced pressure or in vacuo means that a rotary evaporator was used.

Preparation 1a

1-Ethyl-6-methoxy-3,4-dihydro-1H-naphthalen-2-one

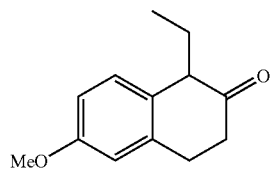

A solution of 6-methoxy-2-tetralone (120.55 grams, 0.684 mol) and pyrrolidine (61 mL, 0.685 mol) in toluene (1.7 L) was heated to reflux using a Dean-Stark trap apparatus for 3 hours. After removal of the azeotroped water, the reaction mixture was cooled to room temperature and concentrated to a solid. To this solid was added methanol (1.2 L) and ethyl iodide (121 mL, 1.51 mol). The resulting solution was heated at reflux overnight and then concentrated under vacuum to remove methanol. A solution of acetic acid (120 mL), sodium acetate (120 g) in water (240 mL) was added to the residue and the resultant mixture was heated at reflux for 2 hours. After cooling, the mixture was extracted several times with diethyl ether. The combined organic layers were washed twice with aqueous 1M HCl, twice with aqueous 1M NaOH and once with brine. After drying over magnesium sulfate, the solvent was evaporated to afford the title compound as an oil, 121.8 grams. Mass spectrum: m/e 204.

Preparation 1b (1S,9S)-Ethyl-10-hydroxy-5-methoxy-10-methyl-tricyclo[7.3.1.0$^{2,7}$]trideca-2,4,6-trien-13-one

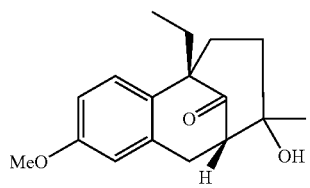

A solution of the title product of Preparation 1a (121.8 grams, 0.592 mol) and freshly distilled (S)-(−)-alpha-methyl benzylamine (72 grams, 0.592 mol) in toluene (600 mL) was heated at reflux using a Dean-Stark trap apparatus overnight. After removal of the azeotroped water, some of the toluene (about 300 mL) was distilled off. Freshly distilled methylvinylketone (4.39 grams, 0.626 mol) was added dropwise to the solution. The solution was stirred at room temperature for 2 hours and then heated in an oil bath at 45° C. overnight. The reaction solution was cooled in an ice bath and aqueous 10% sulfuric acid was added. After stirring at room temperature for 2 days, the solution was extracted three times with ethyl acetate (EtOAc). The combined organic layers were washed with water and brine. After drying over magnesium sulfate, the solvent was evaporated to afford an oil. The title compound (59.6 grams) was isolated from this oil by flash chromatography eluting with 15% ethyl acetate in hexane followed by 21% ethyl acetate in hexane. Mass spectrum: m/e 275 (M+1).

Preparation 1c (4aR)-4a-Ethyl-7-methoxy-4,4a9,10-tetrahydro-3H-phenanthren-2-one

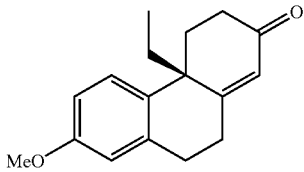

A solution of 59.6 grams (0.217 mol) of the title product of Preparation 1b in methanol (300 mL) was added dropwise to 1M sodium methoxide in methanol (250 mL). The mixture was heated at reflux for 3 hours. After cooling to room temperature, acetic acid was added to give a neutral pH and the mixture was concentrated under vacuum. The residue was dissolved in ethyl acetate and washed sequentially with aqueous saturated NaHCO$_3$, water and brine. After drying over magnesium sulfate, the solvent was evaporated to afford the title compound as a tan solid, 55 grams. Mass spectrum: 257 (M+1).

Preparation 1d (4aR)-4a-Ethyl-7-hydroxy-4,4a,9,10-tetrahydro-3H-phenanthren-2-one

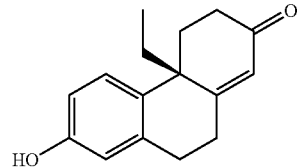

To a well stirred solution of the title product of Preparation 1c (55 grams, 0.214 mol) in methanesulfonic acid (890 mL) was added in portions D,L-methionine (106.7 grams, 0.715 mol). The mixture was stirred overnight at room temperature, then poured into excess ice and stirred for an additional 30 minutes. The precipitated solid was collected by filtration and subsequently dissolved in ethyl acetate. The resultant solution was washed with aqueous saturated sodium bicarbonate (NaHCO$_3$) and brine. After drying over magnesium sulfate, the solvent was evaporated under vacuum to afford a red semi-solid. This semi-solid was triturated with diethyl ether to afford the title compound as a yellow solid (34 grams) which was collected by filtration. $^1$H NMR (CDCl$_3$) δ 7.14 (d, J=8.3 Hz, 1 H), 6.76 (dd, J=2.6, 8.3 Hz, 1 H), 6.62 (d, J=2.6 Hz, 1 H), 5.97 (s, 1 H), 3.00–2.95 (m, 1 H), 2.86–2.38 (series of m, total 6 H), 2.08–1.90 (m, 3 H), 0.84 (t, J=7.3 Hz, 3 H).

Preparation 1e 4a-(R)-Ethyl-7-hydroxy-3,4,4a,9-tetrahydro-1H-phenanthren-2-one ethylene ketal

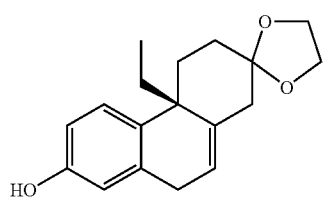

A mixture of the title product of Preparation 1d (3.00 grams, 12.38 mmol), ethylene glycol (3.45 mL, 61.90 mmol), p-toluenesulfonic acid monohydrate (0.24 grams, 1.24 mmol) and toluene (240 mL) was heated to reflux for 16 hours using a Dean-Stark apparatus. The mixture was cooled to room temperature and poured over 250 mL of saturated aqueous sodium bicarbonate. The aqueous layer was separated and extracted with ethyl acetate (250 mL). The combined organic layers were washed with 100 mL brine (100 mL), dried (K$_2$CO$_3$), and concentrated to afford the title compound as a low-melting solid, 3.70 grams. Mass spectrum: (m/e) 287.4 (M$^+$+1, +ion).

Preparation 1f (4aR,10aR)-4a-ethyl-7-hydroxy-3,4,4a,9.10,10a-hexahydro-1H-phenanthren-2-one

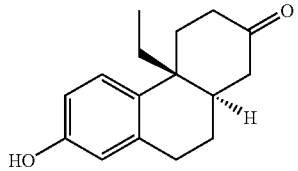

Into a Parr bottle was placed palladium hydroxide on carbon (20 wt. % Pd, 1.8 grams), which was then washed with two portions of acetone (30 mL each) followed by two portions of toluene (30 mL each). To the dry catalyst was added the compound of Preparation 1e (3.70 grams, 12.38 mmol) suspended in toluene (220 mL), and the mixture was hydrogenated at 70° C. for 16 hours. The mixture was cooled to room temperature, filtered, and concentrated to yield 3.93 g of a white foam.

The foam was dissolved in tetrahydrofuran (30 mL), treated with aqueous 1 M hydrochloric acid solution (30 mL), and stirred at room temperature for 4.5 hours. The tetrahydrofuran was removed by rotary evaporation. The aqueous residue was diluted with water (40 mL), and extracted with ethyl acetate (2×50 mL). The combined ethyl acetate extracts were washed with saturated aqueous NaHCO$_3$ (30 mL) and brine (30 mL), dried (MgSO$_4$), and concentrated. The residue was partially dissolved in 20% ethyl acetate/hexanes and filtered to afford a small amount (0.11 g) of the title compound as a colorless solid. The filtrate was purified by flash chromatography using 20% ethyl acetate in hexanes as eluant to afford an additional 2.55 g of the title compound contaminated with 21% of the cis diastereomer. In a separate run, 382 mg of this material was recrystallized from toluene to give 270 mg of the title compound, melting point 167.5–169.5° C., containing greater than 90% of the trans diastereomer. An analytical sample was prepared by recrystallization from 5% ethyl acetate/hexane. Melting point: 169–171° C. Mass spectrum: (m/e) 245.3 (M$^+$+1, +ion). $^1$H NMR (CDCl$_3$): δ 7.11 (d, J=8.3 Hz, 1 H), 6.65–6.60 (m, 2 H), 2.93–2.90 (m, 2 H), 2.71–2.70 (m, 1 H), 2.50–1.50 (m, 10 H), 0.81 (t, J=7.8 Hz, 3 H). Analytical calculated for C$_{16}$H$_{20}$O$_2$: C, 78.65; H, 8.25. Found: C, 78.70; H, 8.37.

Preparation 2a (4aR)-4a-allyl-7-hydroxy-4,4a,9,10-tetrahydro-3H-phenanthren-2-one

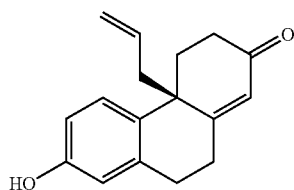

(4aR)-4a-allyl-7-methoxy-4,4a,9,10-tetrahydro-3H-phenanthren-2-one was prepared in three steps from 6-methoxy-2-tetralone and allyl bromide in a manner analogous to that described for the synthesis of (4aR)-4a-ethyl-7-methoxy-4,4a,9,10-tetrahydro-3H-phenanthren-2-one in Preparations 1a to 1c.

To a solution of (4aR)-4a-allyl-7-methoxy-4,4a,9,10-tetrahydro-3H-phenanthren-2-one (15.0 grams, 55.9 mmol) in methylene chloride (350 mL) at −78° C. was added dropwise boron tribromide (10.6 mL, 112 mmol). The mixture was allowed to warm to 0° C. over 5 hours and was then poured onto a mixture of ice and water. Solid sodium bicarbonate was carefully added to neutralize the mixture which was then extracted with ethyl acetate. After washing with brine, the organic extract was dried (MgSO$_4$) and concentrated under vacuum. The title compound (11.0 grams, 53%) was isolated by flash chromatography eluting with 5 to 10% ethyl acetate in methylene chloride. $^1$H NMR (CDCl$_3$): δ 7.14 (d, J=8.5 Hz, 1 H), 6.72 (dd, J=2.7, 8.5 Hz, 1 H), 6.58 (d, J=2.7 Hz, 1 H), 5.94 (s, 1 H), 5.62–5.54 (m, 1 H), 5.03–4.98 (m, 2 H), 4.85 (br s, 1 H), 2.95–2.91 (m, 1 H), 2.85–2.63 (m, 5 H), 2.53–2.40 (m, 3 H), 2.08–1.99 (m, 1 H).

Preparation 2b (4aR,10aR)-4a-allyl-7-hydroxy-3,4,4a,9,10,10a-hexahydro-1H-phenanthren-2-one

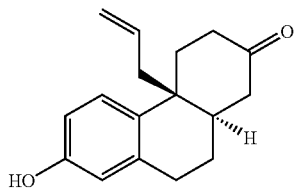

A three neck round bottom flask was equipped a dry ice reflux condenser and a mechanical stirrer. Ammonia (400 mL) was condensed into the flask while cooling in a dry ice/acetone bath at −78° C. To this flask was added approximately 0.08 grams. (11.5 mmol) of lithium wire to obtain a dark blue solution. A solution of the title product of Preparation 2a (10.5 grams, 41.3 mmol) in tetrahydrofuran (100 mL) was added to the mixture slowly in order to keep the reaction dark blue. Just before dissipation of the blue color was anticipated, more lithium wire (about 0.08 grams, 11.5 mmol) was added to the mixture to maintain the blue color. This was repeated until the a total amount of 0.6 grams (86.5 mmol lithium had been added. After addition of the enone was complete, the reaction was stirred an additional 30 minutes. The reaction was quenched by dropwise addition of excess aqueous ammonium chloride solution, which was accompanied by the dissipation of the blue color. The mixture was allowed to warm to room temperature and the ammonia was allowed to evaporate. The residue was taken up in water and extracted twice with ethyl acetate. The combined organic layers were washed with brine, dried (MgSO$_4$) and concentrated. The crude product was triturated with diethyl ether to afford the title compound as a tan solid (5.22 grams, 49%) which was collected by filtration. $^1$H NMR (CDCl$_3$): δ 7.05 (d, J=8.3 Hz, 1 H), 6.62–6.58 (m, 2 H), 5.72–5.62 (m, 1 H), 5.08–5.01 (m, 2 H), 4.73 (br s, 1 H), 2.91–2.88 (m, 2H), 2.63–2.28 (m, 7 H), 2.11–2.03 (m, 1 H), 1.95–1.84 (m, 1 H), 1.66–1.56 (m, 2 H).

Preparation 3a (3S,4aR,10aR)-3-Bromo-4a-ethyl-7-hydroxy-3,4,4a,9,10,10a-hexahydro-1H-phenanthren-2-one

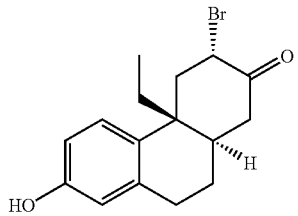

To a solution of the title compound of Preparation 1f (5.4 grams, 22.1 mmol) in tetrahydrofuran (500 mL) at −78° C. was added phenyltrimethylammonium bromide tribromide (8.31 grams, 22.1 mmol) in portions. The mixture was allowed to stir at −78° C. for 1 hour and then allowed to slowly warm to 0° C. over 1.5 hours. After stirring at 0° C.

for a further 3 hours, the mixture was poured into water and extracted twice with ethyl acetate. The combined extracts were dried (MgSO$_4$) and concentrated to give an orange oil that was passed through a pad of silica gel washing with ethyl acetate. Concentration provided crude title product as an orange foam. $^1$H NMR (CDCl$_3$) selected signals: δ 4.78 (dd, J=5.7, 13.5 Hz, 1 H), 3.28 (dd, J=5.7, 13.0 Hz, 1 H), 2.94–2.91 (m, 2 H).

Preparation 3b (3S,4aR,10aR)-4a-Ethyl-3,7-dihydroxy-3,4,4a,9,10, 10a-hexahydro-1H-phenanthren-2-one and (2S,4aR, 10aR)-4a-ethyl-2,7-dihydroxy-1,4,4a,9,10,10a-hexahydro-2H-phenanthren-3-one

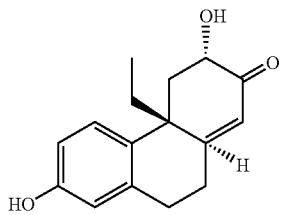

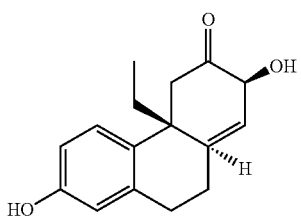

The crude bromide of Preparation 3a (entire sample) was dissolved in cold N,N-dimethylformamide (250 mL) and cold water (50 mL). While the mixture was cooling in an ice bath, aqueous 1 N sodium hydroxide solution was added slowly. The mixture was allowed to stir at 0° C. for 3 hours at which time the mixture was poured into cold aqueous 0.2 M hydrochloric acid solution. The mixture was extracted three times with a 2:1 mixture of ethyl acetate and benzene. The combined extracts were washed with brine, dried (MgSO$_4$), and carefully concentrated under vacuum, not allowing the temperature to exceed 25° C. Most of the remaining N,N-dimethylformamide was removed under high vacuum. A 2:1 mixture of the title compounds (2.21 grams, 39%, 2-keto isomer as major product), was isolated by flash chromatography eluting with a gradient of 20 to 40% ethyl acetate in hexane. Higher temperatures and longer reaction times increased the proportion of the 3-keto isomer in the mixture. Enrichment in either isomer could be achieved by further flash chromatography. 2-Keto isomer: $^1$H NMR (CDCl$_3$) selected signals: δ 4.30 (ddd, J=1.0, 6.7, 12.7 Hz, 1 H), 3.10 (dd, J=6.7, 13.0 Hz, 1 H), 2.93–2.90 (m, 2 H). 3-Keto isomer: $^1$H NMR (CDCl$_3$) selected signals: δ 4.25–4.21 (m, 1 H), 3.29 (d, J=13.0 Hz, 1 H).

Preparation 3c (2S,4aR,10aR)-7-(tert-Butyidimethylsilanyloxy)-4a-ethyl-2-hydroxy-1,4,4a,9,10,10a-hexahydro-2H-phenanthren-3-one

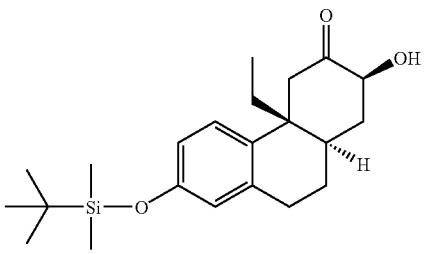

To a solution of the title product mixture of Preparation 3b (542 mg, 2.08 mmol, 3:1 ratio favoring the 3-keto isomer) in methylene chloride was added imidazole (235 mg, 3.5 mmol) and tert-butyldimethylsilyl chloride (420 mg, 2.78 mmol). The mixture was allowed to stir at room temperature overnight. It was then diluted with methylene chloride, washed with 0.5 M aqueous citric acid solution and washed with brine. After drying (MgSO$_4$), concentration afforded an oil from which the title compound (465 mg, 60%) was isolated by flash chromatography eluting with 10% ethyl acetate in hexanes. $^1$H NMR (CDCl$_3$) selected signals: δ 4.25–4.20 (m, 1 H), 3.30 (d, J=13.0 Hz, 1 H), 0.99 (s, 9 H), 0.22 (s, 6 H).

Preparation 3d (2R,4aR,10aR)-2-Benzyl-7-(tert-butyldimethylsilanyloxy)-4a-ethyl-2-hydroxy-1,4,4a,9,10,10a-hexahydro-2H-phenanthren-3-one

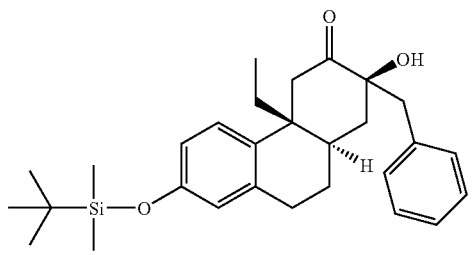

A solution of the title product of Preparation 3c (178 mg, 0.48 mmol) in tetrahydrofuran (5 mL) was cooled to 0° C. and a 1.06 M solution of lithium hexamethyldisilazide in tetrahydrofuran (1 mL, 1.06 mmol) was added. The mixture was allowed to stir at 0° C. for 1.5 hours and then benzyl bromide (0.057 mL, 0.48 mmol) was added. After allowing the reaction to slowly warm to room temperature over 5.5 hours, saturated aqueous ammonium chloride solution was added. The mixture was extracted with diethyl ether and the organic extract was washed with brine, dried (MgSO$_4$) and concentrated to an oil. The title compound (122 mg, 55%) was isolated by flash chromatography eluting with methylene chloride. $^1$H NMR (CDCl$_3$) selected signals: δ 3.27 (d, J=13.3 Hz, 1 H), 3.18 (d, J=13.7 Hz, 1 H), 3.01 (d, J=13.7 Hz, 1 H), 2.67 (d, J=13.3 Hz, 1 H), 2.45–2.38 (m, 1 H), 2.16

(dd, J=3.9, 13.7 Hz, 1 H), 1.88 (apparent t, J=13.7 Hz, 1 H), 1.01 (s, 9 H), 0.73 (t, J=7.3 Hz, 3 H), 0.23 (s, 6 H).

Preparation 3e (2R,4aR,10aR)-2-Benzyl-2,7-dihydroxy-1,4,4a,9,10,10a-hexahydro-2H-phenanthren-3-one

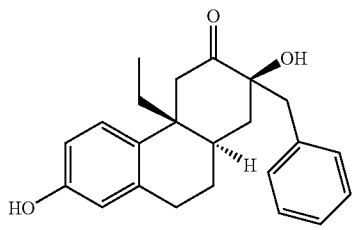

To a solution of the title product of Preparation 3d (83 mg, 0.18 mmol) in tetrahydrofuran at room temperature were added sequentially acetic acid (0.21 mL, 37 mmol) and a 1 M solution of tetrabutylammonium fluoride in tetrahydrofuran (0.7 mL, 0.7 mmol). The mixture was allowed to stir at room temperature for 2 hours and was then passed through a plug of silica gel washing with ethyl acetate. Concentration afforded the title compound (0.63 mg, 100%). $^1$H NMR (CDCl$_3$) selected signals: δ 3.24 (d, J=13.3 Hz, 1 H), 3.15 (d, J=13.7 Hz, 1 H), 2.98 (d, J=13.7 Hz, 1 H), 2.67 (dd, J=1.2, 13.3 Hz, 1 H), 2.43–2.35 (m, 1 H), 2.14 (dd, J=3.7, 13.3 Hz, 1 H), 1.86 (apparent t, J=13.7 Hz, 1 H), 0.71 (t, J=7.3 Hz, 3 H).

Preparation 4a (3E,4aR,10aR)-3-Benzylidene-4a-ethyl-7-hydroxy-3,4,4a,9,10,10a-hexahydro-1H-phenanthren-2-one

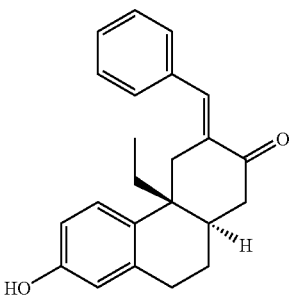

To a solution of the compound of Preparation 1f (0.20 grams, 0.82 mmol) in ethanol (10 mL) was added a 1 M solution of sodium ethoxide in ethanol (2.1 mL, 2.1 mmol). After stirring for 30 minutes, benzaldehyde (0.092 mL, 0.9 mmol) was added. The mixture was stirred overnight and then diluted with water (25 mL). The pH was adjusted to 2 with aqueous 1 M hydrochloric acid solution, and the mixture was extracted with methylene chloride (2×25 mL). The combined organic layers were dried over sodium sulfate, filtered and concentrated to a yellow solid. The solid was triturated with diethyl ether (5 mL) to afford the title compound as a beige solid; 242 mg (89%). Melting point: 265–266° C. Mass spectrum: (m/e) 333 (M$^+$+1, +ion) and 331 (M$^+$–1, –ion). Analytical calculated for C$_{23}$H$_{24}$O$_2$: C, 83.10; H, 7.28. Found: C, 82.83; H, 7.52.

Preparation 4b (2S,3E,4aR,10aR)-3-Benzylidene-4a-ethyl-2-phenyl-1,2,3,4,4a,9,10,10a-octahydrophenanth-2,7-diol

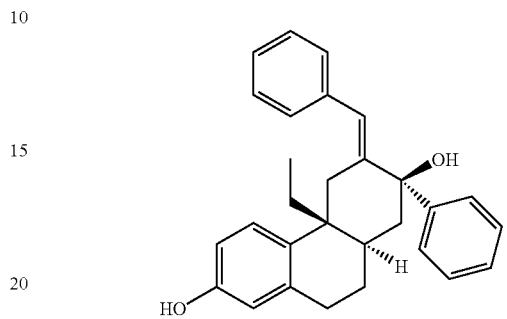

To a suspension of cerium chloride (1.11 grams, 4.5 mmol) in tetrahydrofuran (75 mL) at −78° C. was added a 1 M solution of phenylmagnesium bromide in tetrahydrofuran (4.5 mL, 4.5 mmol). After stirring for 1.5 hours, the compound of Preparation 4a (0.25 grams, 0.75 mmol) was added. After stirring for 2 hours at −40° C., 10% aqueous acetic acid (20 mL) and then water (60 mL) were added. The mixture extracted with ethyl acetate (3×75 mL). The combined organic layers were washed with saturated aqueous sodium bicarbonate solution (30 mL) and brine (30 mL), dried (MgSO$_4$), and concentrated to afford 0.45 g (greater than 100%) of the title compound as a clear oil, which was used in the next step without further purification. Mass spectrum: (m/e) 393 (M$^+$+1–H$_2$O, +ion).

Preparation 4c (2S,3E,4aR,10aR)-70-(4-Nitrobenzoyl)-3-Benzylidene-4a-ethyl-2-phenyl-1,2,3,4,4a,9,10,10a-octahydro-phenanthrene-2-ol

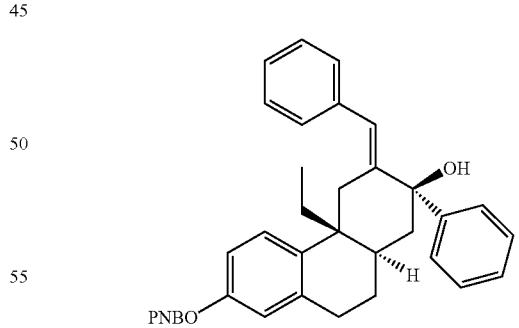

To a solution of the compound of Preparation 4b (0.45 grams, 1.1 mmol) in acetone (15 mL) at 0° C. was added 10% aqueous sodium hydroxide solution (1.31 mL, 1.31 mmol) and 4-nitrobenzoyl chloride (0.243 grams, 1.31 mmol). After 2 hours at room temperature, additional 4-nitrobenzoyl chloride (10 mg, 0.054 mmol) was added and stirring was continued for 1 hour. Saturated aqueous sodium bicarbonate solution (35 mL) was added and the resulting mixture was extracted with ethyl acetate (2×45 mL). The combined organic layers were washed with brine (30 mL), dried (MgSO$_4$), and concentrated to an oil (0.58 grams). The title compound, a foam (0.29 grams, greater than 100%), was isolated by flash chromatography eluting with 30% to 50% diethyl ether in hexanes eluant. Mass spectrum: (m/e) 542 (M$^+$+1–H$_2$O, +ion).

Preparation 4d (2R,4aR,10aR)-7-(4-Nitrobenzoyloxy)-4a-Ethyl-2-hydroxy-2-phenyl-1,4,4a,9,10,10a-hexahydro-2H-phenanthren-3-one and (2R,4aR,10aS)-7-(4-Nitrobenzoyloxy)-4a-Ethyl-2-hydroxy-2-phenyl-1,2,4,4a,10,10a-hexahydrophenanthrene-3,9-dione

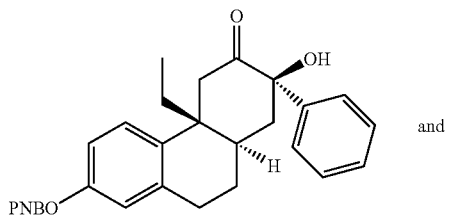

and

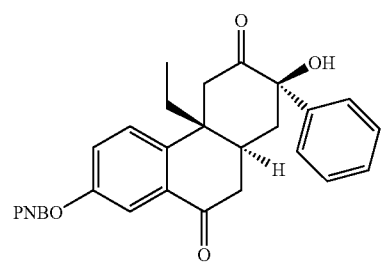

A solution of the compound of Preparation 4c (0.29 grams, 0.51 mmol) in a 1:1 mixture of methylene chloride and methanol (50 mL) at –78° C. was purged with ozone until saturated (dark blue). The mixture was kept saturated for 1 hour and then purged with nitrogen. Dimethylsulfide (1 mL) was added and the mixture was allowed to warm to room temperature. After 1 hour, the mixture was concentrated to give an oil which was partitioned between water (50 mL) and 50 diethyl ether (50 mL). The separated aqueous layer was extracted with diethyl ether (2×50 mL). The combined organic layers were washed with brine (50 mL), dried (MgSO$_4$), and concentrated. The title compounds were separated by flash chromatography using 10 to 40% diethyl ether in hexanes as eluant. Thus, 127 mg (49%) of the monoketone and 34 mg (13%) of the diketone were obtained; both were oils. Monoketone: Mass spectrum: (m/e) 468 (M$^+$+1–H$_2$O, +ion) and 485 (M$^+$, –ion). Diketone: Mass spectrum: (m/e) 499 (M$^+$, –ion).

Preparation 4e (2R,4aR,10aR)-4a-Ethyl-2,7-dihydroxy-2-phenyl-1,4,4a,9,10,10a-hexahydro-2H-phenanthren-3-one

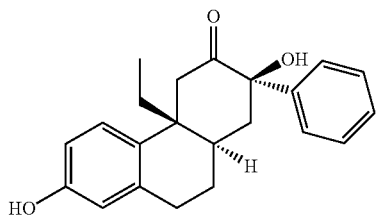

To a solution of the monoketone product of Preparation 4d (0.30 g, 0.62 mmol) in a 2:1 mixture of ethanol and THF at 0° C. was added 1 M aqueous sodium hydroxide (NaOH) solution (0.62 mL, 0.62 mmol). After 30 minutes, 1 M aqueous hydrochloric acid solution (0.5 mL) and brine (50 mL) were added, and the mixture was extracted with ethyl acetate (3×60 mL). The combined organic layers were washed with brine, dried (MgSO$_4$), and concentrated to an oil (360 mg). The title product (159 mg, 76%) was isolated by flash chromatography using 30% ethyl acetate in hexanes as eluant. Melting Point: 97–98° C. Analytical calculated for C$_{22}$H$_{24}$O$_3$: C, 78.54; H, 7.16. Found: C, 78.50; H, 7.46.

Preparation 4f (2R,4aR,10aS)-4a-Ethyl-2,7-dihydroxy-2-phenyl-1,2,4,4a,10,10a-hexahydro-phenanthrene-3,9-dione

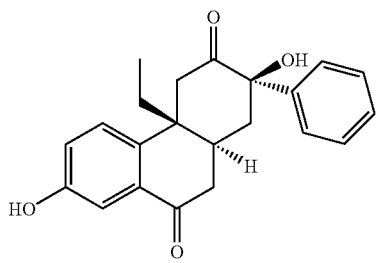

The compound of Preparation 4f was prepared according to the procedure of Preparation 4e, substituting the diketone of Preparation 4d for the monoketone of Preparation 4d. Melting Point: 140–144° C. Mass spectrum: (m/e) 349 (M$^+$–1, –ion).

Preparation 5a

(4aS,10aR)-4a-Ethyl-7-hydroxy-4a,9,10,10a-tetrahydro-1H-phenanthren-2-one

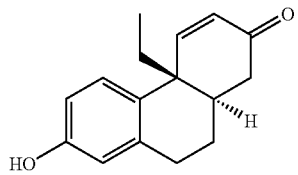

A solution of the bromide of Preparation 3a (4.0 grams, 12.3 mmol) in dimethylacetamide (150 mL) was added slowly to a refluxing mixture of calcium carbonate in dimethylacetamide (100 mL). The mixture was refluxed for 2 hours. After cooling, aqueous 1 M hydrochloric acid solution was added and the mixture was extracted twice with diethyl ether. The combined organic layers were washed with brine, dried (MgSO$_4$) and concentrated. The title compound (1.22 grams, 41%) was isolated by flash chromatography eluting with 5% ethyl acetate in methylene chloride. $^1$H NMR (CDCl$_3$): δ 7.68 (d, J=10.4 Hz, 1 H), 7.29 (d, J=8.8 Hz, 1 H), 6.72 (dd, J=3.1, 8.8 Hz, 1 H), 6.67 (d, J=3.1 Hz, 1 H), 6.10 (d, J=10.4 Hz, 1 H), 5.90 (br s, 1 H), 2.99–2.91 (m, 2 H), 2.61 (dd, J=14.3, 17.9 Hz, 1 H), 2.48–2.39 (m, 2 H), 2.01–1.92 (m, 1 H), 1.85–1.78 (m, 1 H), 1.75–1.70 (m, 1 H), 1.67–1.60 (m, 1H), 0.88 (t, J=7.8 Hz, 3 H).

Preparation 5b

(4aS,10aR)-7-(tert-Butyldimethylsilanyloxy)-4a-ethyl-4a,9,10,10a-tetrahydro-1H-phenanthren-2-one

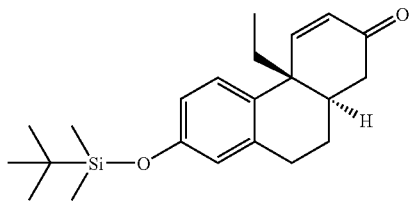

To a solution of the title product of Preparation 5a (245 mg, 1.01 mmol) in methylene chloride (20 mL) at room temperature was added imidazole (85 mg, 1.25 mmol) and tert-butyldimethylsilylchloride (175 mg, 1.16 mmol). The mixture was stirred at room temperature overnight. After dilution with methylene chloride, the solution was washed with 0.5 M aqueous citric acid solution, water and brine. The solution was dried (MgSO$_4$) and concentrated to afford the title compound as an oil, 322 mg (89%). $^1$H NMR (CDCl$_3$) selected signals: δ 7.67 (d, J=10.4 Hz, 1 H), 7.28 (d, J=8.3 Hz, 1 H), 6.72 (dd, J=2.6, 8.3 Hz, 1 H), 6.67 (d, J=2.6 Hz, 1 H), 6.08 (d, J=10.4 Hz, 1 H), 1.00 (s, 9 H), 0.21 (s, 6 H).

Preparation 6a

(4bR)-4b-Ethyl-7-oxo-4b,5,6,7,9,10-hexahydrophenanthrene-2-carbonitrile

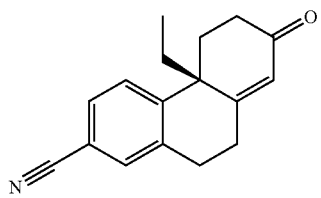

(4aR)-7-Bromo-4a-ethyl-7-4,4a,9,10-tetrahydro-3H-phenanthren-2-one was prepared in three steps from 6-bromo-2-tetralone in a manner analogous to that described for the synthesis of (4aR)-4a-ethyl-7-methoxy-4,4a,9,10-tetrahydro-3H-phenanthren-2-one in Preparations 1a to 1c.

To a solution of (4aR)-7-Bromo-4a-ethyl-7-4,4a,9,10-tetrahydro-3H-phenanthren-2-one (28.6 grams, 93.7 mmol) in N,N-dimethylformamide (680 mL) was added zinc cyanide (16.5 grams, 141 mmol) and tetrakis(triphenylphosphine) palladium (0) (12.9 grams, 11.2 mmol). The mixture was heated at 80–100° C. overnight employing a bleach trap to destroy hydrogen cyanide. After cooling, the mixture was filtered to remove the solids; and the filtrate was concentrated to a dark oil. The oil was taken up in ethyl acetate and washed sequentially with 10% aqueous ammonium hydroxide solution (twice), water and brine. The dark solution was dried (MgSO$_4$) and concentrated to a solid. The title compound (18.8 grams, 80%) was isolated by flash chromatography eluting with 10 to 25% acetone in hexane. $^1$H NMR (CDCl$_3$): δ 7.55 (d, J=8.3 Hz, 1 H), 7.46 (s, 1 H), 7.41 (d, J=8.3 Hz, 1 H), 6.00 (s, 1 H), 3.12–3.06 (m, 1 H), 2.93–2.87 (m, 1 H), 2.80–2.71 (m, 2 H), 2.68–2.64 (m, 1 H), 2.55–2.50 (m, 1 H), 2.45–2.41 (m, 1 H), 2.12–1.98 (m, 3 H), 0.84 (t, J=7.8 Hz, 3 H).

Preparation 6b

(4bR)-7-Ethoxy-4b-ethyl-4b,5,6,10-tetrahydrophenanthrene-2-carbonitrile

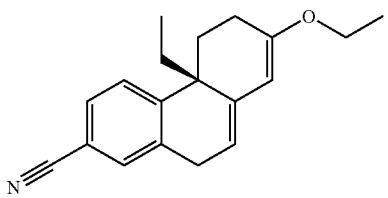

To a solution of the title product of Preparation 6a (18.8 grams, 74.0 mmol) in ethanol (230 mL) and triethyl orthoformate (450 mL) was added p-toluenesulfonic acid monohydrate (590 mg). The mixture was stirred at room temperature overnight and then concentrated to remove most of the ethanol. The remaining solution was diluted with ethyl acetate and washed sequentially with saturated aqueous sodium bicarbonate solution, water and brine. Concentration under vacuum provided the crude title compound as a dark oil. $^1$HNMR (CDCl$_3$) selected signals: δ 5.63 (dd, J=2.6, 5.2 Hz, 1 H), 5.31 (s, 1 H).

Preparation 6c (4bR,8aR)-4b-Ethyl-7-oxo-4b,5,6,7,8,8a,9,10-octahydrophenanthrene-2-carbonitrile

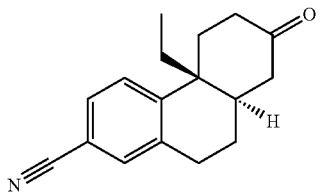

To the entire sample of the title product of preparation 6b (calculated for 74 mmol) in ethyl acetate (750 mL) was added potassium carbonate (9 grams, 65.1 mmol) and 10% palladium on carbon (4 grams). The mixture was hydrogenated in a Parr shaker at 3 atmospheres pressure of hydrogen gas for 26 hours. The mixture was filtered through Celite®, washing the filter cake with ethyl acetate, and concentrated to about the original volume under vacuum. Potassium carbonate (9 grams, 65.1 mmol) and 10% palladium on carbon (4 grams) were again added and hydrogenation was continued as before for a further 16 hours. At this point, additional 10% palladium on carbon (0.5 grams) was added and hydrogenation was continued for an additional 6 hours. The mixture was filtered through Celite®, washing the filter cake with ethyl acetate, and concentrated to an orange oil. This was dissolved in tetrahydrofuran (650 mL) and treated with 1 M aqueous hydrochloric acid solution (250 mL). The resulting mixture was stirred at room temperature for 6 hours and then concentrated to remove most of the tetrahydrofuran. After dilution with ethyl acetate, the organic layer was separated, washed with water and brine, and concentrated to give an orange solid. The title compound, a tan solid (6.92 grams, 37%), was isolated by trituration with ethyl acetate, collecting by filtration. $^1$HNMR (CDCl$_3$): δ 7.46–7.40 (m, 2 H), 7.34 (d, J=8.8 Hz, 1 H), 3.02–2.98 (m, 2 H), 2.75–2.71 (m, 1 H), 2.49–2.45 (m, 3 H), 2.39–2.36 (m, 1 H), 2.13–1.89 (m, 3 H), 1.76–1.70 (m, 1 H), 1.68–1.62 (m, 1 H), 1.58–1.52 (m, 1 H), 0.84 (t, J=7.8 Hz, 3 H).

Preparation 6d (4bR,6S,8aR)-6-Bromo-4b-ethyl-7-oxo-4b,5,6,7,8,8a,9,10-octahydrophenanthrene-2-carbonitrile

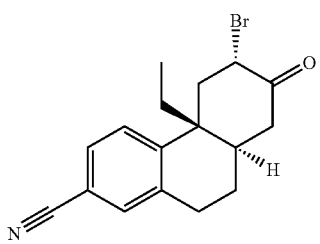

To a solution of the title product of Preparation 6c (1.0 grams, 3.95 mmol) in tetrahydrofuran (80 mL) at −78° C. was added phenyltrimethylammonium tribromide (1.56 grams, 4.15 mmol). The mixture was allowed to slowly warm to 0° C. over 5.5 hours. Saturated aqueous ammonium chloride solution was added and the mixture was extracted twice with ethyl acetate. The combined extracts were washed with brine, dried (MgSO$_4$) and concentrated under vacuum. The residue was taken up in ethyl acetate and filtered to collect a small amount of the title compound as a white solid (98 mg, 7.5%). The filtrate was concentrated to an oil from which more of the title compound (984 mg, 75%) was isolated by flash chromatography eluting with 25% ethyl acetate in hexane. (Some methylene chloride was used to dissolve the crude sample.) $^1$H NMR (CDCl$_3$) selected signals: δ 4.80 (dd, J=5.7, 13.8 Hz, 1 H), 3.31 (dd, J=5.7, 13.5 Hz, 1 H).

Preparation 6e (4bR,6S,8aR)-4b-Ethyl-6-hydroxy-7-oxo 4b,5,6,7,8,8a,9,10-octahydrophenanthrene-2-carbonitrile

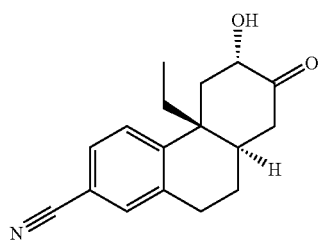

To a solution of the title product of Preparation 6d (1.08 grams, 3.25 mmol) in acetone (270 mL) and water (55 mL) was added potassium carbonate (0.44 grams, 3.18 mmol). The mixture was warmed at 50° C. for 2 hours and then at 60° C. for an additional 3.5 hours. The mixture was cooled in an ice bath, allowed to stand at room temperature overnight, and then quenched with excess 0.5 M aqueous hydrochloric acid solution. The mixture was extracted twice with ethyl acetate and the combined organic layers were washed with brine, dried (MgSO$_4$) and concentrated to a yellow solid. The title compound (564 mg, 64%) was isolated by flash chromatography eluting with 30% ethyl acetate in hexane. $^1$H NMR (CDCl$_3$) selected signals: δ 4.33–4.29 (m, 1 H), 3.14 (dd, J=6.2, 13 Hz, 1 H), 3.07–2.95 (m, 2H).

Preparation 7a (2S,3E,4aR,10aR)-3-Benzylidene-2-(2,6-difluorophenyl)-4a-ethyl-1,2,3,4,4a,9,10,10a-octahydrophenanthrene-2,7-diol

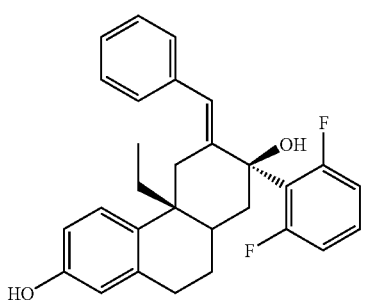

To a mixture of 2,6-difluorophenyllithium (3.0 mmol; prepared by the addition of 1,3-difluorobenzene (0.3 ml, 3.0 mmol) to a solution of n-butyl lithium 2.5 M in hexanes (1.2 ml) at −78° C.) and lithium chloride (127 mg, 3.0 mmol) in 5 mL of THF at −78° C. was added a solution of the compound of Preparation 4a (0.20 g, 0.6 mmol) in 5 mL THF. The mixture was stirred at −40° C. for 3 hours and then dilute aqueous hydrochloric acid was added. The mixture was extracted with ethyl acetate (3×30 mL). The combined organic layers were washed with 30 mL of brine, dried (MgSO$_4$), filtered and concentrated to afford 0.3 g (>100%) of the title compound as an oil, which was used in the next step without further purification. Mass spectrum: (m/e) 429 (M$^+$1−H$_2$O, +ion).

Preparations 7b–d

The compounds of Preparations 7b–d were prepared according to the procedure of Preparation 7a, substituting 2,6-dimethoxyphenyllithium, 2-methoxyphenyllithium and cyclopropyllithium for 2,6-difluorophenyllithium. The products were used in the next step without further purification.

| Prep. 7 | R | Mass Spectral Data |
|---|---|---|
| b | 2,6-dimethoxyphenyl | MS (m/e) 453 (M$^+$ + 1 —H$_2$O, +ion) |
| c | 2-methoxyphenyl | MS (m/e) 439 (M$^+$ − 1 −ion) |
| d | Cyclopropyl | MS (m/e) 357 (M$^+$ + 1 —H$_2$O, +ion) |

Preparations 8a–d

The compounds of Preparations 8a–d were prepared according to the procedure of Preparation 4c substituting the compounds of Preparations 7a–d for the compound of Preparation 4b. The products were used in the next step without further purification. (One skilled in the art will appreciate the PNB refers to p-nitrobenzyl).

| Prep. 8 | R | Mass Spectral Data |
|---|---|---|
| a | 2,6-difluorophenyl | MS (m/e) 578 (M$^+$ +1 —H$_2$O, +ion) |
| b | 2,6-dimethoxyphenyl | MS (m/e) 602 (M$^+$ +1 —H$_2$O, +ion) |
| c | 2-methoxyphenyl | MS (m/e) 590 (M$^+$ +1, +ion) |
| d | Cyclopropyl | MS (m/e) 506 (M$^+$ +1 —H$_2$O, +ion) |

Preparation 9

(2R,4aR,10aR)-2-Cyclopropyl-4a-ethyl-2.7-dihydroxy-1,4,4a,9,10,10a-hexahydro-2H-phenanthren-3-one

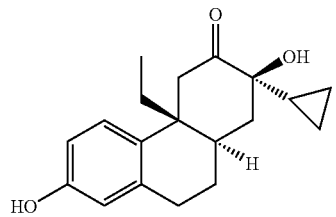

A solution of the compound of Preparation 8d (0.38 g, 0.73 mmol) in a 1:1 dichloromethane/methanol mixture (75 mL) at −78° C. was purged with ozone until saturated (dark blue) and kept saturated for 45 minutes. The mixture was purged with nitrogen and dimethylsulfide was added. The mixture was allowed to warm to room temperature overnight and then concentrated. The residue was dissolved in 50 mL of tetrahydrofuran (THF) at 0° C., and a solution of sodium hydroxide (NaOH) 1 N (1.9 mL, 2.9 mmol) was added. After 3 hours, 50 mL of saturated sodium bicarbonate was added. The mixture was extracted with ethyl acetate (2×50 mL). The combined organic layers were washed with brine, dried (MgSO$_4$), filtered and concentrated to an oil (156 mg). The residue was crystallized from ethyl ether to afford 86 mg (39%) of the title compound as a white powder. Mass spectrum: (m/e) 299 (M$^+$−1, −ion).

Preparation 10

(2R,3R,4aR,10aR)-7-[3-(tert-Butyl-dimethyl-silanyloxy)-propoxy]-4a-ethyl-3-methyl-2-phenyl-1,2,3,4,4a,9,10,10a-octahydro-phenanthrene-2,3-diol

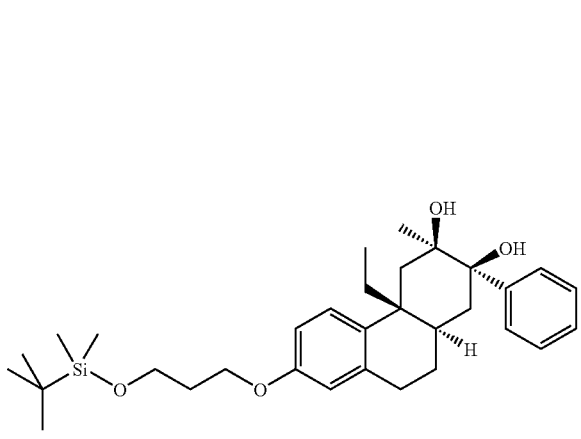

The compound of Preparation 10 was prepared according to the procedure of Example 57 substituting commercially available (3-bromopropoxy)-tert-butyldimethylsilane for 3-chloromethyl-2-methyl-pyridine hydrochloride. $^1$H NMR (CDCl$_3$) δ 0.04 (6H, s), 0.81 (3H, t), 0.88 (9H, s), 1.15 (3H, s), 1.19–1.28 (1H, m), 1.39–1.42 (1H, m), 1.56 (1H, dd, J=2.5, 12.9), 1.80–1.98 (3H, m), 2.22–2.29 (2H, m), 2.76–2.83 (2H, m), 3.78 (2H, t), 4.01 (2H, t), 6.61 (1H, d), 6.68 (1H, dd), 7.08 (1H, d), 7.20–7.28 (3H, m), 7.60 (2H, d).

Preparation 11a (3E,4aR,10aR)-3-Benzylidene-4a-ethyl-7-hydroxy-3,4,4a,9,10,10a-hexahydro-1H-phenanthren-2-one Ethylene Ketal

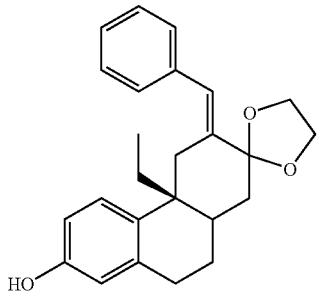

A mixture of the compound of Preparation 4a (10.0 g, 30.1 mmol), ethylene glycol (9.3 g, 150 mmol) and p-toluenesulfonic acid (0.57 g, 3.0 mmol) in 700 mL of toluene was heated at reflux using a Dean-Stark apparatus for 20 hours. The cooled mixture was concentrated to about 500 mL, poured over 500 mL of a saturated aqueous sodium bicarbonate solution and extracted with ethyl acetate (2×500 mL). The combined organic layers were washed with brine, dried (MgSO$_4$), filtered and concentrated to afford 13 g (>100%) of the title compound as a brown solid, which was used in the next step without further purification. Mass spectrum: (m/e) 377 (M$^+$+1, +ion).

Preparation 11b (4bR,6E,8aR)-4-Nitro-benzoic Acid 6-Benzylidine-4b-ethyl-7-oxo-4b,5,6,7,8,8a,9,10-octahydro-phenanthren-2-yl ester Ethylene Ketal

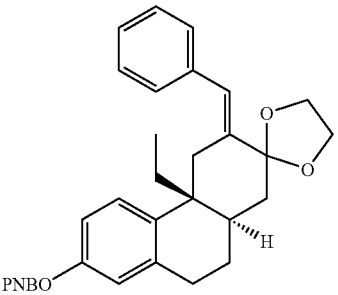

The compound of Preparation 11b was prepared as a beige solid (0.39 g, >100%) according to the procedure of Preparation 4c, substituting the compound of Preparation 11a (0.265 g, 0.70 mmol) for the compound of Preparation 4b. Mass spectrum: (m/e) 526 (M$^+$+1, +ion).

Preparation 11c (4aR,10aR)-4a-Ethyl-7-hydroxy-1,4,4a,9,10,10a-hexahydro-phenanthrene-2,3-dione 2-Ethylene Ketal

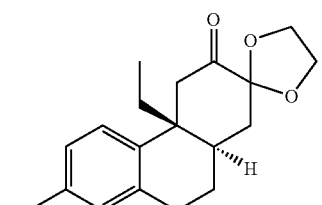

The compound of Preparation 11c was prepared as an oil (0.234 g, >100%) according to the procedure of Preparations 4d and 4e substituting the compound of Preparation 11b (0.39 g, 0.7 mmol) for the compound of Preparation 4c. This material was used in the next step without further purification. Mass spectrum: (m/e) 526 (M$^+$+1, +ion).

Preparation 11d (3R,4aR,10aR)-4a-Ethyl-3,7-dihydroxy-3-methyl-3,4,4a,9,10,10a-hexahydro-1H-phenanthren-2-one Ethylene Ketal

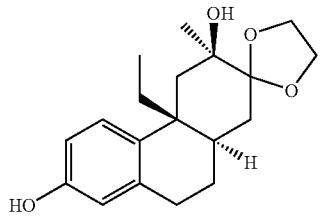

The compound of Preparation 11d was prepared as an oil (0.261 g, >100%) according to the procedure of Examples 42 and 43 substituting the compound of Preparation 11c (0.229 g, 0.70 mmol) for the compound of Preparation 4e. This material was used in the next step without further purification. Mass spectrum: (m/e) 301 (M$^+$−18+1, +ion).

Preparation 11e (3R,4aR,10aR)-4a-Ethyl-3,7-dihydroxy-3-methyl-3,4,4a,9,10,10a-hexahydro-1H-phenanthren-2-one

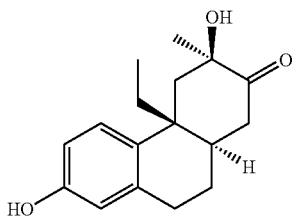

A mixture of the compound of Preparation 11d (3.87 g, 12.2 mmol), 2 N aqueous hydrochloric acid solution (125 mL) and tetrahydrofuran (125 mL) was heated at reflux for 1 hour. The mixture was poured over 100 mL of water, and the aqueous layer was separated and extracted with ethyl acetate (2×250 mL). The combined organic layers were washed with saturated sodium bicarbonate solution and brine, dried (MgSO$_4$), filtered and concentrated to a foam (3.1 g), which was purified by flash chromatography using a 50% to 70% ethyl ether in hexanes eluant to afford 2.54 g (76%) of the title compound as beige foam. Mass spectrum: (m/e) 273 (M$^+$–1, –ion).

Preparation 11f (3R,4aR,10aR)-7-(tert-Butyldimethylsilanyloxy)-4a-ethyl-3-hydroxy-3-methyl-3,4,4a,9,10,10a-hexahydro-1H-phenanthren-2-one

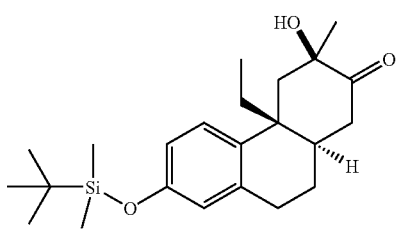

To a solution of the compound of Preparation 11e (280 mg, 1.02 mmol) in dichloromethane (30 mL) was added imidazole (104 mg, 1.53 mmol) and t-butyldimethylsilyl chloride (231 mg, 1.53 mmol). After stirring the reaction mixture overnight, it was quenched with aqueous 0.5 N citric acid solution. The aqueous phase was extracted with dichloromethane and the combined organic layers were washed with water and brine, dried over magnesium sulfate and concentrated to afford the title compound as an oil.

Preparation 12a (3E,4aR,10aR)-3-Benzylidene-7-(tert-butyl-dimethylsilanyloxy)-4a-ethyl-3,4,4a,9,10,10a-hexahydro-1H-phenanthren-2-one

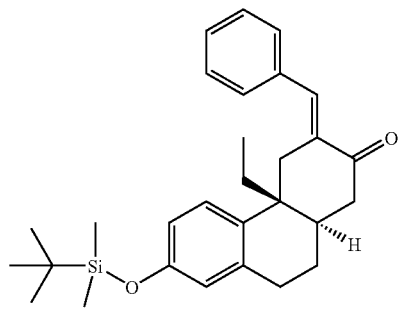

To a solution of the compound of Preparation 4a (10.0 grams, 30 mmol) in dichloromethane (300 mL) was added imidazole (3.47 grams, 51 mmol) and t-butyldimethylsilyl chloride (7.69 grams, 51 mmol). The reaction mixture was stirred overnight and then additional imidazole (0.68 grams, 10 mmol) and t-butyldimethylsilyl chloride (1.5 grams, 10 mmol) were added. After stirring the reaction mixture for a total of 2 days, an aqueous 0.5 N citric acid solution was added. The aqueous phase was extracted with dichloromethane and the combined organic layers were washed with water and brine, dried over magnesium sulfate and concentrated. The title compound (6.59 grams, 49%) was isolated by flash chromatography eluting with a gradient of 100% hexane to 30% ethyl acetate in hexane.

Preparation 12b (2S,3E,4aR,10aR)-3-Benzylidene-4a-ethyl-2-pyridin-2-yl-1,2,3,4,4a,9,10,10a-octahydro-phenanthrene-2,7-diol

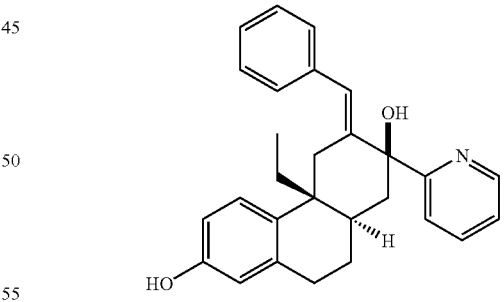

A solution of 2-bromopyridine (14.2 mL, 0.148 mol) in tetrahydrofuran (500 mL) was cooled to –78° C. and a 2.5 M solution of n-butyllithium in hexane was added slowly. After stirring the mixture for 30 minutes, a solution of the title compound of Preparation 12a (6.59 grams, 14.75 mmol) in tetrahydrofuran (150 mL) was added dropwise with stirring. The mixture was allowed to stir at 0° C. for 4 hours and was then quenched by addition of water (200 mL). The mixture was extracted twice with ethyl acetate. The combined organic layers were washed with water and brine, dried over magnesium sulfate and concentrated.

The residue was dissolved in tetrahydrofuran and cooled to 0° C. A 1 M solution of tetra-n-butylammonium fluoride in tetrahydrofuran (23 mL) was added and the resulting mixture was allowed to stir at 0° C. for 4 hours. The solution was passed through a plug of silica gel, washing with ethyl acetate, and concentrated. The residue was chromatographed on silica gel eluting with a gradient of 30% to 65% ethyl acetate in hexane. The title compound (3.9 grams, 64%) was obtained by concentration of the appropriate fractions and trituration with ether.

Preparation 12c

4-Nitrobenzoic acid, (4bR,6E,7S,8aR)-6-benzylidene-4b-ethyl-7-hydroxy-7-pyridin-2-yl-4b,5,6,7,8,8a,9,10-octahydro-phenanthren-2-yl ester

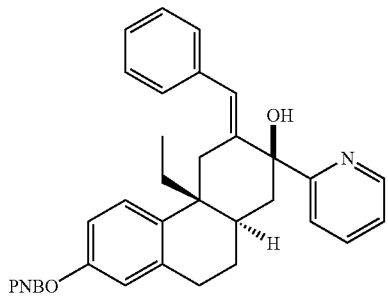

A solution of the compound of Preparation 12b (1.3 grams, 3.16 mmol) in acetone (35 mL) was cooled to 0° C. Aqueous 1 N NaOH solution (3.2 mL, 3.2 mmol) was added followed by p-nitrobenzoyl chloride (674 mg, 3.6 mmol). The reaction mixture was stirred at 0° C. for 2.5 hours and then quenched by addition of saturated aqueous sodium bicarbonate solution. The mixture was extracted twice with ethyl acetate and the combined organic layers were washed with brine, dried over magnesium sulfate and concentrated to afford the crude title compound as a yellow foam, 1.57 grams (89%).

Preparation 12d (2R,4aR,10aR)-4a-Ethyl-2,7-dihydroxy-2-pyridin-2-yl-1,4,4a,9,10,10a-hexahydro-2H-phenanthren-3-one

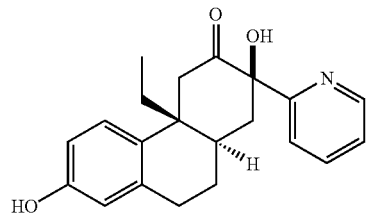

A solution of the title compound of Preparation 12c (3.7 grams, 6.6 mmol) in methanol (100 mL) and dichloromethane (200 mL) was cooled to −78° C. Aqueous 6N HCl solution (1.25 mL) was added. Ozone was bubbled through the solution for 5 minutes until a light blue color was apparent. After continued stirring at −78° C. for 10 minutes, oxygen was bubbled through the solution for a further 5 minutes. Dimethylsulfide (4 mL, 54 mmol) was then added. The mixture was allowed to warm to room temperature and then concentrated. The residue was dissolved in tetrahydrofuran (40 mL) and aqueous 1 N NaOH solution (20 mL, 20 mmol) was added. The mixture was allowed to stir at room temperature overnight and was acidified by the addition of excess aqueous 1N hydrochloric acid. After extraction twice with ethyl acetate, the combined organic fractions were washed with saturated aqueous sodium bicarbonate solution and brine. The solution was dried over magnesium sulfate and evaporated to provide a solid from which the title compound (1.38 grams, 62%) was obtained by trituration with ether and hexane. Additional product was isolated by concentration of the filtrate and flash chromatography of the residue eluting with a gradient of 10% to 70% ethyl acetate in hexane.

Example 1

(2R,3S,4aR,10aR)-4a-Ethyl-2-prop-1-ynyl-1,2,3,4,4a,9,10,10a-octahydrophenanthrene-2,3,7-triol

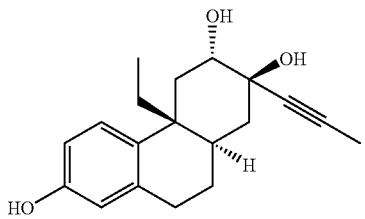

Tetrahydrofuran (10 mL) was saturated with propyne at 0° C. After cooling to −78° C., a 2.5 M solution of n-butyl lithium in hexane (6 mL, 15 mmol) was carefully added. After stirring for 15 minutes at −78° C., the resulting mixture was allowed to warm to 0° C. A solution of the product mixture of Preparation 3b (191 mg, 0.73 mmol, 9:1 ratio favoring the 2-keto isomer) in tetrahydrofuran (10 mL) was then added dropwise. The reaction mixture was allowed to warm to room temperature while stirring overnight. Saturated aqueous ammonium chloride was added and the mixture was extracted with diethyl ether and ethyl acetate. The combined organic layers were washed with brine, dried (MgSO$_4$) and concentrated to afford an oil from which the title compound (54 mg, 25%) was isolated by flash chromatography eluting with 45% ethyl acetate in methylene chloride. $^1$H NMR (CDCl$_3$) selected signals: δ 7.04 (d, J=8.8 Hz, 1 H), 6.60–6.57 (m, 2H), 3.82 (dd, J=4.2, 11.9 Hz, 1 H) 2.89–2.85 (m, 2 H), 2.43 (dd, J=4.2, 13 Hz, 1 H), 1.88 (s, 3 H), 0.78 (t, J=7.8 Hz, 3 H). The 2S diastereomer of the title compound was also isolated.

Example 2

(2R,3S,4aR,10aR)-4a-Ethyl-7-(2-methylpyridin-3-ylmethoxy)-2-prop-1-ynyl-1,2,3,4,4a,9,10,10a-octahydrophenanthrene-2,3-diol

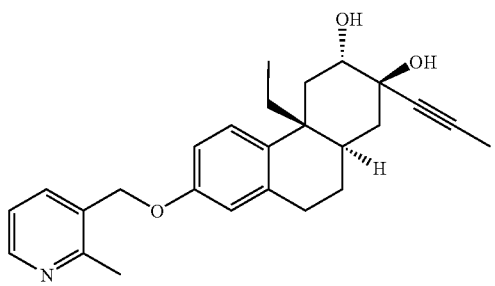

To a solution of the title product of Example 1 (100 mg, 0.33 mmol) in N,N-dimethylformamide (10 mL) was added a 60% suspension of sodium hydride in oil (30 mg, 0.75 mmol). After stirring at room temperature for 30 minutes, 3-chloromethyl-2-methyl pyridine hydrochloride (70 mg, 0.39 mmol) was added and the mixture was allowed overnight at room temperature. The reaction was quenched by addition of saturated aqueous ammonium chloride solution. The mixture was extracted twice with ethyl acetate and the combined extracts were washed with brine, dried (MgSO$_4$) and concentrated to an oil. The title product (76 mg, 57%) was isolated by flash chromatography eluting with 10% methylene chloride in ethyl acetate. Mass spectrum: m/e 406 (M+1).

Example 3

(2R,3S,4aR,10aR)-4a-Ethyl-2-prop-1-ynyl-7-(pyridin-2-ylmethoxy)-1,2,3,4,4a,9,10,10a-octahydrophenanthrene-2,3-diol

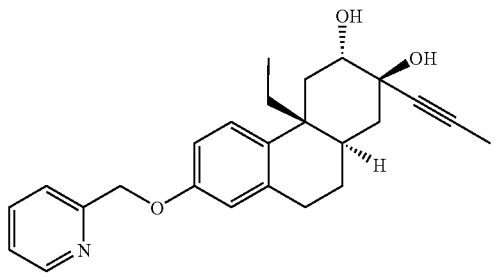

The title compound was prepared from the compound of Example 1 and 2-picolyl chloride hydrochloride using the procedure of Example 2. The product was isolated by flash chromatography eluting with 10% methylene chloride in ethyl acetate. Mass spectrum: m/e 392 (M+1).

Example 4

(2R,3S,4aR,10aR)-4a-Ethyl-2-prop-1-ynyl-7-(pyridin-4-ylmethoxy)-1,2,3,4,4a,9,10,10a-octahydrophenanthrene-2,3-diol

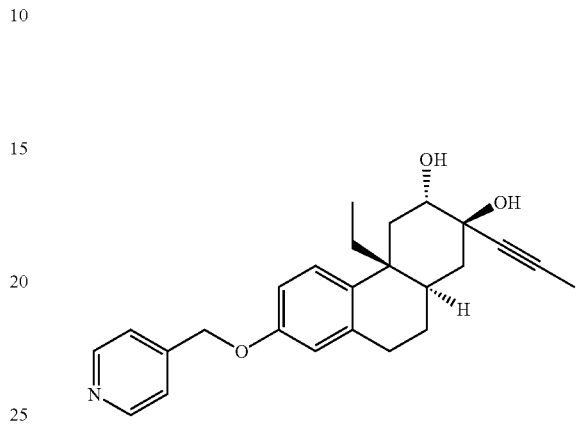

The title compound was prepared from the compound of Example 1 and 4-picolyl chloride hydrochloride using the procedure of Example 2. The product was isolated by flash chromatography eluting with ethyl acetate. $^1$H NMR (CDCl$_3$) selected signals: δ 8.64 (br s, 2H), 7.40 (d, J=5 Hz, 2 H), 7.11 (d, J=8.3 Hz, 1 H), 6.76–6.74 (m, 2 H), 5.08 (s, 2 H), 3.62 (dd, J=4.2, 12.2 Hz, 1 H), 2.96–2.90 (m, 2 H), 2.59 (dd, J=4.2, 13.0 Hz, 1 H), 1.83 (s, 3 H), 0.78 (t, J=7.3 Hz, 3 H).

Example 5

(2R,3S,4aR,10aR)-7-(2,4-Dimethylpyridin-3-ylmethoxy)-4a-ethyl-2-prop-1-ynyl-1,2,3,4,4a,9,10,10a-octahydrophenanthrene-2,3-diol

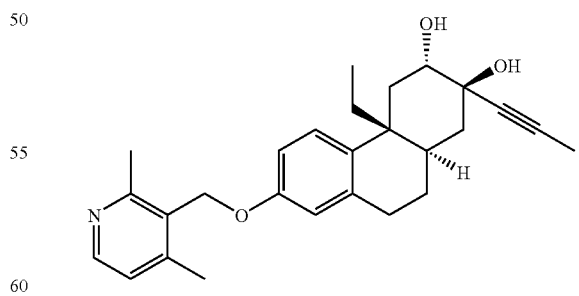

The title compound was prepared from the compound of Example 1 and 3-chloromethyl-2,4-dimethylpyridine hydrochloride using the procedure of Example 2. The product was isolated by flash chromatography eluting with ethyl acetate. Mass spectrum: m/e 420 (M+1).

Example 6

(2R,3S,4aR,10aR)-4a-Ethyl-2-prop-1-ynyl-7-(pyridin-3-ylmethoxy)-1,2,3,4,4a,9,10,10a-octahydrophenanthrene-2,3-diol

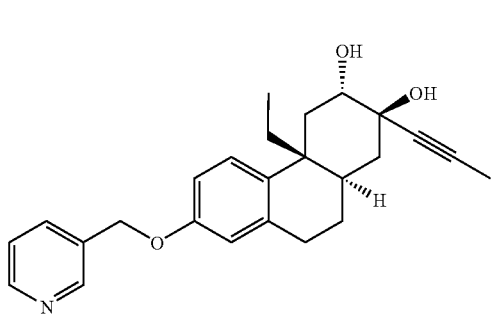

The title compound was prepared from the compound of Example 1 and 3-picolyl chloride hydrochloride using the procedure of Example 2. The product was isolated by flash chromatography eluting with 10 to 100% ethyl acetate in methylene chloride. Mass spectrum: m/e 392 (M+1).

Example 7

(2R,3S,4aR,10aR)-4a-Ethyl-7-(6-methylpyridin-3-ylmethoxy)-2-prop-1-ynyl-1,2,3,4,4a,9,10,10a-octahydrophenanthrene-2,3-diol

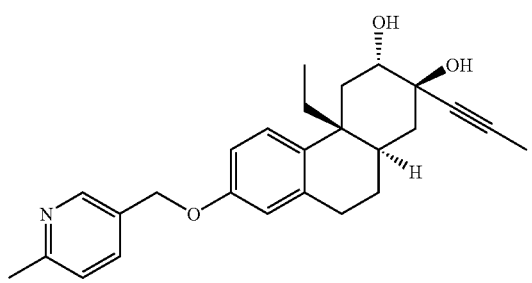

The title compound was prepared from the compound of Example 1 and 3-chloromethyl-6-methylpyridine hydrochloride using the procedure of Example 2. The product was isolated by flash chromatography eluting with 10 to 100% ethyl acetate in methylene chloride. Mass spectrum: m/e 406 (M+1).

Example 8

(2R,3S,4aR,10aR)-7-(5-Diethylaminomethyl-[1,2,4]oxadiazol-3-ylmethoxy)-4a-ethyl-2-prop-1-ynyl-1,2,3,4,4a,9,10,10a-octahydrophenanthrene-2,3-diol

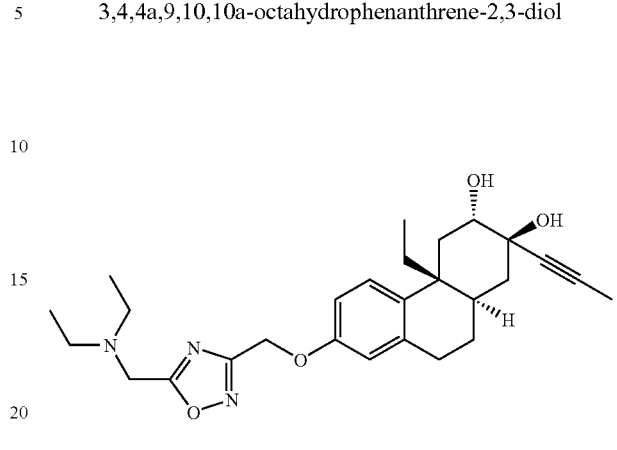

The title compound was prepared from the compound of Example 1 and (3-chloromethyl-[1,2,4]oxadiazol-5-ylmethyl)diethylamine using the procedure of Example 2. The product was isolated by flash chromatography eluting with 1% methanol in chloroform. Mass spectrum: m/e 468 (M+1).

Example 9

(2-Dimethylaminoethyl)methylcarbamic acid, (6S,7R,4bR,8aR)-4b-ethyl-6,7-dihydroxy-7-prop-1-ynyl-4b,5,6,7,8,8a,9,10-octahydrophenanthren-2-yl ester

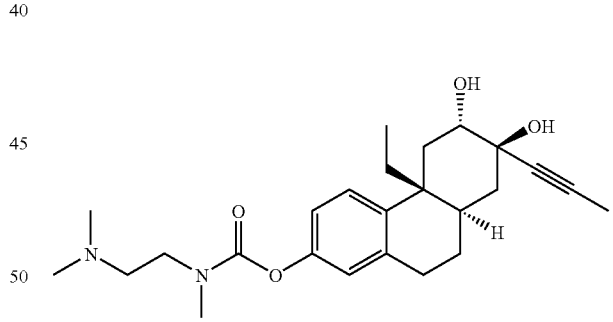

To a solution of the title product of Example 1 (27 mg, 0.09 mmol) in tetrahydrofuran (2 mL) was added triethylamine (0.015 mL, 0.11 mmol) followed by 20% phosgene in toluene (0.057 mL, 0.11 mmol). After stirring the mixture for 3 hours, N,N,N-trimethylethylenediamine (0.058 mL, 0.45 mmol) was added and the reaction was allowed to stir overnight at room temperature. The mixture was diluted with ethyl acetate, washed with saturated aqueous ammonium chloride solution, dried (MgSO$_4$) and concentrated under vacuum. The title product (4.4 mg) was isolated by preparative reverse phase HPLC using 0.1% aqueous formic acid and acetonitrile as eluant (gradient 5 to 100% acetonitrile). Mass spectrum: m/e 429 (M+1).

Example 10

(2S,3S,4aR,10aR)-2-Butyl-4a-ethyl-1,2,3,4,4a,9,10,10a-octahydrophenanthrene-2,3,7-triol

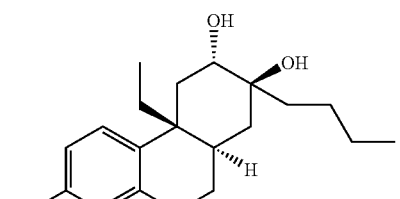

A solution of the product mixture of Preparation 3b (105 mg, 0.40 mmol, >9:1 ratio favoring the 2-keto isomer) in tetrahydrofuran (2.5 mL) was cooled to −78° C. A 2.5 M solution of n-butyl lithium in hexane (0.7 mL, 1.75 mmol) was added. The resulting mixture was allowed to slowly warm to room temperature while stirring overnight. Saturated aqueous ammonium chloride solution was added and the mixture was extracted with ethyl acetate. The organic layer was washed with brine, dried ($Na_2SO_4$) and concentrated to afford a yellow oil from which the title compound (10 mg, 8%) was isolated by flash chromatography eluting with 30% ethyl acetate in hexane. $^1$H NMR ($CDCl_3$) selected signals: δ 3.81–3.78 (m, 1H), 2.91–2.88 (m, 2 H), 2.52 (dd, J=4.1, 13.0 Hz, 1 H). The 2R diastereomer of the title compound was also isolated (21 mg, 16%).

Example 11

(2R,3S,4aR,10aR)-2-(3-Chloro-5-fluorophenyl)-4a-ethyl-1,2,3,4,4a,9,10,10a-octahydrophenanthrene-2,3,7-triol

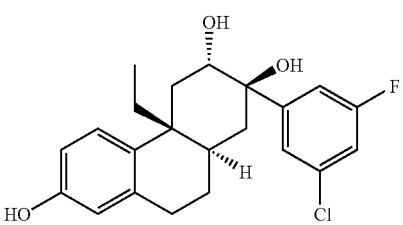

The title compound was prepared from the compound of Preparation 3b and 3-chloro-5-fluorophenylmagnesium bromide using the procedure of Example 10. The title compound was isolated by flash chromatography eluting with 1.5% methanol in chloroform. $^1$H NMR ($CDCl_3$) selected signals: δ 7.59 (s, 1 H), 7.46 (d, J=10.9 Hz, 1 H), 7.02 (d, J=8.3 Hz, 1 H), 6.99 (dt, J=2.1, 8.3 Hz, 1 H), 6.60 (dd, J=2.6, 8.3 Hz, 1 H), 6.56 (d, J=2.6 Hz, 1 H), 4.16 (dd, J=4.2, 13.5 Hz, 1 H), 2.66 (dd, J=4.2, 13.0 Hz, 1 H). The 2S diastereomer of the title compound was also isolated.

Example 12

(2R,3S,4aR,10aR)-2-(3-Chloro-5-fluorophenyl)-4a-ethyl-7-(2-methylpyridin-3-ylmethoxy)-1,2,3,4,4a,9,10,10a-octahydrophenanthrene-2,3-diol

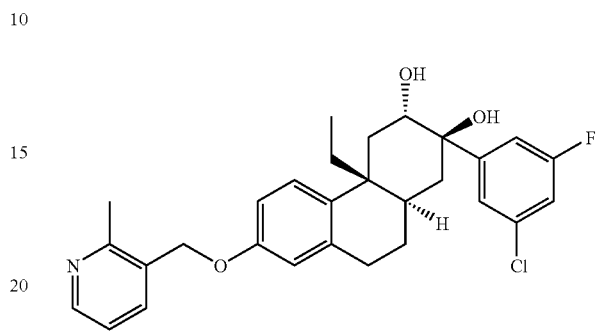

The title compound was prepared from the compound of Example 11 and 3-chloromethyl-2 methylpyridine hydrochloride using a procedure analogous to that outlined for Example 2. The product was isolated by flash chromatography eluting with 30% ethyl acetate in methylene chloride. $^1$H NMR ($CDCl_3$) selected signals: δ 8.48–8.46 (m 1 H), 7.74 (d, J=7.3 Hz, 1 H), 7.61 (s, 1 H), 7.47 (d, J=10.4 Hz, 1 H), 7.20–7.17 (m, 1 H), 7.11 (d, J=8.3 Hz, 1 H), 6.99 (d, J=7.8 Hz, 1 H), 6.76 (dd, J=2.6, 8.3 Hz, 1 H), 6.71 (d, J=2.6 Hz, 1 H), 5.00 (s, 2 H), 2.60 (s, 3 H).

Example 13

(2R,3S,4aR,10aR)-4a-Ethyl-2-(5-methylthiazol-2-yl)-1,2,3,4,4a,9,10,10a-octahydrophenanthrene-2,3,7-triol

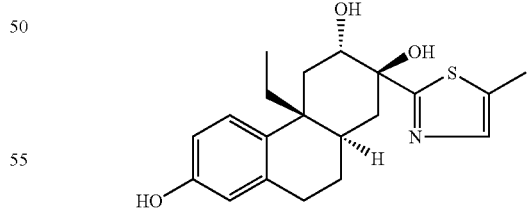

The title compound was prepared starting from the title 2-keto product of Preparation 3b and 5-methylthiazol-2-yl lithium (generated in situ from 5-methylthiazole and n-butyl lithium) using a procedure analogous to that outlined for Example 10. The title compound was isolated by flash chromatography eluting with 1.5% methanol in methylene chloride. Mass spectrum: m/e 360 (M+1). The 2S diastereomer of the title compound was also isolated.

Example 14

(2R,3S,4aR,10aR)-2-(4,5-Dimethylthiazol-2-yl)-4a-ethyl-1,2,3,4,4a,9,10,10a-octahydrophenanthrene-2,3,7-triol

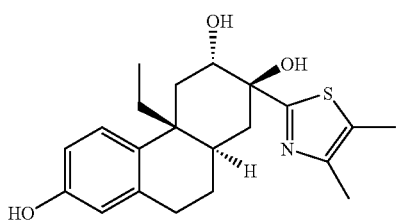

The title compound was prepared starting from the title 2-keto product of Preparation 3b and 4,5-dimethylthiazol-2-yl lithium (generated in situ from 4,5-methylthiazole and n-butyl lithium) using a procedure analogous to that outlined for Example 10. The title compound was isolated by flash chromatography eluting with 32% ethyl acetate in hexanes. Mass spectrum: m/e 374 (M+1). The 2S diastereomer of the title compound was also isolated.

Example 15

(2R,3S,4aR,10aR)-4a-Ethyl-2-trifluoromethyl-1,2,3,4,4a,9,10,10a-octahydrophenanthrene-2,3,7-triol

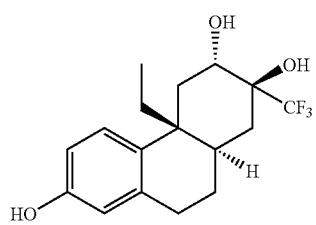

A solution of the product mixture of Preparation 3b (116 mg, 0.45 mmol, 5:1 ratio favoring the 2-keto isomer) in tetrahydrofuran (2.5 mL) was cooled to −78° C. A 0.5 M solution of trimethyl(trifluoromethyl)silane in tetrahydrofuran (4.45 mL, 2.23 mmol) was added followed by cesium fluoride (18 mg, 0.12 mmol). The mixture was allowed to slowly warm to room temperature while stirring overnight. Excess 1M aqueous hydrochloric acid solution was then added and stirring was continued for a second night. The mixture was then extracted twice with ethyl acetate and the combined organic layers were washed with brine, dried (Na$_2$SO$_4$), and concentrated. The title compound (11 mg, 7%) was isolated by preparative reverse phase HPLC using 0.1% aqueous formic acid and acetonitrile as eluant (gradient 5 to 80% acetonitrile). $^1$H NMR (CDCl$_3$) selected signals: δ 4.66 (dd, J=4.7, 11.4 Hz, 1 H), 2.92–2.88 (m, 2 H), 2.59–2.57 (m, 1 H). The 2S diastereomer of the title compound was also isolated.

Example 16

(2R,3S,4aR,10aR)-4a-Ethyl-2-phenyl-1,2,3,4,4a,9,10,10a-octahydrophenanthrene-2,3,7-triol

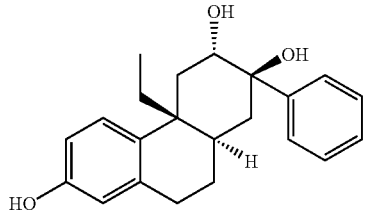

To a solution of the compound of Preparation 4e (25 mg, 0.074 mmol) in a 1:2 mixture of tetrahydrofuran and ethanol (5 mL) was added sodium borohydride (6 mg, 0.15 mmol). After 3 hours, 1M aqueous hydrochloric acid was added to adjust the pH to 4. Water (20 mL) was added and the mixture extracted with ethyl acetate (3×20 mL). The combined organic layers were washed with brine, dried (MgSO$_4$), and concentrated to afford the title compound (25 mg, 100%) as a white solid. Melting Point: 191–192° C. Mass spectrum: m/e 321 (M+1−H$_2$O).

Example 17

(2R,3S,4aR,10aR)-4a-Ethyl-2-phenyl-7-(pyridin-4-ylmethoxy)-1,2,3,4,4a,9,10,10a-octahydrophenanthrene-2,3-diol

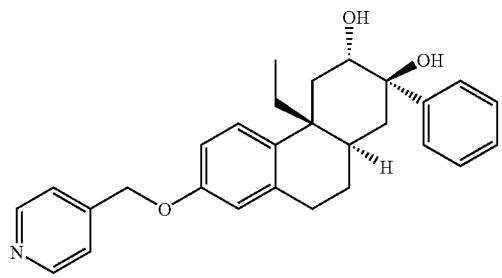

The title compound was prepared starting from the title product of Example 16 and 4-picolyl chloride hydrochloride using a procedure analogous to that outlined for Example 2. Product was isolated by flash chromatography eluting with 25% ethyl acetate in methylene chloride. Mass spectrum: m/e 430 (M+1).

Example 18

(2R,3S,4aR,10aR)-4a-Ethyl-2-phenyl-7-(pyridin-3-ylmethoxy)-1,2,3,4,4a,9,10,10a-octahydrophenanthrene-2,3-diol

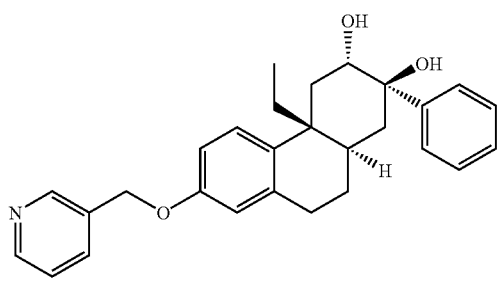

The title compound was prepared starting from the title product of Example 16 and 3-picolyl chloride hydrochloride using a procedure analogous to that outlined for Example 2. Product was isolated by flash chromatography eluting with 25% ethyl acetate in methylene chloride. Mass spectrum: m/e 430 (M+1).

Example 19

(2R,3S,4aR,10aR)-4a-Ethyl-7-(2-methylpyridin-3-ylmethoxy)-2-phenyl-1,2,3,4,4a,9,10,10a-octahydrophenanthrene-2,3-diol

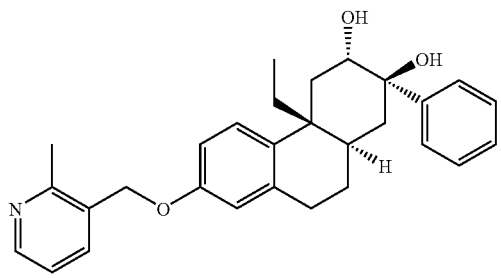

The title compound was prepared starting from the title product of Example 16 and 3-chloromethyl-2 methylpyridine hydrochloride using a procedure analogous to that outlined for Example 2. Product was isolated by flash chromatography eluting with 30% methylene chloride in ethyl acetate. Mass spectrum: m/e 444 (M+1).

Example 20

(2R,3S,4aR,10aR)-4a-Allyl-2-phenyl-1,2,3,4,4a,9,10,10a-octahydrophenanthrene-2,3,7-triol

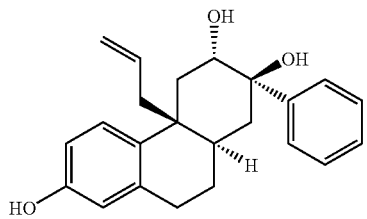

The title compound was prepared starting from the title product of Preparation 2b using procedures analogous to those outlined in Preparations 3a to 3b and for preparation of Example 10 (using phenylmagnesium bromide in place of butyl lithium). Product was isolated by flash chromatography eluting with 30% ethyl acetate in hexane. $^1$H NMR (CDCl$_3$) selected signals: δ 4.25 (dd, J=4.2, 13.0 Hz, 1 H), 2.88–2.75 (m, 2 H), 2.65 (dd, J=4.7, 13.0 Hz, 1H), 2.55 (dd, J=9.3, 13.5 Hz, 1 H).

Examples 21 and 22

(2R,3R,4aR,10aR)-2-Benzyl-4a-ethyl-1,2,3,4,4a,9,10,10a-octahydrophenanthrene-2,3,7-triol and (2R,3S,4aR,10aR)-2-benzyl-4a-ethyl-1,2,3,4,4a,9,10,10a-octahydrophenanthrene-2,3,7-triol Example 21

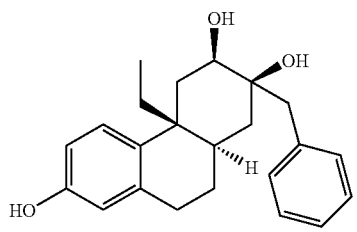

Example 22

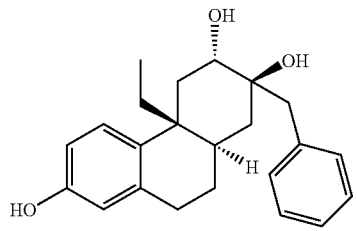

To a solution of the title compound of Preparation 3e (63 mg, 0.18 mmol) in methanol at 0° C. was added sodium borohydride (27 mg, 0.71 mmol). After stirring for 2 hours at 0° C., the reaction was quenched by addition of aqueous 0.5 M citric acid solution. The solvents were evaporated and the residue was taken up in water. The mixture was extracted twice with ethyl acetate and the combined organic layers were washed with brine, dried (MgSO$_4$) and concentrated to an oil. The title compounds were isolated by flash chromatography eluting with 30 to 70% ethyl acetate in hexane. Example 21 less polar, $^1$H NMR (CDCl$_3$) selected signals: δ 3.85 (br s, 1 H), 2.13 (dd, J=7.3, 13.0 Hz, 1 H). Example 22 more polar, ¹H NMR (CDCl₃) selected signals: δ 3.97 (dd, J=4.1, 12.4 Hz, 1 H), 2.61 (dd, J=4.1, 13.0 Hz, 1 H).

Examples 23 and 24

(2R,3R,4aR,10aR)-4a-allyl-2-benzyl-1,2,3,4,4a,9,10,10a-octahydrophenanthrene-2,3,7-triol and (2R,3S,4aR,10aR)-4a-allyl-2-benzyl-1,2,3,4,4a,9,10,10a-octahydrophenanthrene-2,3,7-triol

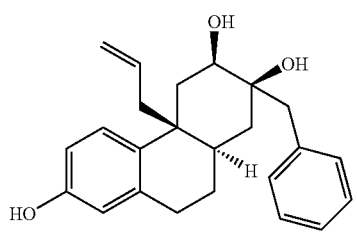

Example 23

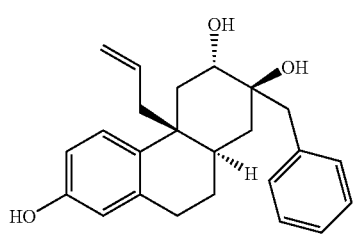

Example 24

The title compounds were prepared starting from the title product of Preparation 2b using procedures analogous to those outlined in Preparations 3a to 3e and for preparation of Examples 21 and 22. Product was isolated by flash chromatography eluting with 30% ethyl acetate in methylene chloride. Example 23 less polar, ¹HNMR (CDCl₃) selected signals: δ 3.83 (br s, 1 H), 2.71 (dd, J=3.0, 15.0 Hz, 1 H). Example 24 more polar, ¹H NMR (CDCl₃) selected signals: δ 4.05 (dd, J=4.1, 12.4 Hz, 1 H), 2.57 (dd, J=4.1, 13.0 Hz, 1 H), 2.45 (dd, J=9.1, 13.3 Hz, 1 H).

Examples 25 and 26

(2R,3R,4aR,10aR)-2.4a-diallyl-1,2,3,4,4a,9,0,10a-octahydrophenanthrene-2,3,7-triol and (2R,3S,4aR,10aR)-2.4a-diallyl-1,2,3,4,4a,9,10,10a-octahydrophenanthrene-2,3,7-triol

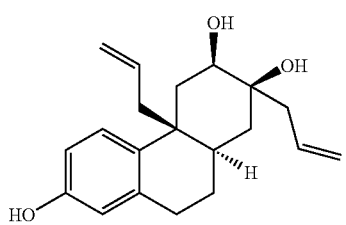

Example 25

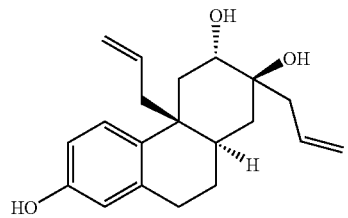

Example 26

The title compounds were prepared starting from the title product of Preparation 2b using procedures analogous to those outlined in Preparations 3a to 3e (alkylating with allyl bromide in place of benzyl bromide) and for preparation of Examples 21 and 22. Product was isolated by flash chromatography eluting with 20 to 70% ethyl acetate in hexane. Example 25 less polar, ¹H NMR (CDCl₃) selected signals: δ 3.80 (br s, 1 H). Example 26 more polar, ¹H NMR (CDCl₃) selected signals: δ 3.95 (dd, J=4.1, 12.4 Hz, 1H).

Example 27

(2R,3S,4aR,10aR)-4a-Ethyl-2-(pyridin-3-yl)-1,2,3,4,4a,9,10,10a-octahydrophenanthrene-2,3,7-triol To a solution of 3-bromopyridine (0.24 mL, 2.5 mmol) in tetrahydrofuran (10 mL) at −78° C. was added a 2.5 M solution of n-butyllithium in hexane (0.9 mL, 2.25 mmol). After stirring for 30 minutes at −78° C., a solution of the title product of Preparation 5b (105 mg, 0.29 mmol) in tetrahydrofuran (4 mL) was added dropwise and stirring was continued at −78° C. for 2 hours. The reaction was quenched by the addition of saturated aqueous ammonium chloride solution and extracted twice with ethyl acetate. The combined organic extracts were washed with brine, dried (MgSO₄) and concentrated. The residue was chromatographed on silica gel eluting with 20% ethyl acetate in hexane to provide (2S,4aS,10aR)-7-(tert-butyl-dimethylsilanyloxy)-4a-ethyl-2-pyridin-3-yl-1,2,4a,9,10,10a-hexahydrophenanthren-2-ol as a clear oil (104 mg, 81%).

¹H NMR (CDCl₃): δ 8.69 (br s, 1 H), 8.43 (br s, 1 H), 7.81 (d, J=7.8 Hz, 1 H), 7.22–7.20 (m, 2 H), 6.75 (d, J=10.4 Hz, 1 H), 6.63 (dd, J=2.6, 8.3 Hz, 1 H), 6.57 (d, J=2.6 Hz, 1 H), 5.75 (d, J=10.4 Hz, 1 H), 2.86–2.73 (m, 2 H), 2.25 (apparent t, J=13.0 Hz, 1 H), 1.92 (apparent d, J=13.0 Hz, 1 H), 1.88–1.69 (m, 3 H), 1.55–1.44 (m, 2 H), 0.99 (s, 9 H), 0.21 (s, 3 H), 0.82 (t, J=7.8 Hz, 3 H), 0.20 (s, 3 H).

To a solution of (2S,4aR,10aR)-7-(tert-butyl-dimethylsilanyloxy)-4a-ethyl-2-pyridin-3-yl-1,2,4a,9,10,10a-hexahydrophenanthren-2-ol (90 mg, 0.21 mmol) in tetrahydrofuran was added a 1 M solution of borane in tetrahydrofuran (2 mL, 2.0 mmol). The mixture was allowed to stir for 3 days at room temperature and was then quenched with water and sodium perborate (923 mg, 6 mmol). After stirring for about 1 hour, the mixture was filtered, washing the precipitate with ethyl acetate. The filtrate was washed with brine, dried (MgSO$_4$) and concentrated to an oil from which (2R,3S,4aR,10aR)-7-(tert-butyl-dimethylsilanyloxy)-4a-ethyl-2-(pyridin-3-yl)-1,2,3,4,4a,9,10,10a-octahydrophenanthrene-2,3-diol (13 mg, 14%) was isolated as a white solid.

To a solution of (2R,3S,4aR,10aR)-7-(tert-butyl-dimethylsilanyloxy)-4a-ethyl-2-(pyridin-3-yl)-1,2,3,4,4a,9,10,10a-octahydrophenanthrene-2,3-diol (13 mg, 0.03 mmol) and acetic acid (0.05 mL, 0.87 mmol) in tetrahydrofuran (2 mL) was added a 1.0 M solution of tetrabutylammonium fluoride in tetrahydrofuran (0.13 mL, 0.13 mmol). The mixture was stirred overnight at room temperature and the concentrated under vacuum. The residue was taken up in ethyl acetate and filtered through a plug of silica gel. The title compound, a solid (4.2 mg, 43%) was obtained by evaporation of the solvent. $^1$H NMR (CDCl$_3$) selected signals: δ 9.00 (br s, 1 H), 8.50 (d, J=8.3 Hz, 1 H), 8.26 (d, J=5.7 Hz, 1 H), 7.32 (dd, J=5.7, 7.8 Hz, 1 H), 6.94 (d, J=8.3 Hz, 1 H), 6.65 (dd, J=2.6, 8.3 Hz, 1 H), 6.60 (d, J=2.6 Hz, 1 H), 4.23 (dd, J=4.7, 13.0 Hz, 1 H). MS: m/e 340 (M+1).

Example 28

(2R,3S,4aR,10aR)-4a-Ethyl-2-(4-fluorophenyl)-1,2,3,4,4a,9,10,10a-octahydrophenanthrene-2,3,7-triol

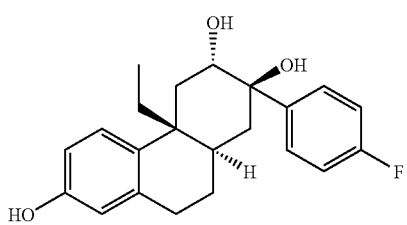

The title compound was prepared starting from the title compound of Preparation 5b in a manner analogous to that described for Example 27 using 4-fluorophenylmagnesium bromide in place of 3-pyridyllithium in the first step. Product was isolated by flash chromatography eluting with 55% diethyl ether in hexanes. $^1$H NMR (CDCl$_3$) selected signals: δ 7.80–7.77 (m, 2 H), 7.03–6.98 (m, 3 H), 6.58 (dd, J=2.6, 8.3 Hz, 1 H), 6.55 (d, J=2.6 Hz, 1 H), 4.16 (dd, J=4.2, 13.0 Hz, 1 H), 2.87–2.75 (m, 2 H), 2.66 (dd, J=4.2, 13.5 Hz, 1 H).

Example 29

(2R,3S,4aR,10aR)-4a-Ethyl-2-(4-fluorophenyl)-7-(2-methylpyridin-3-ylmethoxy)-1,2,3,4,4a,9,10,10a-octahydrophenanthrene-2,3-diol

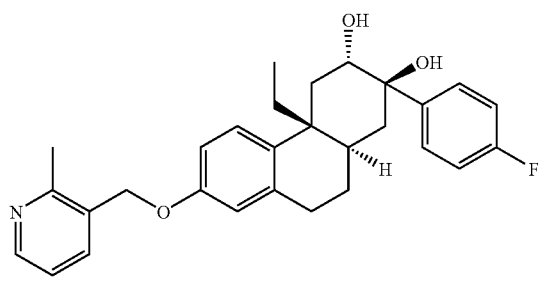

The title compound was prepared starting from the title product of Example 28 and 3-chloromethyl-2-methylpyridine hydrochloride using the same procedure outlined for Example 2. Product was isolated by flash chromatography eluting with 35% ethyl acetate in hexane. Mass spectrum: m/e 462 (M+1).

Example 30

(2R,3S,4aR,10aR)-4a-Benzyl-2-phenyl-1,2,3,4,4a,9,10,10a-octahydrophenanthrene-2,3,7-triol

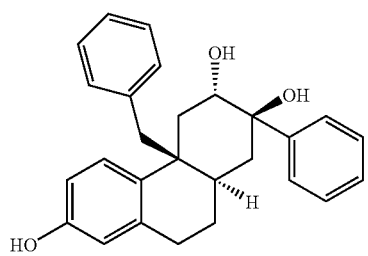

The title compound was prepared from (4aS,10aR)-4a-Benzyl-7-(tert-butyldimethylsilanyloxy)-4a,9,10,10a-tetrahydro-1H-phenanthren-2-one using a procedure analogous to that outlined for Example 27. (4aS,10aR)-4a-Benzyl-7-(tert-butyldimethylsilanyloxy)-4a,9,10,10a-tetrahydro-1H-phenanthren-2-one was prepared from (4aS,10aR)-4a-benzyl-7-hydroxy-3,4,4a,9,10,10a-hexahydro-1H-phenanthren-2-one using procedures analogous to those outlined in Preparations 3a, 5a and 5b. In turn, (4aS,10aR)-4a-benzyl-7-hydroxy-3,4,4a,9,10,10a-hexahydro-1H-phenanthren-2-one was obtained from 6-methoxy-2-tetralone using procedures analogous to those for Preparations 1a to 1f. Product was isolated by flash chromatography eluting with 5% methylene chloride in ethyl acetate. Mass spectrum: m/e 400 (M−1).

Example 31

(2R,3S,4aR,10aR)-4a-Benzyl-2-phenyl-7-(pyridin-4-ylmethoxy)-1,2,3,4,4a,9,10,10a-octahydrophenanthrene-2,3-diol

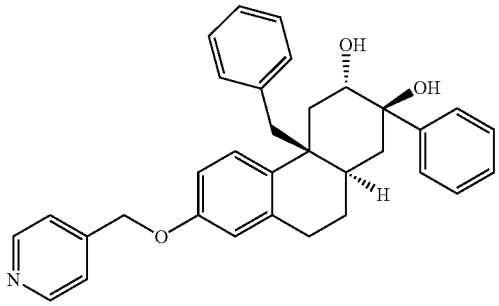

The title compound was prepared starting from the title product of Example 30 and 4-picolyl chloride hydrochloride using the same procedure outlined for Example 2. Product was purified by washing the crude product with hexane. Mass spectrum: m/e 492 (M+1).

Example 32

(2R,3S,4aR,10aR)-4a-Benzyl-7-(2-methylpyridin-3-ylmethoxy)-2-phenyl-1,2,3,4,4a,9,10,10a-octahydro-phenanthrene-2,3-diol

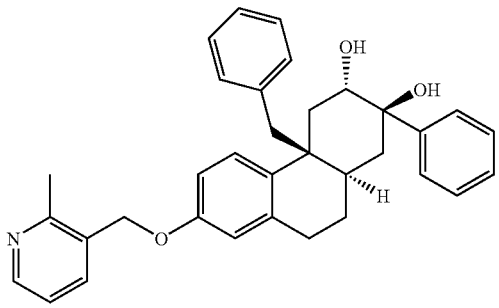

The title compound was prepared starting from the title product of Example 30 and 3-chloromethyl-2 methylpyridine hydrochloride using a procedure analogous to that outlined for Example 2. Product was isolated by flash chromatography eluting with 30% ethyl acetate in methylene chloride. Mass spectrum: m/e 506 (M+1).

Example 33

(6S,7R,4bR,8aR)-4b-Ethyl-6,7-dihydroxy-7-prop-1-ynyl-4b,5,6,7,8,8a,9,10-octahydro-phenanthrene-2-carbonitrile

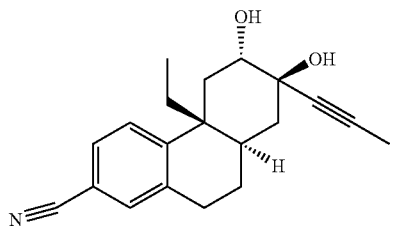

The title compound was prepared from the title product of Preparation 6e using a procedure analogous to that outlined for Example 1. Product was isolated by flash chromatography eluting with 40 to 50% ethyl acetate in hexane. (A little methylene chloride was used to help dissolve the crude sample.) $^1$H NMR (CDCl$_3$) selected signals: δ 3.63 (dd, J=4.2, 12.2 Hz, 1 H), 2.98–2.95 (m, 2 H), 2.60 (dd, J=4.2, 13.0 Hz, 1 H), 1.83 (s, 3 H).

Example 34

(6S,7R,4bR,8aR)-4b-Ethyl-6,7-dihydroxy-7-prop-1-ynyl-4b,5,6,7,8,8a,9,10-octahydro-phenanthrene-2-carboxylic acid (2-methylpyridin-3-ylmethyl)amide

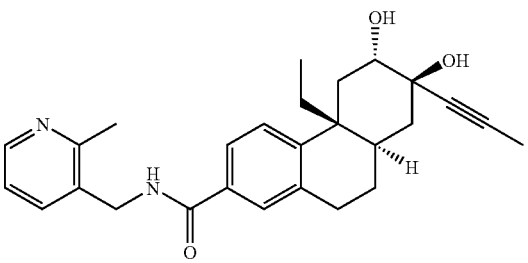

To a solution of the title compound of Example 33 (394 mg, 1.27 mmol) in ethanol (40 mL) was added 6 M aqueous sodium hydroxide solution. The mixture was warmed at 55° C. for 5 hours and then allowed to stand at room temperature for 4 days. The mixture was concentrated to remove most of the ethanol and the residue was taken up in excess aqueous 1 M hydrochloric acid solution. After extracting twice with ethyl acetate, the combined organic layers were washed with brine, dried (MgSO$_4$) and concentrated to a yellow solid. The product, (6S,7R,4bR,8aR)-4b-ethyl-6,7-dihydroxy-7-prop-1-ynyl-4b,5,6,7,8,8a, 9,10-octahydro-phenanthrene-2-carboxylic acid (191 mg, 46%) was isolated by triturating the crude solid with warm ethyl acetate and collecting by filtration. $^1$H NMR (CD$_3$OD) selected signals: δ 3.61 (dd, J=3.6, 12.2 Hz, 1 H), 3.03–3.00 (m, 2 H), 2.58 (dd, J=3.6, 13.0 Hz, 1 H), 1.80 (s, 3 H).

To a solution of (6S,7R,4bR,8aR)-4b-ethyl-6,7-dihydroxy-7-prop-1-ynyl-4b,5,6,7,8,8a,9,10-octahydro-phenanthrene-2-carboxylic acid (20 mg, 0.061 mmol) in tetrahydrofuran (2 mL) was added sequentially diisopropylethylamine (0.042 mL, 0.24 mmol), 1-[3-(dimethylamino)propyl]-3-ethyl carbodiimide (14 mg, 0.073 mmol), 1-hydroxybenzotriazole (9 mg, 0.064 mmol) and C-(2-methylpyridin-3-yl)-methylamine (0.025 mL, approximately 0.2 mmol). The mixture was stirred at room temperature for 1 day and was then quenched with saturated aqueous ammonium chloride solution. After extracting twice with ethyl acetate, the combined organic layers were washed with brine, dried (MgSO$_4$) and concentrated under vacuum. The title compound (10 mg, 38%) was isolated by flash chromatography eluting with 50% acetone in methylene chloride. Mass spectrum: m/e 433 (M+1).

Example 35

(2R,3S,4aR,10aR)-2-(2,6-difluorophenyl)-4a-ethyl-1,2,3,4,4a,9,10,10a-octahydrophenanthrene-2,3,7-triol

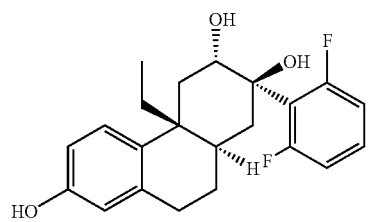

A solution of the crude compound of Preparation 8a (410 mg, 0.69 mmol) in a 1:1 dichloromethane/methanol mixture (35 mL) at −78° C. was purged with ozone until saturated (dark blue) and stirred for 3 hours while occasionally purging with ozone to maintain a blue color. The mixture was purged with nitrogen and dimethylsulfide (2 mL) was added. The mixture was allowed to warm to room temperature, stirred for 16 hours and then concentrated to a white solid. The solid was dissolved in tetrahydrofuran and lithium borohydride (65 mg, 2.98 mmol) was added. After 2 hours, aqueous 1 N hydrochloric acid solution (5 mL) and water (50 mL) were added, and the mixture was extracted with ethyl acetate (3×50 mL). The combined organic layers were washed with brine, dried (MgSO$_4$), filtered and concentrated to a paste (375 mg). The residue was purified by flash chromatography using a 30% to 50% ethyl acetate/hexanes eluant to afford an oil 38 mg (17%). The oil was crystallized in ethyl ether and hexanes to afford the title compound as beige solid (15 mg). Melting Point 198–200° C. Mass spectrum (m/e) 373 (M$^+$−1, −ion).

Examples 36–38

The compounds of Examples 36–38 were prepared according to the procedure of Example 35, substituting the compounds of Preparations 8b and 8c, respectively, for the compound of Preparation 8a. The compound of Example 38 is a product of over oxidation obtained during formation of the compound of Example 37.

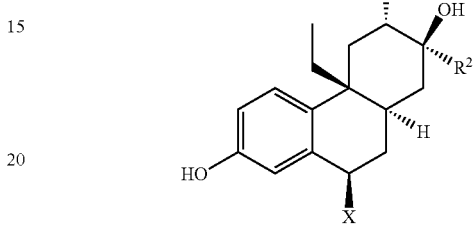

| Example | R$_2$ | X | MP (° C.) | Mass Spectral Data |
|---|---|---|---|---|
| 36 | 2,6-dimethoxyphenyl | H | oil | MS (m/e) 381 (M$^+$ + 1 —H$_2$O, +ion) |
| 37 | 2-methoxyphenyl | H | 131–134 | MS (m/e) 351 (M$^+$ + 1 —H$_2$O, +ion) |
| 38 | 2-methoxyphenyl | O H | 137–141 | MS (m/e) 367 (M$^+$ + 1 —H$_2$O, +ion) |

Example 39

(2R,3S,4aR,9R,10aR)-4a-Ethyl-2-phenyl-1,2,3.4,4a,9,10,10a-octahydro-phenanthrene-2,3,7,9-tetraol

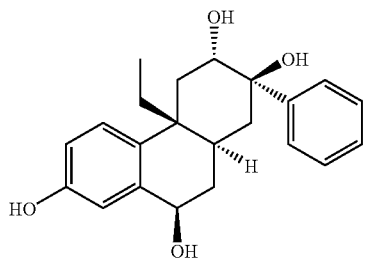

The compound of Example 39 was prepared according to the procedure of Example 16 substituting the compound of Preparation 4f for the compound of Preparation 4e. The residue was triturated with ethyl ether to afford the title compound as a solid. Melting Point: 185–187° C. Mass spectrum: (m/e) 353 (M$^+$−1, −ion).

Example 40

(2R,3S,4aR,10aS)-4a-Ethyl-2,3,7-trihydroxy-2-phenyl-2,3,4,4a,10,10a-hexahydro-1H-phenanthren-9-one

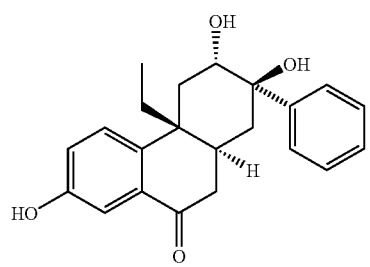

A mixture of the compound of Example 39 (38 mg, 0.11 mmol) and manganese(IV) oxide (92 mg, 1.1 mmol) in 1:2 acetone/toluene (30 mL) was heated to reflux using a Dean-Stark trap apparatus. The initial distillate containing acetone was removed from the trap, and the pot was heated at reflux for 48 hours. During this time, additional manganese(IV) oxide (50 mg) was added in two portions. The mixture was filtered hot and concentrated, and the residue was purified by HPLC to afford 1.6 mg of the title compound. Mass spectrum: (m/e) 353 (M$^+$+1, +ion).

Example 41

(2R,3S,4aR,10aR)-3-Amino-4a-ethyl-2-phenyl-1,2,3,4,4a,9,10,10a-octahydro-phenanthrene-2,7-diol

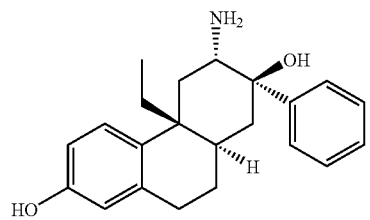

A mixture of the compound of Preparation 4e (0.10 g, 0.30 mmol), ammonium chloride (636 mg, 11.9 mmol), and sodium borohydride (94 mg, 1.5 mmol) in 10 mL of methanol was stirred over 3 Å molecular sieves for 20 days during which additional sodium borohydride (94 mg, 180 mg) was added on the eighth day. A saturated sodium bicarbonate solution (30 mL) was added and the mixture concentrated to about 30 mL and extracted with ethyl acetate (3×30 mL). The combined organic layers were washed with brine, dried (MgSO$_4$), filtered and concentrated to an oil (98 mg), which was purified by HPLC to afford a solid. The solid was dissolved in tetrahydrofuran, treated with a MP-carbonate resin for 40 minutes, filtered and concentrated to afford 35 mg of the title compound as a white solid. Melting Point: 209–210° C. Mass spectrum: (m/e) 337 (M$^+$, −ion).

Examples 42 and 43

(2R,3R,4aR,10aR)-4a-Ethyl-3-methyl-2-phenyl-1,2,3,4,4a,9,10,10a-octahydro-phenanthrene-2,3,7-triol and (2R,3S,4aR,10aR)-4a-Ethyl-3-methyl-2-phenyl-1,2,3,4,4a,9,10,10a-octahydro-phenanthrene-2,3,7-triol Example 42

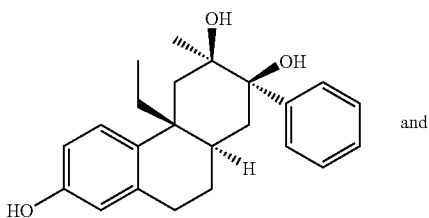

and

Example 43

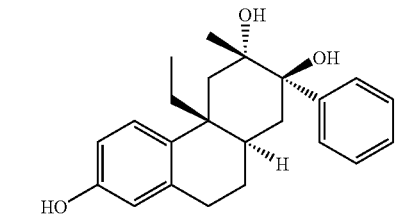

To a solution of the compound of Preparation 4e (0.12 g, 0.36 mmol) in 5 mL of tetrahydrofuran at −78° C. was added a 1.5 M solution of methyllithium-lithium iodide in ethyl ether (2.2 mL, 2.16 mmol). The mixture was stirred at 0° C. for 3 hours, and 1N hydrochloric acid and 30 mL of water were added. The mixture was extracted with ethyl acetate (3×30 mL), and the combined organic layers were washed with brine, dried (MgSO$_4$), filtered and concentrated to an oil (118 mg). This residue was crystallized in chloroform to afford 60 mg (47%) of the 3-R title compound (Example 42) as a solid, melting point: 197–199° C. The mother liquor was purified by flash chromatography using a 40% to 60% ethyl ether/hexanes eluant to afford 15 mg (12%) of the 3-R title compound (Example 42) and 6 mg (5%) of the 3-S title compound (Example 43) as a white solid, melting point: 228–229° C. Example 44: (3-R) Analytical calculated for $C_{23}H_{28}O_3$: C, 78.38; H, 8.01. Found: C, 78.03; H, 7.91. Example 45 (3-S): Analytical calculated for $C_{23}H_{28}O_3$: C, 78.38; H, 8.01. Found: C, 78.17; H, 8.29.

Examples 44–47

The compounds of Examples 44–47 were prepared according to the procedure of Example 42 substituting the compound of Preparation 4f for the compound of Preparation 4e. The crude mixture was purified by HPLC.

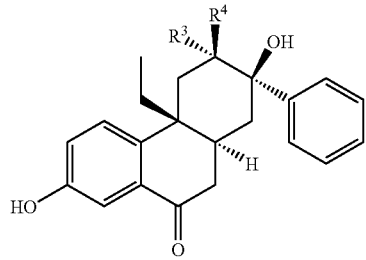

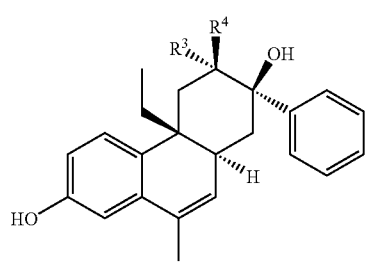

| Example | R³ | R⁴ | Structure | M.P. (° C.) | Mass Spectral Data |
| --- | --- | --- | --- | --- | --- |
| 44 | Me | OH | I | 148–150 | MS (m/e) 365 (M⁺, –ion) |
| 45 | OH | Me | II |  | MS (m/e) 363 (M⁺, –ion) |
| 46 | Me | OH | II | 257–260 | MS (m/e) 363 (M⁺, –ion) |
| 47 | OH | Me | I |  | MS (m/e) 365 (M⁺, –ion) |

Examples 48 to 53

The compounds of Examples 48 to 53 were prepared according to the procedure of Examples 42 and 43 substituting ethylmagnesium bromide, 2-propyllithium, cyclopropyllithium, and vinyllithium for methyllithium. In the case of ethylmagnesium bromide, lithium chloride (10 equivalents) was added prior to the addition of the organometallic reagent. The compounds of Example 51 and 53 were obtained as by-products in the reaction of ethylmagnesium bromide (18% yield) and vinyllithium (28% yield), respectively.

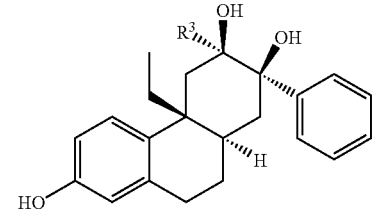

| Example | R³ | MP (° C.) | Mass Spectral Data |
| --- | --- | --- | --- |
| 48 | ethyl | amorphous | MS (m/e) 365 (M⁺ – 1, –ion) |
| 49 | 2-propyl | 236–237 | |

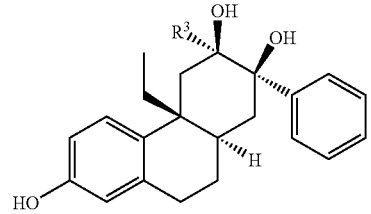

| Example | R³ | MP (° C.) | Mass Spectral Data |
| --- | --- | --- | --- |
| 50 | cyclopropyl | 149–150 | MS (m/e) 377 (M⁺ – 1, –ion) |
| 51 | H | 207–209 | |
| 52 | vinyl | amorphous | MS (m/e) 363 (M⁺ – 1, –ion) |
| 53 | ethynyl | amorphous | MS (m/e) 361 (M⁺ – 1, –ion) |

Examples 54 and 55

The compounds of Examples 54 and 55 were prepared according to the procedure of Example 42 substituting the compound of Preparation 9 for the compound of Preparation 4e and substituting phenyllithium for methyllithium in the case of the compound of Example 55.

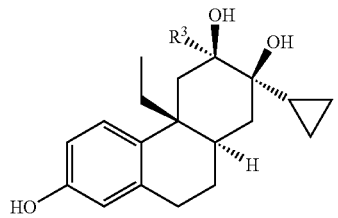

| Example | R³ | MP (° C.) | Mass Spectral Data |
| --- | --- | --- | --- |
| 54 | methyl | 206–207 | MS (m/e) 315 (M⁺ – 1, –ion). |
| 55 | phenyl | foam | MS (m/e) 361 (M⁺ – 1, –ion). |

Example 56

(2R,3S,4aR,10aR)-2-(2,6-Difluoro-phenyl)-4a-ethyl-7-(2-methyl-pyridin-3-ylmethoxy)-1,2,3,4,4a,9,10,10a-octahydro-phenanthrene-2,3-diol

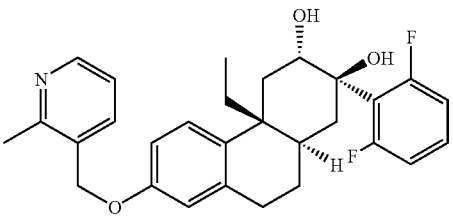

A mixture of the compound of Example 35 (35 mg, 0.093 mmol), sodium hydride 60% (20 mg, 0.5 mmol) and 3-chloromethyl-2-methyl-pyridine hydrochloride (23 mg, 0.13 mmol) in 3 mL of dimethylformamide (DMF) was stirred overnight. Saturated aqueous ammonium chloride solution (5 mL) and water (15 mL) were added and the mixture extracted with ethyl acetate (3×20 mL). The combined organic layers were washed with brine, dried (MgSO₄), filtered and concentrated to a oil (35 mg). The residue was purified by flash chromatography using a 50% to 80% ethyl acetate/hexanes eluant to afford 20 mg (44%) of the title compound as an oil, which was crystallized from hexanes to give a white solid. Melting point: 80–83° C. Mass spectrum: (m/e) 461(M⁺–H₂O, +ion).

Example 57

(2R,3R,4aR,10aR)-4a-Ethyl-3-methyl-7-(2-methyl-pyridin-3-ylmethoxy)-2-phenyl-1,2,3,4,4a,9,10,10a-octahydro-phenanthrene-2,3-diol

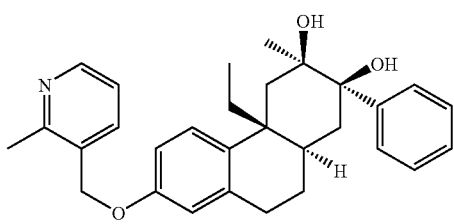

A mixture of the compound of Example 42 (0.20 g, 0.57 mmol), cesium carbonate (2.0 g, 5.7 mmol) and 3-chloromethyl-2-methyl-pyridine hydrochloride (0.16 g, 0.91 mmol) in a 2:1 THF/DMF mixture was heated at 80° C. for 15 hours. The cooled mixture was filtered and concentrated, and then water (30 mL) was added and the mixture extracted with ethyl acetate (3×30 mL). The combined organic layers were washed with brine, dried (MgSO₄), filtered and concentrated to a foam (0.31 g). The residue was purified by flash chromatography using a 30% to 70% ethyl acetate/hexanes eluant to afford 122 mg (47%) of the title compound as an oil. Mass spectrum: (m/e) 458 (M⁺+1, +ion).

Examples 58–68

The compounds of Examples 58–68 were prepared according to the procedure of Example 57 substituting commercially available halides for 3-chloromethyl-2-methyl-pyridine hydrochloride. The compounds were obtained as amorphous solids except for the compound of Example 68, which was a white solid. Melting point: 159–163° C.

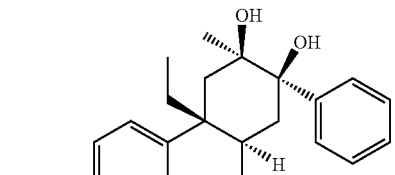

| Example | R⁵ᵃ | Mass Spectral Data |
|---|---|---|
| 58 | Methyl | MS (m/e) 349 (M⁺ + 1 —H₂O, +ion) |
| 59 | (CH₂)₂OH | MS (m/e) 379 (M⁺ + 1 —H₂O, +ion) |
| 60 | (CH₂)₃OH | MS (m/e) 393 (M⁺ + 1 —H₂O, +ion) |
| 61 | (CH₂)₄OH | MS (m/e) 425 (M⁺ + 1, +ion) |
| 62 | CH₂CO₂Et | MS (m/e) 421 (M⁺ + 1 —H₂O, +ion) |
| 63 | (CH₂)₃CO₂Me | MS (m/e) 435 (M⁺ + 1 —H₂O, +ion) |
| 64 | (CH₂)₄CO₂Me | MS (m/e) 449 (M⁺ + 1 —H₂O, +ion) |
| 65 | CH₂CN | MS (m/e) 390 (M⁺ – 1, +ion) |
| 66 | (CH₂)₃CN | MS (m/e) 402 (M⁺ + 1 —H₂O, +ion) |
| 67 | (CH₂)₄CN | MS (m/e) 416 (M⁺ + 1 —H₂O, +ion) |
| 68 | CH₂CONH₂ | MS (m/e) 408 (M⁺‘+ 1 —H₂O, –ion) |

Example 69

(2R,3R,4aR,10aR)-4a-Ethyl-7-(3-hydroxy-propoxy)-3-methyl-2-phenyl-1,2,3,4,4a,9,10,10a-octahydro-phenanthrene-2,3-diol

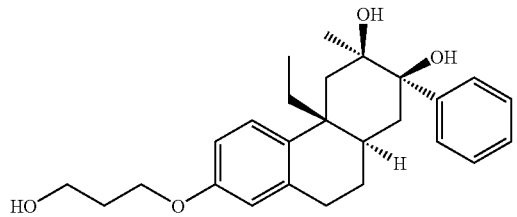

To a solution of 51 mg (0.097 mmol) of the compound of Preparation 10 in 2 mL of dichloromethane was added 0.3 mL (0.3 mmol) of a 1.0 M solution of tetrabutylammonium fluoride in tetrahydrofuran. After stirring at room temperature for 16 hours, the mixture was partitioned between 25 mL of water and 25 mL of ethyl acetate. The ethyl acetate layer was extracted with water (2×25 mL) and brine (25 mL), dried (Na₂SO₄), and concentrated. The oil residue was purified by flash chromatography using a 3:1 hexanes/ethyl acetate eluant to afford 16 mg of the title compound as an amorphous solid. Mass spectrum: (m/e) 393 (M⁺+1–H₂O, +ion).

Example 70

(4bR,6R,7R,8aR)-(4b-Ethyl-6,7-dihydroxy-6-methyl-7-phenyl-4b,5,6,7,8,8a,9,10-octahydro-phenanthren-2-yloxy)-acetic acid

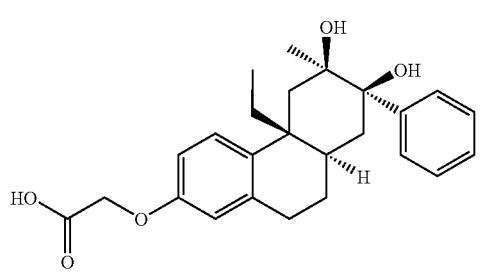

The compound of Example 62 (23 mg, 0.052 mmol) was dissolved in 3 mL of a 1:1:2 mixture of 2 N lithium hydroxide/ethanol/tetrahydrofuran and stirred for 1 hour. 1 N Hydrochloric acid solution was added and the mixture was concentrated to about 1 mL. The residue was diluted with water (3 mL) and extracted with ethyl acetate (3×3 mL). The combined organic layers were washed with brine, dried ($Na_2SO_4$), filtered and concentrated to afford 18 mg (82%) of the title compound as a solid. Melting point: 190–191° C. Mass spectrum: (m/e) 409 ($M^+$–1, –ion).

Examples 71 and 72

The compounds of Examples 71 and 72 were prepared according to the procedure of Example 70 substituting the compounds of Example 63 and 64 for the compound of Example 62.

| Example | N | MP (° C.) | Mass Spectral Data |
|---|---|---|---|
| 71 | 3 | | MS (m/e) 437 ($M^+$ –1, –ion) |
| 72 | 4 | 191–192 amorphous | MS (m/e) 451 ($M^+$ –1, –ion) |

Example 73

(2R,3R,4aR,10aR)-4a-Ethyl-7-(2-hydroxy-2-methyl-propoxy)-3-methyl-2-phenyl-1,2,3,4,4a,9,10,10a-octahydro-phenanthrene-2,3-diol

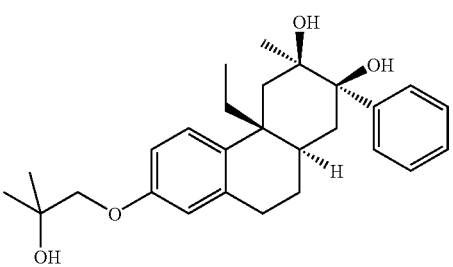

To a solution of the compound of Example 62 (36 mg, 0.082 mmol) in 5 mL of tetrahydrofuran was added a 1.5 M solution of methyllithium-lithium iodide in ethyl ether (0.55 mL, 0.82 mmol). The mixture was stirred for 3 hours and then 1N hydrochloric acid solution and 30 mL of water were added. The mixture was extracted with ethyl acetate (3×30 mL), and the combined organic layers were washed with brine, dried ($MgSO_4$), filtered and concentrated to afford 44 mg (100%) of the title compound as a white solid. Melting Point: 190–193° C. Mass spectrum: (m/e) 423 ($M^+$–1, –ion).

Examples 74 and 75

The compounds of Examples 74 and 75 were prepared according to the procedure of Example 73 substituting the compounds of Example 63 and 64, respectively, for the compound of Example 62.

| Example | n | MP (° C.) | Mass Spectral Data |
|---|---|---|---|
| 74 | 3 | 123–124 | |
| 75 | 4 | oil | MS (m/e) 451 ($M^+$ – 1, –ion) |
| | | | MS (m/e) 449 ($M^+$ – 18 + 1, +ion) |

Example 76

(2R,3R,4aR,10aR)-4a-Ethyl-3-methyl-2-phenyl-7-(1H-tetrazol-5-ylmethoxy)-1,2,3,4,4a,9,10,10a-octahydro-phenanthrene-2,3-diol

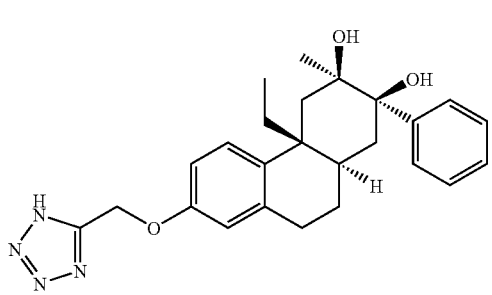

To a solution of the compound of Example 65 (28 mg, 0.072 mmol) in 1 mL of dimethylformamide (DMF) was added sodium azide (46 mg, 0.72 mmol) and ammonium chloride (39 mg, 0.72 mmol). The mixture was heated in a sealed tube at 120° C. overnight and then concentrated to an oil. 1N Hydrochloric acid solution (3 mL) was added and the mixture was extracted with ethyl acetate (3×3 mL). The combined organic layers were washed with brine, dried (Na$_2$SO$_4$), filtered and concentrated to an oil. The residue was purified by HPLC to afford 6 mg (19%) of the title compound as a white solid. Melting point: 108–110° C. Mass spectrum: (m/e) 435 (M$^+$+1, +ion).

Examples 77 and 78

The compounds of Examples 77 and 78 were prepared according to the procedure of Example 76 substituting the compounds of Example 66 and 67 for the compound of Example 65.

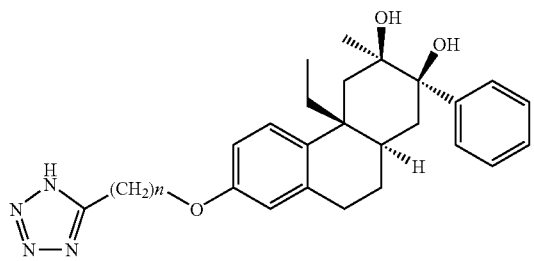

| Example | n | MP (° C.) | Mass Spectral Data |
|---|---|---|---|
| 77 | 3 | 112–115 | MS (m/e) 461 (M$^+$ − 1, −ion) |
| 78 | 4 | 160–163 | MS (m/e) 477 (M$^+$ + 1, −ion) |

Example 79

(4bR,6R,7R,8aR)N-(3-Cyano-propyl)-2-(4b-ethyl-6,7-dihydroxy-6-methyl-7-phenyl-4b,5,6,7,8,8a,9,10-octahydro-phenanthren-2-yloxy)-acetamide

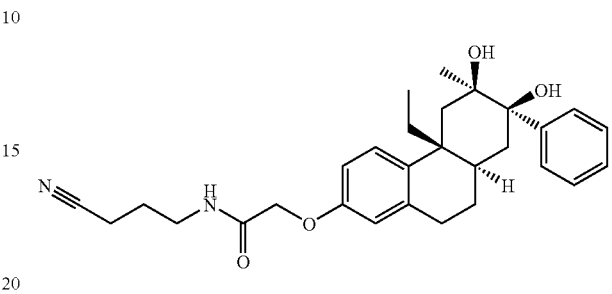

The compound of Example 79 was prepared according to the procedure of Example 57 substituting 3-bromoproprionitrile for 3-chloromethyl-2-methyl-pyridine hydrochloride and substituting the compound of Example 68 for the compound of Example 42. Melting Point: 185–186° C. Mass spectrum: (m/e) 445 (M$^+$−18+1, +ion).

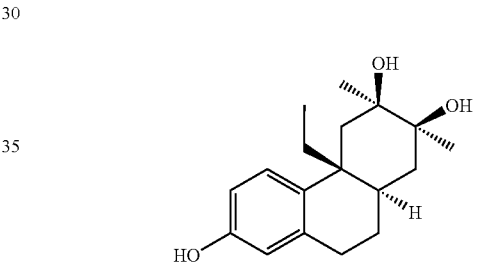

To a solution of the compound of Preparation 11e (50 mg, 0.18 mmol) in 10 mL of tetrahydrofuran at −30° C. was added a 1.0 M solution of methyl lithium-lithium iodide in ethyl ether (1.1 mL, 1.1 mmol). The mixture was stirred and allowed to warm to room temperature overnight. 1N Aqueous hydrochloric acid solution (10 mL) was added, and the separated aqueous layer was extracted with ethyl acetate (10 mL). The combined organic layers were dried (MgSO$_4$), filtered and concentrated. The residue was purified by flash chromatography using a 20% to 40% ethyl acetate/hexanes mixture as eluant to afford 21 mg (40%) of the title compound. Mass spectrum: (m/e) 289 (M$^+$−1, −ion).

Examples 81–89

The compounds of Examples 81–89 were prepared as solids according to the procedure of Example 80 substituting vinylmagnesium bromide, isopropylmagnesium chloride, propynylmagnesium bromide, p-tolylmagnesium bromide, E-propenylmagnesium bromide, ethylmagnesium bromide, n-propylmagnesium chloride, n-butyllithium, and allylmagnesium bromide for methyllithium, respectively. The compounds were directly purified by HPLC, except for Examples 81 and 86. The compound of Example 85 was triturated in ether and had a melting point of 213–214° C. The compounds of Examples 81 and 86 were 1:1 and 3:1 mixture of diastereomers at C2.

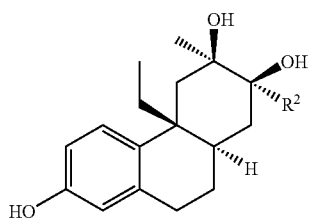

| Example | R² | Mass Spectral Data |
|---|---|---|
| 81 | vinyl | MS (m/e) 301 (M⁺ − 1, −ion) |
| 82 | isopropyl | MS (m/e) 317 (M⁺ − 1, −ion) |
| 83 | propynyl | MS (m/e) 313 (M⁺ − 1, −ion) |
| 84 | p-tolyl | MS (m/e) 365 (M⁺ − 1, −ion) |
| 85 | E-propenyl | MS (m/e) 315 (M⁺ − 1, −ion) |
| 86 | ethyl | MS (m/e) 303 (M⁺ − 1, −ion) |
| 87 | n-propyl | MS (m/e) 301 (M⁺ − 18 + 1, +ion) |
| 88 | n-butyl | MS (m/e) 331 (M⁺ − 1, −ion) |
| 89 | allyl | MS (m/e) 315 (M⁺ − 1, −ion) |

Example 90

(2R,3R,4aR,10aR)-7-(5-Dimethylaminomethyl-[1,2,4]oxadiazol-3-ylmethoxy)-4a-ethyl-3-methyl-2-phenyl-1,2,3,4,4a,9,10,10a-octahydro-phenanthrene-2,3-diol

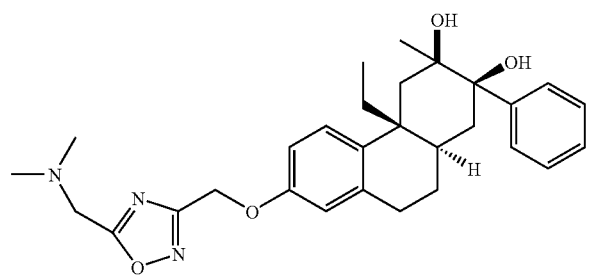

To a solution of the compound of Example 65 (350 mg, 0.89 mmol) in tetrahydrofuran (25 mL) was added hydroxylamine hydrochloride (208 mg, 3 mmol) and diisopropylethylamine (0.52 mL, 3.0 mmol). The mixture was heated to reflux overnight and concentrated under vacuum. The N-hydroxyamidine product (343 mg, 90%) was isolated by flash chromatography eluting with a gradient of 50% ethyl acetate in hexane to 100% ethyl acetate.

To a solution of the intermediate N-hydroxyamidine (34 mg, 0.08 mmol) in tetrahydrofuran (4 mL) was added sodium hydride (6 mg, 0.25 mmol). The mixture was stirred at 60° C. for 45 minutes. N,N-Dimethylglycine ethyl ester (0.03 mL, 0.2 mmol) was then added and heating at 60° C. was resumed for an additional 2 hours. After the mixture was cooled, ether was added and the precipitated solid was removed by filtration. The filtrate was concentrated to give a yellow oil. The title compound (4 mg) was isolated by preparative HPLC on a 19×50 mm reverse phase column using 5% to 80% acetonitrile/water (0.1% formic acid) to elute. Mass spectrum (m/e) 492 (M⁺+1).

Example 91

(2R,3R,4aR,10aR)-4a-Ethyl-3-methyl-7-[5-(2-morpholin-4-ylethyl)-[1,2,4]oxadiazol-3-ylmethoxy]-2-phenyl-1,2,3,4,4a,9,10,10a-octahydrophenanthrene-2,3-diol

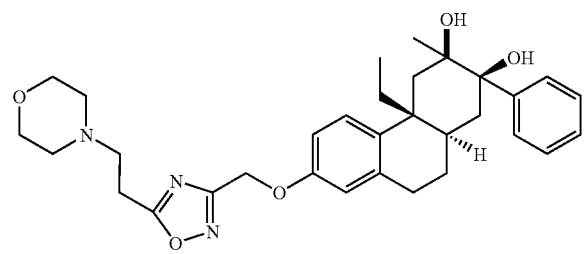

The title compound was prepared from the compound of Example 65 according to the procedure of Example 90 using ethyl 3-(4-morpholino) propionate ethyl ester in place of N,N-dimethylglycine in the condensation with the N-hydroxyamidine. Mass spectrum (m/e) 548 (M⁺+1).

Example 92

(2R,3R,4aR,10aR)-7-[5-(2-Dimethylaminoethyl)-[1,2,4]oxadiazol-3-ylmethoxyl-4a-ethyl-3-methyl-2-phenyl-1,2,3,4,4a,9,10,10a-octahydrophenanthrene-2,3-diol (CE-122761)

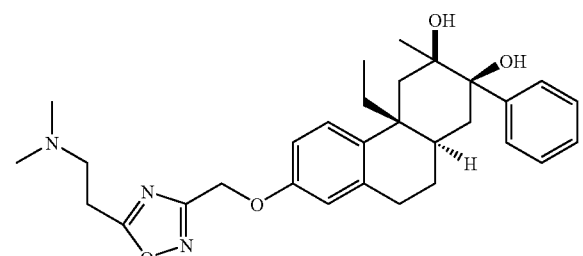

The title compound was prepared from the compound of Example 65 according to the procedure of Example 90 using ethyl 3-(N,N-dimethylamino) propionate ethyl ester in place of N,N-dimethylglycine in the condensation with the N-hydroxyamidine. Mass spectrum (m/e) 506 (M⁺+1).

Example 93

(2R,3R,4aR,10aR)-4a-Ethyl-3-methyl-2-phenyl-7-[5-(2-piperidin-1-ylethyl)-[1,2,4]oxadiazol-3-yl-methoxy]-1,2,3,4,4a,9,10,10a-octahydrophenan-threne-2,3-diol

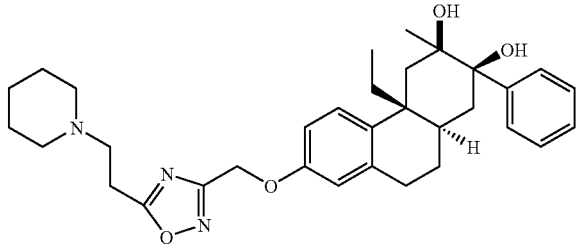

The title compound was prepared from the compound of Example 65 according to the procedure of Example 90 using ethyl 3-(1-piperidyl) propionate ethyl ester in place of N,N-dimethylglycine in the condensation with the N-hydroxyamidine. Mass spectrum (m/e) 546 (M$^+$+1).

Example 94

(4bR6R,7R,8aR)-N-[3-(4b-Ethyl-6,7-dihydroxy-6-methyl-7-phenyl-4b,5,6,7,8,8a,9,10-octahydro-phenanthren-2-yloxymethyl)-[1,2,4]oxadiazol-5-ylmethyl]-acetamide

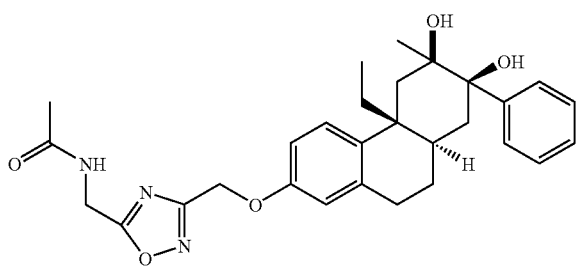

The title compound was prepared from the compound of Example 65 according to the procedure of Example 90 using ethyl acetamidoacetate ethyl ester in place of N,N-dimethylglycine in the condensation with the N-hydroxyamidine. Mass spectrum (m/e) 488 (M$^+$+1 minus H$_2$O).

Example 95

(2R,3R,4aR,10aR)-4a-Ethyl-3-methyl-7-[5-(1-methyl-1H-pyrrol-2-ylmethyl)-[1,2,4]oxadiazol-3-yl-methoxy]-2-phenyl-1,2,3,4,4a,9,10,10a-octahydro-phenanthrene-2,3-diol

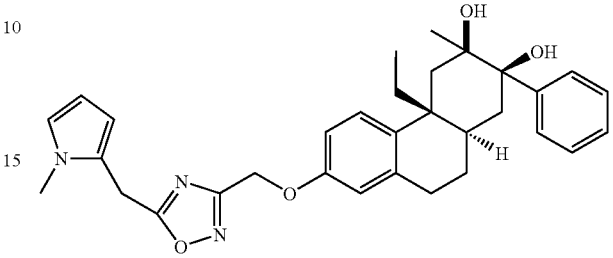

The title compound was prepared from the compound of Example 65 according to the procedure of Example 90 using methyl 2-(1-methylpyrrol-2-yl)acetate ethyl ester in place of N,N-dimethylglycine in the condensation with the N-hydroxyamidine. Mass spectrum (m/e) 528 (M$^+$+1).

Example 96

(4bR6R,7R,8aR)-2-(4b-Ethyl-6,7-dihydroxy-6-methyl-7-phenyl-4b,5,6,7,8,8a,9,10-octahydro-phenanthren-2-yloxy)-1-morpholin-4-yl-ethanone

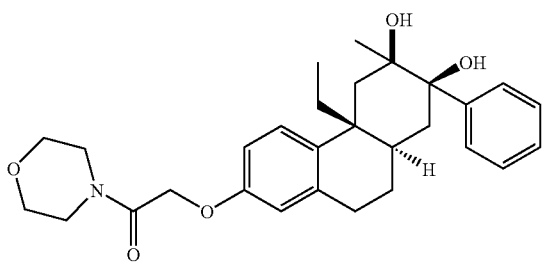

The title compound was prepared from the compound of Example 42 according to the procedure of Example 57 using 4-(2-chloroacetyl)morpholine as the alkylating agent and stirring the reaction at room temperature overnight. Mass spectrum (m/e) 480 (M$^+$+1).

Example 97

(4bR6R,7R,8aR)-2-(4b-Ethyl-6,7-dihydroxy-6-methyl-7-phenyl-4b,5,6,7,8,8a,9,10-octahydrophenan-thren-2-yloxy)-1-(4-methyl-piperazin-1-yl)-ethanone

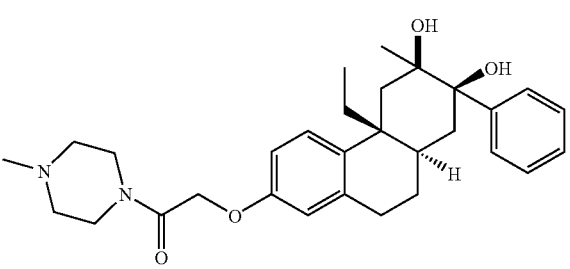

To a solution of the compound of Example 70 (25 mg, 0.07 mmol) in dichloromethane (3 mL) was added hydroxybenztriazole (10 mg, 0.073 mmol), 1-methylpiperazine (0.008 mL, 0.073 mmol), diisopropylethylamine (0.017 mL, 0.1 mmol) and 1-[3-(dimethylamino)propyl]-3-ethylcarbodiimide hydrochloride (14 mg, 0.073 mmol). The mixture was stirred at room temperature for 4 days and then quenched with saturated aqueous ammonium chloride solution. After the mixture was diluted with water, it was extracted with dichloromethane. The organic layer was dried over magnesium sulfate and concentrated. The title compound was isolated by flash chromatography eluting with a gradient of 30% ethyl acetate in hexane to 100% ethyl acetate. Mass spectrum (m/e) 493 ($M^+$+1).

Example 98

(4bR6R,7R,8aS)-2-(4b-Ethyl-6,7-dihydroxy-6-methyl-7-phenyl-4b,5,6,7,8,8a,9,10-octahydrophenanthren-2-yloxy)-N-pyridin-4-ylmethylacetamide

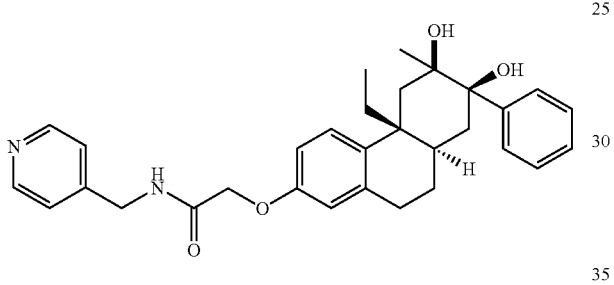

The title compound was prepared from the compound of Example 70 according to the procedure of Example 97 using 4-(aminomethyl)pyridine in place of 1-methylpiperazine. Mass spectrum (m/e) 501 ($M^+$+1).

Example 99

(2R,3R,4aR,10aR)-4a-Ethyl-3-methyl-7-(2-morpholin-4-yl-ethoxy)-2-phenyl-1,2,3,4,4a,9,10,10a-octahydrophenanthrene-2,3-diol

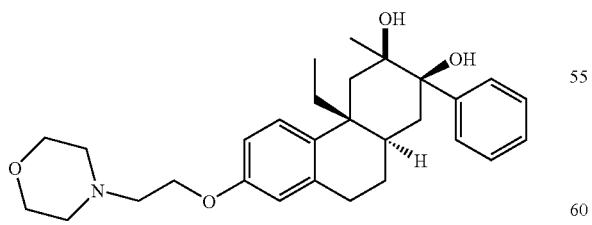

The title compound was prepared from the compound of Example 42 according to the procedure of Example 57 using 4-(2-chloroethyl)morpholine as the alkylating agent and stirring the reaction at room temperature for 14 days. Mass spectrum (m/e) 466 ($M^+$+1).

Example 100

(2R,3R,4aR,10aR)-4a-Ethyl-3-methyl-2-phenyl-7-(2-piperidin-1-yl-ethoxy)-1,2,3,4,4a,9,10,10a-octahydrophenanthrene-2,3-diol

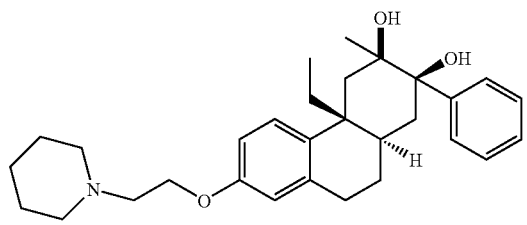

The title compound was prepared from the compound of Example 42 according to the procedure of Example 57 using N-(2-chloroethyl)piperidine as the alkylating agent and stirring the reaction at room temperature for 3 days. Mass spectrum (m/e) 464 ($M^+$+1).

Example 101

(2R,3R,4aR,10aR)-4a-Ethyl-2,3-dihydroxy-3-methyl-7-(2-methylpyridin-3-ylmethoxy)-2-phenyl-2,3,4,4a,10,10a-hexahydro-1H-phenanthren-9-one

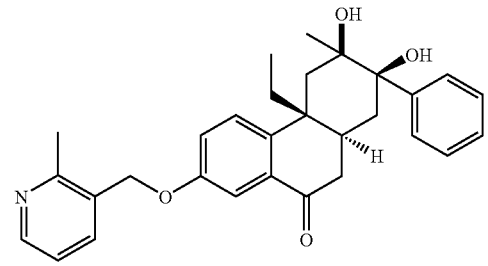

The title compound was prepared from the compound of Example 44 according to the procedure of Example 57 running the reaction at room temperature overnight. Mass spectrum (m/e) 472 ($M^+$+1).

Example 102

(2R,3R,4aR,10aR)-4a-Ethyl-3-methyl-2-pyridin-2-yl-1,2,3,4,4a,9,10,10a-octahydrophenanthrene-2,3,7-triol

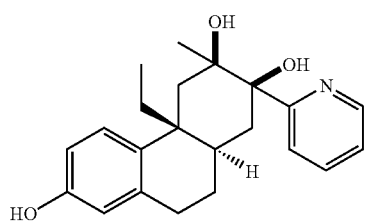

A solution of the compound of Preparation 12d (1.43 grams, 4.36 mmol) in 1,2-dimethoxyethane (300 mL) was cooled to −30° C. A 1.6 M solution of methyllithium in diethyl ether (33 mL, 52 mmol) was added dropwise and the mixture was allowed to stir from −30° C. to room temperature overnight. Additional 1.6 M methyllithium solution (10 mL, 16 mmol) and 1,2-dimethoxyethane (80 mL) were added and the mixture was allowed to stir overnight again. The mixture was quenched with saturated aqueous ammonium chloride solution. After the addition of saturated aqueous sodium bicarbonate solution and water, the mixture was extracted twice with ethyl acetate. The combined extracts were washed with brine, dried over magnesium sulfate and concentrated. The title compound (621 mg, 40%) was isolated by chromatography on silica gel eluting with a gradient of 20% to 50% ethyl acetate in hexane. Mass spectrum (m/e) 354 (M$^+$+1).

Example 103

(2R,3R,4aR,10aR)-4a-Ethyl-3-methyl-2-pyridin-3-yl-1,2,3,4,4a,9,10,10a-octahydrophenanthrene-2,3,7-triol

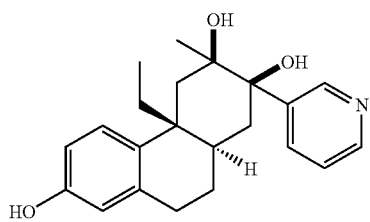

(2R,4aR,10aR)-4a-Ethyl-2,7-dihydroxy-2-pyridin-3-yl-1,4,4a,9,10,10a-hexahydro-2H-phenanthren-3-one was prepared from the compound of Preparation 12a and 3-bromopyridine by a sequence of reactions analogous to Preparations 12b–d.

A solution of (2R,4aR,10aR)-4a-Ethyl-2,7-dihydroxy-2-pyridin-3-yl-1,4,4a,9,10,10a-hexahydro-2H-phenanthren-3-one (30 mg, 0.09 mmol) in tetrahydrofuran (8 mL) was cooled to 0° C. A 1.0 M solution of methyllithium/lithium iodide complex in tetrahydrofuran (0.43 mL, 0.43 mmol) was added and the mixture was allowed to stir from 0° C. to room temperature over 5 hours. The solution was cooled to 0° C. and additional 1.0 M methyllithium/lithium iodide solution (0.2 mL, 0.2 mmol) was added. After the mixture was allowed to stir overnight at room temperature, it was again cooled to 0° C. and more methyllithium/lithium iodide solution (0.3 mL, 0.3 mmol) was added. After stirring the mixture for a further 4 hours at room temperature, it was quenched with water and saturated aqueous ammonium chloride solution. The mixture was extracted six times with ethyl acetate, and the combined extracts were washed with brine, dried over magnesium sulfate and concentrated. The title compound (2 mg, 6%) was isolated by chromatography on silica gel eluting with a gradient of 2% to 10% methanol in chloroform. Mass spectrum (m/e) 354 (M$^+$+1).

Example 104

(2R,3R,4aR,10aR)-4a-Ethyl-3-methyl-2-pyridin-4-yl-1,2,3,4,4a,9,10,10a-octahydrophenanthrene-2,3,7-triol

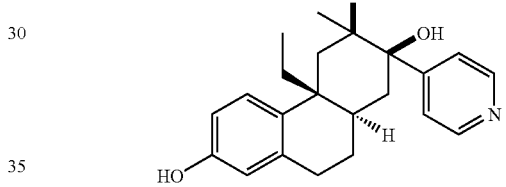

(2R,4aR,10aR)-7-(tert-butyldimethylsilanyloxy)-4a-ethyl-2-hydroxy-2-pyridin-4-yl-1,4,4a,9,10,10a-hexahydro-2H-phenanthren-3-one was prepared from the compound of Preparation 12a and 4-bromopyridine by a sequence of reactions analogous to Preparations 12b–d and 11f.

A solution of (2R,4aR,10aR)-7-(tert-butyidimethylsilanyloxy)-4a-ethyl-2-hydroxy-2-pyridin-4-yl-1,4,4a,9,10,10a-hexahydro-2H-phenanthren-3-one (32 mg, 0.65 mmol) in tetrahydrofuran (5 mL) was cooled to −78° C. and treated with a 1.0 M solution of methyllithium/lithium iodide complex in tetrahydrofuran (0.65 mL, 0.65 mmol). The mixture was allowed to stir from −78° C. to room temperature over 3 days and was then quenched with saturated aqueous ammonium chloride solution and water. The mixture was extracted four times with ethyl acetate. The combined extracts were washed with brine, dried over sodium sulfate and concentrated to a solid that was triturated with hexane and diethyl ether. The title compound (3 mg, 13%) was isolated from the solid by chromatography on silica gel eluting with a gradient of 50% ethyl acetate in hexane to 100% ethyl acetate. Mass spectrum (m/e) 354 (M$^+$+1).

Example 105

(2R,3R,4aR,10aR)-4a-Ethyl-3-methyl-7-(2-methylpyridin-3-ylmethoxy)-2-pyridin-2-yl-1,2,3,4,4a,9,10,10a-octahydrophenanthrene-2,3-diol

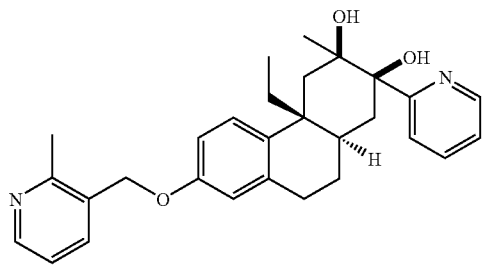

The title compound was prepared from the compound of Example 102 according to the procedure of Example 57 running the reaction at room temperature overnight. Mass spectrum (m/e) 459 (M$^+$+1).

Example 106

(4bR,6R,7R,8aR)-2-(4b-Ethyl-6,7-dihydroxy-6-methyl-7-pyridin-2-yl-4b,5,6,7,8,8a,9,10-octahydrophenanthren-2-yloxy)acetamide

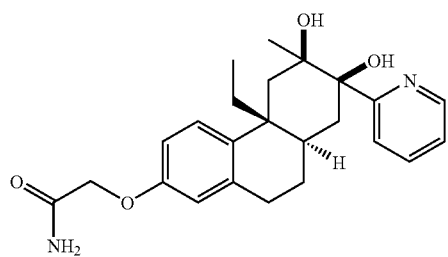

The title compound was prepared from the compound of Example 102 according to the procedure of Example 57, running the reaction at room temperature overnight and using iodoacetamide as the alkylating agent. Mass spectrum (m/e) 411 (M$^+$+1).

Example 107

(4bR,6R,7R,8aR)-(4b-Ethyl-6,7-dihydroxy-6-methyl-7-pyridin-2-yl-4b,5,6,7,8,8a,9,10-octahydrophenanthren-2-yloxy)acetonitrile

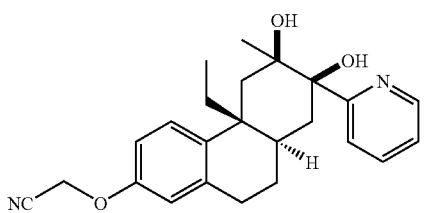

The title compound was prepared from the compound of Example 102 according to the procedure of Example 57, running the reaction at room temperature overnight and using chloroacetonitrile as the alkylating agent. Mass spectrum (m/e) 393 (M$^+$+1).

Example 108

(2R,3R,4aR,10aR)-7-[5-(2-Azetidin-1-yl-ethyl)-[1,2,4]oxadiazol-3-ylmethoxyl-4a-ethyl-3-methyl-2-pyridin-2-yl-1,2,3,4,4a,9,10,10a-octahydrophenanthrene-2,3-diol

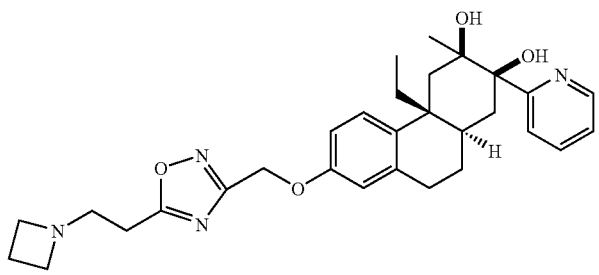

The title compound was prepared from the compound of Example 107 according to the procedure of Example 90 using ethyl 2-(azetidin-1-yl) propionate in the condensation with the N-hydroxyamidine intermediate. Mass spectrum (m/e) 519 (M⁺+1).

Example 109

(4bR,6R,7R,8aR)-N-[3-(4b-Ethyl-6,7-dihydroxy-6-methyl-7-pyridin-2-yl-4b,5,6,7,8,8a,9,10-octahydr-phenanthren-2-yloxymethyl)-[1,2,4]oxadiazol-5-ylmethyl]acetamide

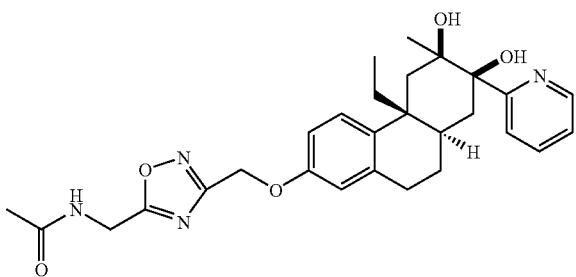

The title compound was prepared from the compound of Example 107 according to the procedure of Example 90 using ethyl acetamidoacetate in the condensation with the N-hydroxyamidine intermediate. Mass spectrum (m/e) 507 (M⁺+1).

Example 110

(2R,3R,4aR,10aR)-7-[5-(2-Dimethylaminoethyl)-[1,2,4]oxadiazol-3-ylmethoxy]-4a-ethyl-3-methyl-2-pyridin-2-yl-1,2,3,4,4a,9,10,10a-octahydrophenanthrene-2,3-diol

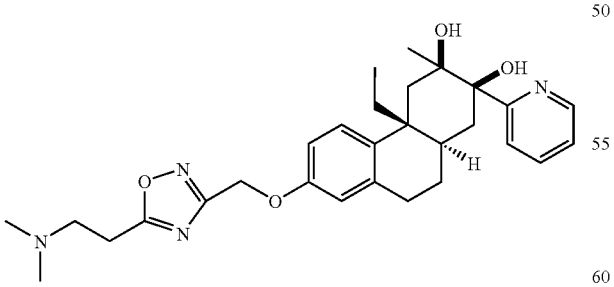

The title compound was prepared from the compound of Example 107 according to the procedure of Example 90 using ethyl 3-(N,N-dimethylamino) propionate in the condensation with the N-hydroxyamidine intermediate. Mass spectrum (m/e) 507 (M⁺+1).

Example 111

(2R,3R,4aR,10aS)-4a-Ethyl-2,3,7-trihydroxy-3-methyl-2-pyridin-2-yl-2,3,4,4a,10,10a-hexahydro-1H-phenanthren-9-one

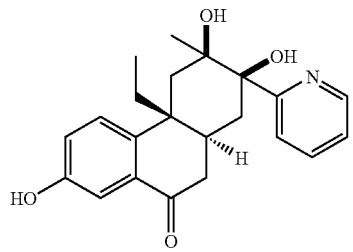

A solution of the compound of Example 102 (80 mg, 0.23 mmol) in acetone (15 mL) was cooled to 0° C. p-Nitrobenzoyl chloride (46 mg, 0.25 mmol) and aqueous 1N sodium hydroxide solution were then added. After the mixture was stirred at 0° C. for 1.5 hours, aqueous saturated sodium bicarbonate solution was added. The mixture was extracted with ethyl acetate and the organic layer was washed with brine, dried over magnesium sulfate and concentrated to afford the crude p-nitrobenzoyl ester derivative. This was dissolved in dichloromethane (15 mL) and treated with aqueous 6N hydrochloric acid solution (0.038 mL). After it was cooled to −30° C., ozone was bubbled through the solution until disappearance of starting material was evident by thin layer chromatography. Oxygen was bubbled for an additional 5 minutes and then dimethylsulfide (0.5 mL) was added. The mixture was allowed to warm to room temperature overnight and was then concentrated. The residue was taken up in tetrahydrofuran (10 mL), treated with aqueous 1N sodium hydroxide solution (5 mL) and stirred at room temperature for 2 hours. Excess aqueous 1N hydrochloric acid solution was added and the mixture was extracted with ethyl acetate. The organic phase was washed with saturated aqueous sodium bicarbonate solution and brine. After drying over magnesium sulfate, evaporation provided a residue from which the title compound was isolated by chromatography on silica gel eluting with 40% ethyl acetate in hexane. Mass spectrum (m/e) 368 (M⁺+1).

Example 112

(4bR,6R,7R,8aR)-2-(4b-Ethyl-6,7-dihydroxy-6-methyl-10-oxo-7-pyridin-2-yl-4b,5,6,7,8,8a,9,10-octahydrophenanthren-2-yloxy)acetamide

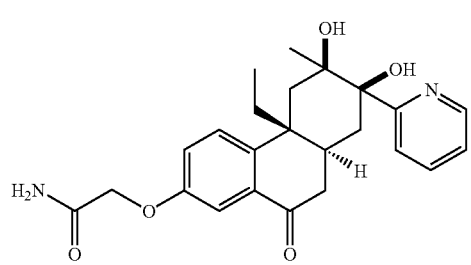

The title compound was prepared from the compound of Example 111 according to the procedure of Example 57, running the reaction at room temperature overnight and using iodoacetamide as the alkylating agent. Mass spectrum (m/e) 425 (M$^+$+1).

Examples 113 and 114

(2R,3S,4aR,10aR)-4a-Ethyl-2-pyridin-2-yl-1,2,3,4,4a,9,10,10a-octahydrophenanthrene-2,3,7-triol and (2R,3R,4aR,10aR)-4a-Ethyl-2-pyridin-2-yl-1,2,3,4,4a,9,10,10a-octahydrophenanthrene-2,3,7-triol Example 113

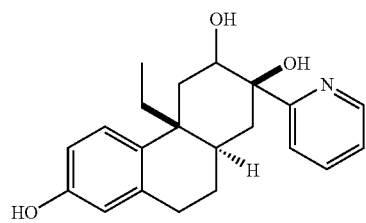

Example 114

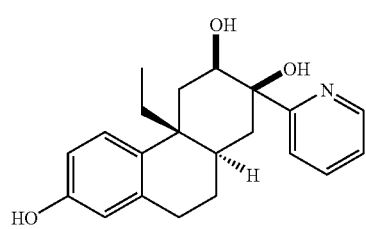

The title compounds were prepared from the compound of Example 12d according to the procedure of Examples 21 and 22. They were isolated by chromatography on silica gel eluting with a gradient of 20% to 100% ethyl acetate in hexane followed by preparative HPLC. Mass spectrum (m/e) 340 (M$^+$+1).

Example 115

(2R,3R,4aR,10aR)-4a-Ethyl-3-methyl-2-thiazol-2-yl-1,2,3,4,4a,9,10,10a-octahydrophenanthrene-2,3,7-triol

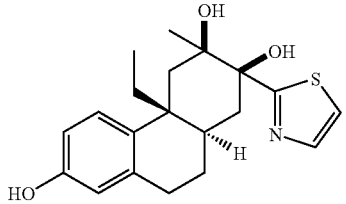

A solution of 2-bromothiazole (0.27 mL, 2.9 mmol) in tetrahydrofuran (10 mL) was cooled to −78° C. and treated with a 2.5 M solution of n-butyllithium in hexane (1.1 mL, 2.75 mmol) to give a dark solution. A solution of the compound of Preparation 11f (75 mg, 0.193 mmol) in tetrahydrofuran was then added via canula. The mixture was stirred at −78° C. for 3 hours and then quenched with aqueous saturated ammonium chloride solution. After the mixture was diluted with a little water and warmed to room temperature, it was extracted five times with ethyl acetate. The combined organic layers were washed with brine, dried over magnesium sulfate and concentrated. The residue taken up in tetrahydrofuran (5 mL), treated with a 1M solution of tetrabutylammonium fluoride in tetrahydrofuran (0.39 mL, 0.39 mmol) and stirred at room temperature overnight. The reaction mixture was filtered through a pad of Celite® and concentrated. The title compound was purified by preparative HPLC. Mass spectrum (m/e) 360 (M$^+$+1).

Example 116

(2R,3R,4aR,10aR)-2-(4,5-Dimethylthiazol-2-yl)-4a-ethyl-3-methyl-1,2,3,4,4a,9,10,10a-octahydrophenanthrene-2,3,7-triol

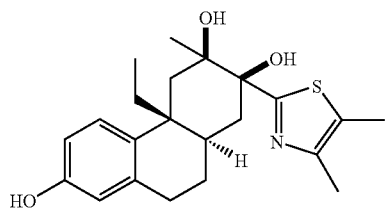

The title compound was prepared from the compound of Preparation 11f according to the procedure of Example 115 except that the nucleophile in this case was 2-lithio-3,4-dimethylthiazole generated in situ by lithiation of 3,4-dimethylthiazole over 10 minutes using 2.5 M n-butyllithium (in hexane) in tetrahydrofuran at 0° C. It was isolated by preparative HPLC. Mass spectrum (m/e) 388 (M$^+$+1).

Example 117

(2R,3R,4aR,10aR)-4a-Ethyl-3-methyl-2-(4-methylthiazol-2-yl)-1,2,3,4,4a,9,10,10a-octahydrophenanthrene-2,3,7-triol

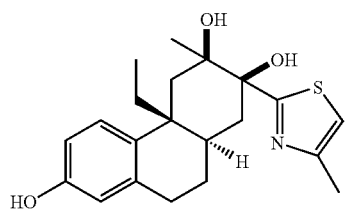

The title compound was prepared from the compound of Preparation 11f according to the procedure of Example 115 except that the nucleophile in this case was 2-lithio-4-methylthiazole generated in situ by lithiation of 4-methylthiazole using 2.5 M n-butyllithium (in hexane) in tetrahydrofuran at −78° to room temperature. It was isolated by preparative HPLC. Mass spectrum (m/e) 374 (M$^+$+1).

Example 118

(2R,3R,4aR,10aR)-4a-Ethyl-3-methyl-2-(5-methylthiazol-2-yl)-1,2,3,4,4a,9,10,10a-octahydrophenanthrene-2,3,7-triol

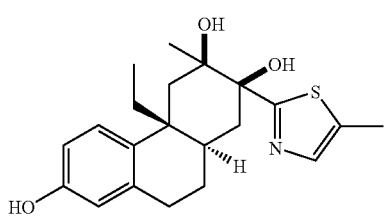

The title compound was prepared from the compound of Preparation 11f according to the procedure of Example 115 except that the nucleophile in this case was 2-lithio-5-methylthiazole generated in situ by lithiation of 3-methylthiazole using 2.5 M n-butyllithium (in hexane) in tetrahydrofuran at −780° to room temperature over 20 minutes. It was isolated by preparative HPLC. Mass spectrum (m/e) 374 ($M^+$+1).

Examples 119 and 120

(4bR,6R,7R,8aR)-1-(4b-Ethyl-6,7-dihydroxy-6-methyl-7-phenyl-4b,5,6,7,8,8a,9,10-octahydrophenanthren-2-yl)-ethanone and (4bR,6S,7R,8aR)-1-(4b-Ethyl-6,7-dihydroxy-6-methyl-7-phenyl-4b,5,6,7,8,8a,9,10-octahydrophenanthren-2-yl)-ethanone Example 119

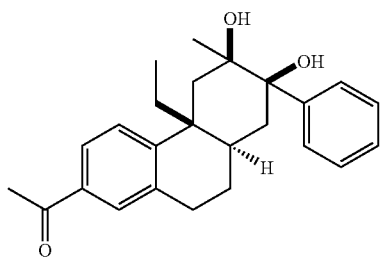

Example 120

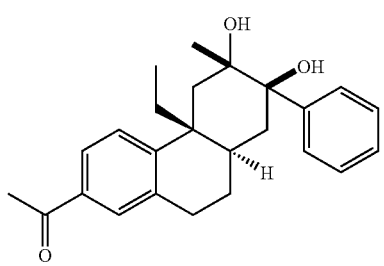

(4bR,7S,8aR)-4b-Ethyl-7-hydroxy-6-oxo-7-phenyl-4b,5,6,7,8,8a,9,10-octahydrophenanthrene-2-carbonitrile was prepared from the compound of Preparation 6c by a sequence of reactions analogous to Preparations 4a, 4b, and 4d.

(4bR,7S,8aR)-4b-Ethyl-7-hydroxy-6-oxo-7-phenyl-4b,5,6,7,8,8a,9,10-octahydrophenanthrene-2-carbonitrile (104 mg, 0.30 mmol) was dissolved in tetrahydrofuran (6 mL), cooled to 0° C. and treated with a 1.4 M solution of methyllithium in diethyl ether (2 mL, 2.8 mmol). The mixture was allowed to stir at 0° C. for 3 hours and was then quenched with aqueous saturated ammonium chloride solution. After diluting the mixture with a little water, it was extracted with ethyl acetate. The organic phase was washed with brine, dried over magnesium sulfate and concentrated. The title compounds (33 mg of the 6R isomer and 19 mg of the 6S isomer) were isolated by flash chromatography eluting with a gradient of 5% to 50% ethyl acetate in hexane. Mass spectrum (m/e) 379 ($M^+$+1).

Example 121

(2R,3R,4aR,10aR)-4a-Ethyl-7-(1-hydroxy-1-methylethyl)-3-methyl-2-phenyl-1,2,3,4,4a,9,10,10a-octahydrophenanthrene-2,3-diol

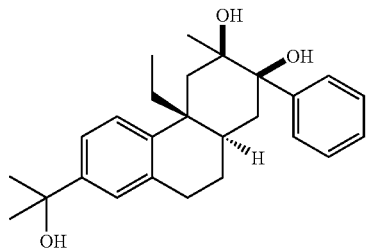

A solution of the compound of Example 119 (61 mg, 0.16 mmol) in tetrahydrofuran (5 mL) was cooled to 0° C. and treated with a 1.4 M solution of methyllithium in diethyl ether (1 mL, 1.4 mmol). The mixture was allowed to stir at 0° C. for 1 hour and was then quenched with aqueous saturated ammonium chloride solution. After diluting the mixture with a little water, it was extracted with ethyl acetate. The organic phase was washed with brine, dried over sodium sulfate and concentrated. The title compound (17 mg, 27%) was isolated by chromatography on silica gel eluting with a gradient of 5% to 50% ethyl acetate in hexane. Mass spectrum (m/e) 395 ($M^+$+1).

Example 122

(2R,3R,4aR,10aR)-2-Benzyl-4a-ethyl-3-methyl-1,2,3,4,4a,9,10,10a-octahydrophenanthrene-2,3,7-triol

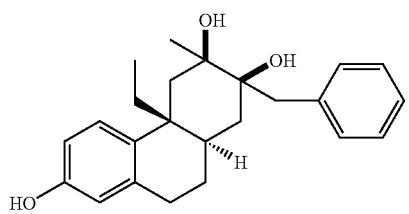

A solution of the compound of Preparation 3e (72 mg, 0.21 mmol) in tetrahydrofuran (10 mL) was cooled to 0° C. and treated with a 1.5 M solution of methyllithium/lithium iodide complex in diethyl ether (1.5 mL, 2.25 mmol). The mixture was allowed to stir at 0° C. to room temperature over 7 hours and was then quenched with aqueous saturated ammonium chloride solution. After diluting the mixture with a little water, it was extracted with ethyl acetate. The organic phase was washed with brine, dried over magnesium sulfate and concentrated. The title compound (56 mg, 73%) was isolated by chromatography on silica gel eluting with a gradient of 10% to 50% ethyl acetate in hexane. Mass spectrum (m/e) 367 ($M^+$+1).

Example 123

(2R,3S,4aR,10aR)-2-Phenyl-4a-propyl-1,2,3,4,4a,9, 10,10a-octahydro-phenanthrene-2,3,7-triol

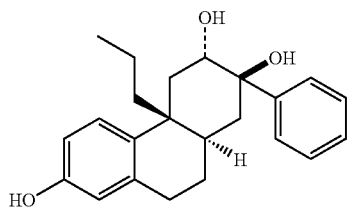

(3S,4aR,10aR)-4a-Allyl-3,7-dihydroxy-3,4,4a,9,10,10a-hexahydro-1H-phenanthren-2-one was prepared starting from the title product of Preparation 2b using procedures analogous to those of Preparations 3a and 3b. This was hydrogenated in methanol for 1.5 hours using 3 atmospheres of hydrogen and 10% palladium on charcoal as catalyst to afford (3S,4aR,10aR)-3,7-dihydroxy-4a-propyl-3,4,4a,9,10, 10a-hexahydro-1H-phenanthren-2-one. This was converted to the title compound by a procedure analogous to that for Example 10 using phenylmagnesium bromide as the nucleophile. Mass spectrum (m/e) 335 ($M^+$+1 minus $H_2O$).

What is claimed is:

1. A compound of the formula

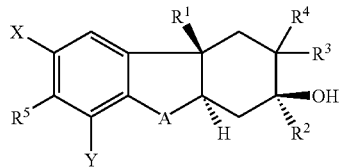

wherein A is of the formula

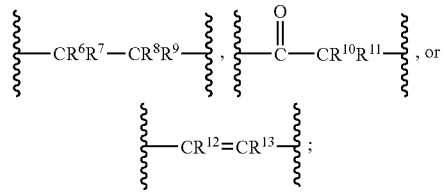

X and Y are each independently hydrogen, fluoro, chloro, bromo, or ($C_1$–$C_6$)alkyl;

$R^1$ is ($C_2$–$C_6$)alkyl, ($C_3$–$C_6$)alkenyl, or optionally substituted benzyl; wherein said benzyl may be optionally substituted with one to three substituents independently selected from HO—, ($C_1$–$C_6$)alkyl-O—, halo and amino;

$R_2$ is ($C_1$–$C_6$)alkyl, ($C_2$–$C_6$)alkenyl, ($C_3$–$C_6$)alkynyl, ($C_3$–$C_{10}$)cycloalkyl, ($C_6$–$C_{10}$)aryl, ($C_1$–$C_9$)heterocyclyl, ($C_1$–$C_9$)heteroaryl, ($C_6$–$C_{10}$)aryl($C_1$–$C_4$)alkyl, ($C_1$–$C_9$)heterocyclyl-($C_1$–$C_4$)alkyl, ($C_1$–$C_9$)heteroaryl-($C_1$–$C_4$)alkyl, or ($C_3$–$C_{10}$)cycloalkyl-($C_1$–$C_4$)alkyl; wherein each of the aforesaid groups may optionally be substituted with one to three substituents independently selected from halo, ($C_1$–$C_6$)alkyl, ($C_1$–$C_6$)alkoxy, or —$CF_3$;

$R_3$ is hydrogen, ($C_1$–$C_6$)alkyl, ($C_2$–$C_6$)alkenyl, ($C_2$–$C_6$)alkynyl, ($C_3$–$C_{10}$)cycloalkyl, ($C_1$–$C_9$)heterocyclyl, ($C_1$–$C_9$)heteroaryl, or ($C_6$–$C_{10}$)aryl; wherein each of the aforesaid groups may be optionally substituted with one to three substituents independently selected from HO—, ($C_1$–$C_6$)alkyl-O—, halo and amino;

$R^4$ is HO— or $R^{14}R^{15}N$—;

$R^5$ is a radical selected from the group consisting of hydrogen, halo, ($C_1$–$C_6$)alkyl, ($C_2$–$C_6$)alkenyl, ($C_3$–$C_6$)alkynyl, ($C_3$–$C_{10}$)cycloalkyl, ($C_6$–$C_{10}$)aryl—, ($C_1$–$C_9$)heteroaryl-, ($C_1$–$C_9$)heterocyclic-, —OH, ($C_1$–$C_6$)alkyl-O—, ($C_3$–$C_{10}$)cycloalkyl-O—, ($C_6$–$C_{10}$)aryl-O—, ($C_1$–$C_9$)heteroaryl-O—, ($C_1$–$C_9$)heterocyclic-O—, ($C_3$–$C_{10}$)cycloalkyl-($C_1$–$C_6$)alkyl-O—, ($C_6$–$C_{10}$)aryl-($C_1$–$C_6$)alkyl-O—, ($C_1$–$C_9$)heteroaryl-($C_1$–$C_6$)alkyl-O—, ($C_1$–$C_9$)heterocyclic-($C_1$–$C_6$)alkyl-O—, $R^{16}R^{17}N$—(C=O)—, $R^{16}$—(C=O)—($R^{25}$—N)—, $R^{16}R^{17}$—N—$SO_2$—, $R^{18}$—$SO_2$—, $R^{18}$—$SO_2$—($NR^{19}$)—, $R^{18}$—$SO_3$—, —C≡N, $R^{18}$—(C=O)—O—, $R^{18}$—(C=O)—, $R^{16}R^{17}N$—(C=O)—O—, $R^{16}R^{17}N$—(C=O)—($R^{25}$—N)—, $R^{19}$—O—(C=O)—($R^{25}$—N)—and $R^{19}$—O—(C=O)—; wherein each of said ($C_1$–$C_6$)alkyl, ($C_3$–$C_{10}$)cycloalkyl, ($C_6$–$C_{10}$)aryl, ($C_1$–$C_9$)heteroaryl, ($C_1$–$C_9$)heterocyclic moieties of said ($C_1$–$C_6$)alkyl, ($C_6$–$C_{10}$)aryl-, ($C_1$–$C_9$)heteroaryl-, ($C_1$–$C_9$)heterocyclic-, ($C_1$–$C_6$)alkyl-O—, ($C_3$–$C_{10}$)cycloalkyl-O—, ($C_6$–$C_{10}$)aryl-O—, ($C_1$–$C_9$)heteroaryl-O—, ($C_1$–$C_9$)heterocyclic-O—, ($C_3$–$C_{10}$)cycloalkyl-($C_1$–$C_6$)alkyl-O—, ($C_6$–$C_{10}$)aryl-($C_1$–$C_6$)alkyl-O—, ($C_1$–$C_9$)heteroaryl-($C_1$–$C_6$)alkyl-O—and ($C_1$–$C_9$)heterocyclic-($C_1$–$C_6$)alkyl-O— radicals, may optionally be substituted with one to three substituents independently selected from the group consisting of ($C_1$–$C_6$)alkyl, ($C_2$–$C_6$)alkenyl, ($C_2$–$C_6$)alkynyl, ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic, halo, HO—, HO—(C=O)—, $R^{20}$—O—(C=O)—, $R^{21}$—(C=O)—, $R^{22}$—$CO_2$—, N≡C—, $R^{23}R^{24}N$—, $R^{23}R^{24}N$—($C_1$–$C_6$)alkyl-, $R^{23}R^{24}N$—(C=O)—, $R^{23}R^{24}$—N—$SO_2$—, $R^{21}$—$SO_2$—, $R^{21}$—$SO_2$—($NR^{21}$)—, $R^{21}$—$SO_3$—, $R^{21}$(C=O)—NH—, $R^{21}$(C=O)—[N—($C_1$–$C_6$)alkyl]-; $R^{21}$(C=O)—NH—($C_1$–$C_6$)alkyl-; and $R^{21}$(C=O)—[N—($C_1$–$C_6$)alkyl]—($C_1$–$C_6$)alkyl-; wherein said ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic substituents may optionally be substituted on a ring carbon or nitrogen by one to three members per ring independently selected from halo, ($C_1$–$C_6$)alkyl, and ($C_1$–$C_6$)alkoxy;

n is an integer from zero to four;

each of $R^6$, $R^7$, $R^8$ and $R^9$ is independently selected from the group consisting of hydrogen, ($C_1$–$C_6$)alkyl, fluoro and —OH;

each of $R^{10}$ and $R^{11}$ is independently selected from the group consisting of hydrogen and ($C_1$–$C_6$)alkyl;

each of $R^{12}$ and $R^{13}$ is independently selected from the group consisting of hydrogen, fluoro and ($C_1$–$C_6$)alkyl;

each of $R^{14}$ and $R^{15}$ is independently selected from hydrogen or ($C_1$–$C_4$)alkyl;

each of $R^{16}$ and $R^{17}$ is independently selected from hydrogen, $(C_1-C_6)$alkyl, $(C_6-C_{10})$aryl, $(C_1-C_9)$heteroaryl, $(C_1-C_9)$heterocyclic, $(C_1-C_9)$heteroaryl$(C_1-C_6)$alkyl, $(C_6-C_{10})$aryl$(C_1-C_6)$alkyl, $(C_1-C_9)$heterocyclic$(C_1-C_6)$alkyl, HO—$(C_1-C_6)$alkyl, amino-$(C_1-C_6)$alkyl-, $(C_1-C_6)$alkylamino-$(C_1-C_6)$alkyl-, and $[(C_1-C_6)$alkyl$]_2$amino-$(C_1-C_6)$alkyl-;

wherein said each of said $(C_6-C_{10})$aryl, $(C_1-C_9)$heteroaryl, and $(C_1-C_9)$heterocyclic moieties of said $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl and $(C_1-C_9)$heterocyclic-$(C_1-C_6)$alkyl, may optionally be substituted with one to three substituents independently selected from the group consisting of halo, $(C_1-C_6)$alkyl or $(C_1-C_6)$alkoxy, or $R^{16}$ and $R^{17}$ are taken together to form an azetidinyl, pyrrolidinyl, piperidinyl, piperazinyl, $(C_1-C_6)$alkyl-piperazinyl, or morpholinyl ring;

$R_{18}$ is hydrogen, $(C_1-C_6)$alkyl, $(C_6-C_{10})$aryl or $(C_1-C_9)$heteroaryl; wherein said $(C_1-C_6)$alkyl may optionally be substituted with a substituent selected from the group consisting of HO—, amino, $(C_1-C_6)$alkylamino, $[(C_1-C_6)$alkyl$]_2$amino, $(C_6-C_{10})$aryl, $(C_1-C_9)$heteroaryl, $(C_1-C_9)$heterocyclic, $(C_1-C_6)$alkoxy, HO—(C=O)—, $(C_1-C_6)$alkyl-O—(C=O)—, $(C_1-C_6)$alkyl-(C=O)—, N≡C—, $[(C_1-C_6)$alkyl$]_2$N—(C=O)—and $(C_1-C_6)$alkyl(C=O)—NH—;

$R^{19}$ is hydrogen or $(C_1-C_6)$alkyl;

$R^{20}$ is hydrogen or $(C_1-C_6)$alkyl;

$R^{21}$ is hydrogen or $(C_1-C_6)$alkyl;

$R^{22}$ is hydrogen or $(C_1-C_6)$alkyl;

each of $R^{23}$ and $R^{24}$ is independently selected from hydrogen, $(C_1-C_6)$alkyl, $(C_6-C_{10})$aryl, $(C_1-C_9)$heteroaryl, $(C_1-C_9)$heterocyclic, $(C_1-C_9)$heteroaryl$(C_1-C_6)$alkyl, $(C_6-C_{10})$aryl$(C_1-C_6)$alkyl, $(C_1-C_9)$heterocyclic$(C_1-C_6)$alkyl, HO—$(C_1-C_6)$alkyl, N≡C—$(C_1-C_6)$alkyl, amino-$(C_1-C_6)$alkyl-, $(C_1-C_6)$alkylamino-$(C_1-C_6)$alkyl-, and $[(C_1-C_6)$alkyl$]_2$amino-$(C_1-C_6)$alkyl-; wherein said each of said $(C_6-C_{10})$aryl, $(C_1-C_9)$heteroaryl, and $(C_1-C_9)$heterocyclic moieties of said $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl and $(C_1-C_9)$heterocyclic-$(C_1-C_6)$alkyl, may optionally be substituted with one to three substituents independently selected from the group consisting of halo, $(C_1-C_6)$alkyl or $(C_1-C_6)$alkoxy, or $R^{23}$ and $R^{24}$ are taken together to form an azetidinyl, pyrrolidinyl, piperidinyl, piperazinyl, $(C_1-C_6)$alkyl-piperazinyl, or morpholinyl ring;

$R^{25}$ is hydrogen or $(C_1-C_6)$alkyl;

or a pharmaceutically acceptable salt thereof.

2. A compound according to claim 1, wherein said compound has the formula

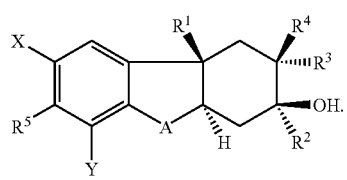

3. A compound according to claim 1, wherein said compound has the formula

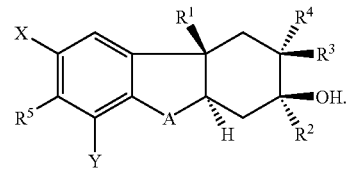

4. A compound according to claim 1, wherein said compound has the formula

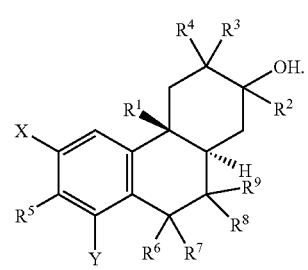

1a

5. A compound according to claim 1, wherein said compound has the formula

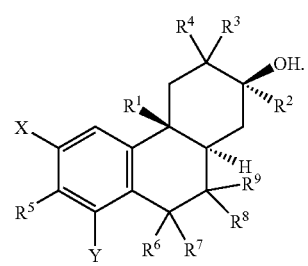

6. A compound according to claim 1, wherein said compound has the formula

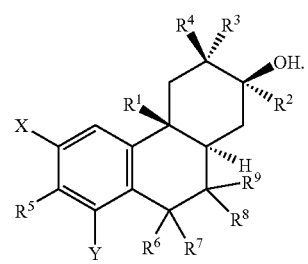

7. A compound according to claim 1, wherein said compound has the formula

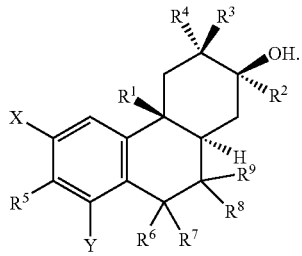

8. A compound according to claim 1, wherein said compound has the formula

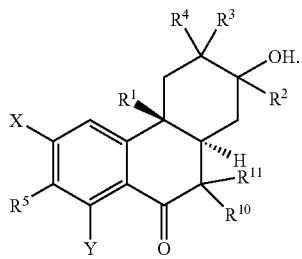

9. A compound according to claim 1, wherein said compound has the formula

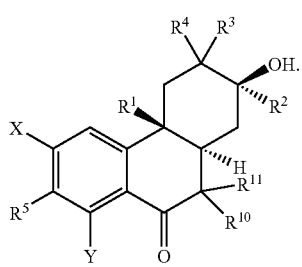

10. A compound according to claim 1, wherein said compound has the formula

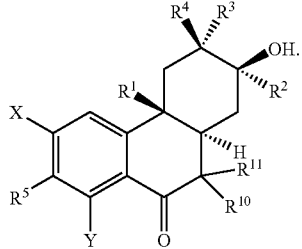

11. A compound according to claim 1, wherein said compound has the formula

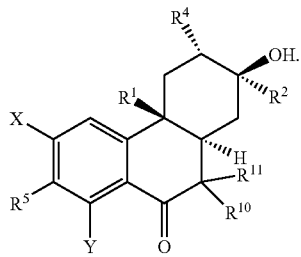

12. A compound according to claim 1, wherein said compound has the formula

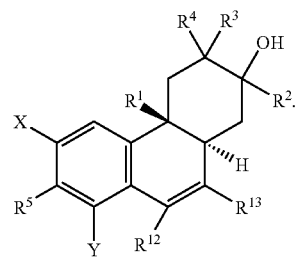

13. A compound according to claim 1, wherein said compound has the formula

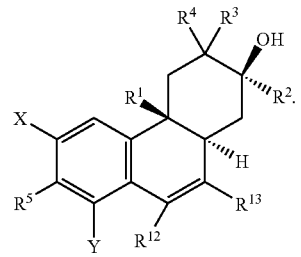

14. A compound according to claim 1, wherein said compound has the formula

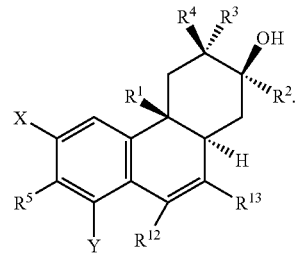

15. A compound according to claim 1, wherein said compound has the formula

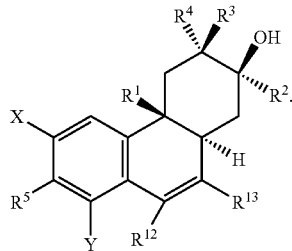

16. A compound according to claim 1, wherein $R^1$ is ethyl or allyl.

17. A compound according to claim 1, wherein $R^2$ is optionally substituted $(C_6-C_{10})$aryl.

18. A compound according to claim 1, wherein $R^2$ is optionally substituted $(C_1-C_9)$heteroaryl.

19. A compound according to claim 1, wherein $R^2$ is optionally substituted $(C_3-C_5)$heteroaryl.

20. A compound according to claim 1, wherein $R^2$ is optionally substituted $(C_1-C_9)$heterocyclyl.

21. A compound according to claim 1, wherein $R^2$ is optionally substituted phenyl.

22. A compound according to claim 1, wherein $R^2$ is phenyl.

23. A compound according to claim 1, wherein $R^2$ is optionally substituted thiazolyl.

24. A compound according to claim 1, wherein $R^2$ is optionally substituted pyridyl.

25. A compound according to claim 1, wherein $R^2$ is optionally substituted oxazolyl.

26. A compound according to claim 1, wherein $R^2$ is optionally substituted pyridin-2-yl.

27. A compound according to claim 1, wherein $R^2$ is optionally substituted thiazol-2-yl.

28. A compound according to claim 1, wherein $R^2$ is optionally substituted oxazol-2-yl.

29. A compound according to claim 1, wherein $R^2$ is pyridin-2-yl; optionally substituted with a substituent selected from halo, $CF_3$, and $(C_1-C_6)$alkyl.

30. A compound according to claim 1, wherein $R^2$ is thiazol-2-yl; optionally substituted with a substituent selected from halo, $CF_3$, or $(C_1-C_6)$alkyl.

31. A compound according to claim 1, wherein $R^2$ is oxazol-2-yl; optionally substituted with a substituent selected from halo, $CF_3$, or $(C_1-C_6)$alkyl.

32. A compound according to claim 1, wherein $R^2$ is pyridin-2-yl.

33. A compound according to claim 1, wherein $R^2$ is thiazol-2-yl.

34. A compound according to claim 1, wherein $R^2$ is oxazol-2-yl.

35. A compound according to claim 1, wherein $R^2$ is $(C_3-C_6)$alkynyl.

36. A compound according to claim 1, wherein $R^2$ is $(C_2-C_6)$alkenyl.

37. A compound according to claim 1, wherein $R^3$ is hydrogen.

38. A compound according to claim 1, wherein $R^3$ is $(C_1-C_6)$alkyl optionally substituted with a substituent selected from halo or hydroxy.

39. A compound according to claim 1, wherein $R^3$ is methyl, ethyl or propyl.

40. A compound according to claim 1, wherein $R^3$ is methyl.

41. A compound according to claim 1, wherein $R^3$ is optionally substituted $(C_1-C_9)$heteroaryl.

42. A compound according to claim 1, wherein $R^3$ is optionally substituted $(C_1-C_9)$heterocyclyl.

43. A compound according to claim 1, wherein $R^3$ is optionally substituted $(C_6-C_{10})$aryl.

44. A compound according to claims 1, 4, 5, 6, and 7 wherein $R^4$ is HO—.

45. A compound according to claim 1, wherein $R^4$ is $R^{14}R^{15}N$—.

46. A compound according to claim 1, wherein $R^5$ is —OH.

47. A compound according to claim 1, wherein $R^5$ is $(C_1-C_6)$alkyl-O—, $(C_3-C_{10})$cycloalkyl-O—, $(C_6-C_{10})$aryl-O—, $(C_1-C_9)$heteroaryl-O—, or $(C_1-C_9)$heterocyclic-O—, wherein each of said $(C_1-C_6)$alkyl, $(C_3-C_{10})$cycloalkyl, $(C_6-C_{10})$aryl, $(C_1-C_9)$heteroaryl, $(C_1-C_9)$heterocyclic moieties of said $(C_1-C_6)$alkyl-O—, $(C_3-C_{10})$cycloalkyl-O—, $(C_6-C_{10})$aryl-O—, $(C_1-C_9)$heteroaryl-O—, $(C_1-C_9)$heterocyclic-O— radicals may optionally be substituted with one to three substituents independently selected from $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl, $(C_1-C_9)$heterocyclic, halo, HO—, HO—(C=O)—, $R^{21}$—(C=O)—, $R^{22}$—$CO_2$—, N≡C—, $R^{23}R^{24}N$—, $R^{23}R^{24}N$—(C=O)—, $R^{21}$(C=O)—NH—, $R^{21}$(C=O)—[N—$(C_1-C_6)$alkyl]-.

48. A compound according to claim 1, wherein $R^5$ is optionally substituted $(C_6-C_{10})$aryl-, $(C_1-C_9)$heteroaryl-, $(C_1-C_9)$heterocyclic-, $(C_6-C_{10})$aryl-$(C_1-C_6)$alkyl, $(C_1-C_9)$heteroaryl-$(C_1-C_6)$alkyl or $(C_1-C_9)$heterocyclic-$(C_1-C_6)$alkyl; optionally substituted with one to three substituents independently selected from $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl, $(C_1-C_9)$heterocyclic, halo, HO—, HO—(C=O)—, $R^{21}$—(C=O)—, $R^{22}$—$CO_2$—, N≡C—, $R^{23}R^{24}N$—, $R^{23}R^{24}N$—(C=O)—, $R^{21}$(C=O)—NH—, $R^{21}$(C=O)—[N—$(C_1-C_6)$alkyl]-.

49. A compound according to claim 1, wherein $R^5$ is $(C_6-C_{10})$aryl-$(C_1-C_6)$alkyl-O—, $(C_1-C_9)$heteroaryl-$(C_1-C_6)$alkyl-O—, $(C_1-C_9)$heterocyclic-$(C_1-C_6)$alkyl-O—, wherein each of said $(C_6-C_{10})$aryl, $(C_1-C_9)$heteroaryl, $(C_1-C_9)$heterocyclic moieties of said $(C_6-C_{10})$aryl-$(C_1-C_6)$alkyl-O—, $(C_1-C_9)$heteroaryl-$(C_1-C_6)$alkyl-O—, and $(C_1-C_9)$heterocyclic-$(C_1-C_6)$alkyl-O—, may optionally be substituted with one to three substituents independently selected from the group consisting of $(C_1-C_6)$alkyl, $(C_2-C_6)$alkenyl, $(C_2-C_6)$alkynyl, $(C_3-C_{10})$cycloalkyl, $(C_6-C_{10})$aryl, $(C_1-C_9)$heteroaryl$(CH_2)_n$—, $(C_1-C_9)$heterocyclic, halo, HO—, HO—(C=O)—, $R^{20}$—O—(C=O)—, $R^{21}$—(C=O)—$R^{22}$—$CO_2$—N≡C—$R^{23}R^{24}N$—$R^{23}R^{24}N$—$(C_1-C_6)$alkyl-, $R^{23}R^{24}N$—(C=O)—, $R^{21}$(C=O)—NH—, $R^{21}$(C=O)—[N—$(C_1-C_6)$alkyl]-; $R^{21}$ (C=O)—NH—$(C_1-C_6)$alkyl-; and $R^{21}$(C=O)—[N—$(C_1-C_6)$alkyl]-$(C_1-C_6)$alkyl-; wherein said $(C_3-C_{10})$cycloalkyl, $(C_6-C_{10})$aryl, $(C_1-C_9)$heteroaryl$(CH_2)_n$—, $(C_1-C_9)$heterocyclic substituents may optionally be substituted on a ring carbon or nitrogen by one to three members per ring independently selected from halo, $(C_1-C_6)$alkyl, and $(C_1-C_6)$alkoxy.

50. A compound according to claim 1, wherein $R^5$ is $(C_6-C_{10})$aryl-$(C_1-C_6)$alkyl-O—, $(C_1-C_9)$heteroaryl-$(C_1-C_6)$alkyl-O—, $(C_1-C_9)$heterocyclic-$(C_1-C_6)$alkyl-O—, wherein each of said $(C_6-C_{10})$aryl, $(C_1-C_9)$heteroaryl, $(C_1-C_9)$heterocyclic moieties of said $(C_6-C_{10})$aryl-$(C_1-C_6)$ alkyl-O—, ($C_1$–$C_9$)heteroaryl-($C_1$–$C_6$)alkyl-O—, and ($C_1$–$C_9$)heterocyclic-($C_1$–$C_6$)alkyl-O—, may optionally be substituted with a substituent selected from the group consisting of ($C_1$–$C_6$)alkyl, ($C_2$–$C_6$)alkenyl, ($C_2$–$C_6$)alkynyl, ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic, halo, HO—, HO—(C=O)—, $R^{20}$—O—(C=O)—, $R^{21}$—(C=O)—, $R^{22}$—$CO_2$—, N≡C—, $R^{23}R^{24}$N—, $R^{23}R^{24}$N—($C_1$–$C_6$)alkyl-, $R^{23}R^{24}$N—(C=O)—, $R^{21}$(C=O)—NH—, $R^{21}$(C=O)—[N—($C_1$–$C_6$)alkyl]-; $R^{21}$ (C=O)—NH—($C_1$–$C_6$)alkyl-; and $R^{21}$ (C=O)—[N—($C_1$–$C_6$)alkyl]-($C_1$–$C_6$)alkyl-; wherein said ($C_3$–$C_{10}$)cycloalkyl, ($C_6$–$C_{10}$) aryl, ($C_1$–$C_9$)heteroaryl($CH_2$)$_n$—; ($C_1$–$C_9$)heterocyclic substituents may optionally be substituted on a ring carbon or nitrogen by one to three members per ring independently selected from halo, ($C_1$–$C_6$)alkyl, and ($C_1$–$C_6$)alkoxy.

51. A compound according to claim 1, wherein $R^5$ is ($C_1$–$C_9$)heteroaryl-($C_1$–$C_6$)alkyl-O— optionally substituted with one to two substituents independently selected from the group consisting of ($C_1$–$C_6$)alkyl, ($C_2$–$C_6$)alkenyl, ($C_2$–$C_6$)alkynyl, ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic, halo, HO—, HO—(C=O)—, $R^{20}$—O—(C=O)—$R^{21}$—(C=O)—, $R^{22}$—$CO_2$—N≡C—, $R^{23}R^{24}$N—, $R^{23}R^{24}$N—($C_1$–$C_6$)alkyl-, $R^{23}R^{24}$N—(C=O)—, $R^{21}$(C=O)—NH—, $R^{21}$(C=O)-[N—($C_1$–$C_6$)alkyl]-; $R^{21}$(C=O)—NH—($C_1$–$C_6$)alkyl-; and $R^{21}$(C=O)—[N—($C_1$–$C_6$)alkyl]-($C_1$–$C_6$)alkyl-;
   wherein said ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic substituents may optionally be substituted on a ring carbon or nitrogen by one to three members per ring independently selected from halo, ($C_1$–$C_6$)alkyl, and ($C_1$–$C_6$)alkoxy.

52. A compound according to claim 1, wherein $R^5$ is ($C_1$–$C_9$)heteroaryl-($C_1$–$C_6$)alkyl-O— optionally substituted with one to two substituents independently selected from the group consisting of ($C_1$–$C_6$)alkyl, ($C_6$–$C_{10}$)aryl, ($C_1$–$C_9$)heteroaryl($CH_2$)$_n$—, halo, HO—, HO—(C=O)—, $R^{20}$—O—(C=O)—, $R^{21}$—(C=O)—$R^{22}$—$CO_2$—, N≡C—, $R^{23}R^{24}$N—, $R^{23}R^{24}$N—($C_1$–$C_6$)alkyl-, $R^{23}R^{24}$N—(C=O)—, $R^{21}$(C=O)—NH—, $R^{21}$(C=O)—[N—($C_1$–$C_6$) alkyl]-; $R^{21}$(C=O)—NH—($C_1$–$C_6$)alkyl-; and $R^{21}$ (C=O)—[N—($C_1$–$C_6$)alkyl]-($C_1$–$C_6$)alkyl-; wherein said ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic substituents may optionally be substituted on a ring carbon or nitrogen by one to two members per ring independently selected from halo, ($C_1$–$C_6$)alkyl, and ($C_1$–$C_6$)alkoxy;
   wherein n is an integer from zero to two;
   wherein each of $R^{23}$ and $R^{24}$ is independently selected from hydrogen, ($C_1$–$C_6$)alkyl, ($C_6$–$C_{10}$)aryl, ($C_1$–$C_9$)heteroaryl, ($C_1$–$C_9$)heterocyclic, ($C_1$–$C_9$)heteroaryl($C_1$–$C_6$)alkyl, ($C_6$–$C_{10}$)aryl($C_1$–$C_6$)alkyl, ($C_1$–$C_9$)heterocyclic($C_1$–$C_6$)alkyl, HO—($C_1$–$C_6$)alkyl, amino-($C_1$–$C_6$)alkyl-, ($C_1$–$C_6$)alkylamino-($C_1$–$C_6$)alkyl-, and [($C_1$–$C_6$)alkyl]$_2$amino-($C_1$–$C_6$)alkyl-; wherein said each of said ($C_6$–$C_{10}$)aryl, ($C_1$–$C_9$)heteroaryl, and ($C_1$–$C_9$)heterocyclic moieties of said ($C_6$–$C_{10}$)aryl-, ($C_1$–$C_9$)heteroaryl-, ($C_1$–$C_9$)heterocyclic-, ($C_6$–$C_{10}$) aryl-($C_1$–$C_6$)alkyl, ($C_1$–$C_9$)heteroaryl-($C_1$–$C_6$)alkyl and ($C_1$–$C_9$)heterocyclic-($C_1$–$C_6$)alkyl, may optionally be substituted with one to two substituents independently selected from the group consisting of halo, ($C_1$–$C_6$)alkyl or ($C_1$–$C_6$)alkoxy, or $R^{23}$ and $R^{24}$ are taken together to form an azetidinyl, pyrrolidinyl, piperidinyl, piperazinyl, ($C_1$–$C_6$)alkyl-piperazinyl or morpholinyl ring.

53. A compound according to claim 1, wherein $R^5$ is optionally substituted ($C_1$–$C_6$)alkyl-O—.

54. A compound according to claim 1, wherein $R^5$ is ($C_1$–$C_6$)alkyl-O-optionally substituted with one to three substituents independently selected from the group consisting of ($C_3$–$C_{10}$)cycloalkyl, ($C_6$–$C_{10}$)aryl, ($C_1$–$C_9$)heteroaryl and ($C_1$–$C_9$)heterocyclic; wherein said ($C_3$–$C_{10}$)cycloalkyl, ($C_6$–$C_{10}$)aryl, ($C_1$–$C_9$)heteroaryl($CH_2$)$_n$—, ($C_1$–$C_9$)heterocyclic substituents may optionally be substituted on a ring carbon or nitrogen by one to three members per ring independently selected from halo, ($C_1$–$C_6$)alkyl, and ($C_1$–$C_6$)alkoxy.

55. A compound according to claim 1, wherein $R^5$ is ($C_1$–$C_6$)alkyl-O-substituted with one substituent selected from the group consisting of halo, HO—, HO—(C=O)—, $R^{20}$—(C=O)—, $R^{21}$—(C=O)—, $R^{22}CO_2$—, N≡C—, $R^{23}R^{24}$N—, $R^{23}R^{24}$N—(C=O)—, $R^{21}$ (C=O)—NH—, and $R^{21}$(C=O)—[N—($C_1$–$C_6$)alkyl]-; wherein $R^{23}$ and $R^{24}$ is independently selected from hydrogen, ($C_1$–$C_6$)alkyl, ($C_6$–$C_{10}$)aryl, ($C_1$–$C_9$)heteroaryl, ($C_1$–$C_9$)heterocyclic, ($C_1$–$C_9$)heteroaryl($C_1$–$C_6$)alkyl, ($C_6$–$C_{10}$)aryl($C_1$–$C_6$)alkyl, ($C_1$–$C_9$)heterocyclic($C_1$–$C_6$)alkyl, HO—($C_1$–$C_6$)alkyl, N≡C—($C_1$–$C_6$)alkyl, amino-($C_1$–$C_6$)alkyl-, ($C_1$–$C_6$)alkylamino-($C_1$–$C_6$)alkyl-, and [($C_1$–$C_6$)alkyl]$_2$amino-($C_1$–$C_6$) alkyl-; wherein said each of said ($C_6$–$C_{10}$)aryl, ($C_1$–$C_9$)heteroaryl, and ($C_1$–$C_9$)heterocyclic moieties of said ($C_6$–$C_{10}$)aryl-, ($C_1$–$C_9$)heteroaryl-, ($C_1$–$C_9$)heterocyclic-, ($C_6$–$C_{10}$)aryl-($C_1$–$C_6$)alkyl, ($C_1$–$C_9$)heteroaryl-($C_1$–$C_6$) alkyl and ($C_1$–$C_9$)heterocyclic-($C_1$–$C_6$)alkyl, may optionally be substituted with one to two substituents independently selected from the group consisting of halo, ($C_1$–$C_6$) alkyl or ($C_1$–$C_6$)alkoxy, or $R^{23}$ and $R^{24}$ are taken together to form an azetidinyl, pyrrolidinyl, piperidinyl or morpholinyl ring.

56. A compound according to claims 1, 4, 5, 6 or 7, wherein $R^5$ is —C≡N, $R^{16}R^{17}$N—(C=O)—, $R^{16}R^{17}$—N—$SO_2$—, $R^{18}$—$SO_2$—, $R^{18}$—$SO_2$—(N$R^{19}$)—, $R^{18}SO_3$, $R^{16}$—(C=O)—($R^{25}$—N)—, $R^{16}R^{17}$N—(C=O)—($R^{25}$—N)—, $R^{19}$—O—(C=O)—($R^{25}$—N)—, $R^{18}$—(C=O)—O—, $R^{18}$—(C=O)—, $R^{16}R^{17}$N—(C=O)—O— or $R^{19}$—O—(C=O)—.

57. A compound according to claims 1, 4, 5, 6 or 7, wherein $R^5$ is $R^{16}R^{17}$N—(C=O)—.

58. A compound according to claim 1, wherein X and Y are each hydrogen.

59. A compound according to claim 1, wherein one of X and Y is fluoro, chloro, or bromo.

60. A compound according to claim 1, wherein each of X and Y are independently selected from hydrogen, fluoro, chloro, or bromo.

61. A compound according to claim 1, wherein one of X and Y is ($C_1$–$C_6$)alkyl.

62. A compound according to claim 1, wherein said compound is
   (2R,3S,4aR,10aR)-4a-Ethyl-2-prop-1-ynyl-1,2,3,4,4a,9,10,10a-octahydrophenanthrene-2,3,7-triol;
   (2R,3S,4aR,10aR)-4a-Ethyl-7-(2-methylpyridin-3-ylmethoxy)-2-prop-1-ynyl-1,2,3,4,4a,9,10,10a-octahydrophenanthrene-2,3-diol;
   (2R,3R,4aR,10aR)-7-[5-(2-Dimethylaminoethyl)-[1,2,4] oxadiazol-3-ylmethoxy]-4a-ethyl-3-methyl-2-phenyl-1,2,3,4,4a,9,10,10a-octahydrophenanthrene-2,3-diol
   (2R,3R,4aR,10aR)-4a-Ethyl-3-methyl-2-pyridin-2-yl-1,2,3,4,4a,9,10,10a-octahydrophenanthrene-2,3,7-triol;
   (2R,3R,4aR,10aR)-4a-Ethyl-3-methyl-7-(2-methylpyridin-3-ylmethoxy)-2-pyridin-2-yl-1,2,3,4,4a,9,10,10a-octahydrophenanthrene-2,3-diol;

(2R,3S,4aR,10aR)-4a-Ethyl-3-methyl-2-thiazol-2-yl-1,2,3,4,4a,9,10,10a-octahydrophenanthrene-2,3,7-triol;

(2R,3S,4aR,10aR)-4a-Ethyl-3-methyl-2-(4-methylthiazol-2-yl)-1,2,3,4,4a,9,10,10a-octahydrophenanthrene-2,3,7-triol;

(2R,3R,4aR,10aS)-4a-Ethyl-2,3,7-trihydroxy-3-methyl-2-phenyl-2,3,4,4a,10,10a-hexahydro-1H-phenanthren-9-one;

(2R,3R,4aR,10aS)-4a-Ethyl-3,9-dimethyl-2-phenyl-1,2,3,4,4a,10a-hexahydro-phenanthrene-2,3,7-triol;

(2R,3R,4aR,10aR)-3,4a-Diethyl-2-phenyl-1,2,3,4,4a,9,10,10a-octahydro-phenanthrene-2,3,7-triol;

(2R,3R,4aR,10aR)-4a-Ethyl-7-(2-hydroxy-ethoxy)-3-methyl-2-phenyl-1,2,3,4,4a,9,10,10a-octahydro-phenanthrene-2,3-diol;

(2R,3R,4aR,10aR)-4a-Ethyl-7-(3-hydroxy-propoxy)-3-methyl-2-phenyl-1,2,3,4,4a,9,10,10a-octahydro-phenanthrene-2,3-diol;

(2R,3R,4aR,10aR)-4a-Ethyl-7-(4-hydroxy-butoxy)-3-methyl-2-phenyl-1,2,3,4,4a,9,10,10a-octahydro-phenanthrene-2,3-diol;

(4bR,7R,6R,8aR)-4-(4b-Ethyl-6,7-dihydroxy-6-methyl-7-phenyl-4b,5,6,7,8,8a,9,10-octahydro-phenanthren-2-yloxy)-butyronitrile;

(4bR,7R,6R,8aR)-5-(4b-Ethyl-6,7-dihydroxy-6-methyl-7-phenyl-4b,5,6,7,8,8a,9,10-octahydro-phenanthren-2-yloxy)-pentanenitrile;

(4bR,7R,6R,8aR)-2-(4b-Ethyl-6,7-dihydroxy-6-methyl-7-phenyl-4b,5,6,7,8,8a,9,10-octahydro-phenanthren-2-yloxy)-acetamide;

(2R,3R,4aR,10aR)-4a-Ethyl-7-(4-hydroxy-4-methyl-pentyloxy)-3-methyl-2-phenyl-1,2,3,4,4a,9,10,10a-octahydro-phenanthrene-2,3-diol;

(2R,3R,4aR,10aR)-4a-Ethyl-7-(5-hydroxy-5-methyl-hexyloxy)-3-methyl-2-phenyl-1,2,3,4,4a,9,10,10a-octahydro-phenanthrene-2,3-diol;

(2R,3R,4aR,10aR)-4a-Ethyl-3-methyl-2-prop-1-ynyl-1,2,3,4,4a,9,10,10a-octahydro-phenanthrene-2,3,7-triol;

(2R,3R,4aR,10aR)-4a-Ethyl-3-methyl-2-p-tolyl-1,2,3,4,4a,9,10,10a-octahydro-phenanthrene-2,3,7-triol; and (2R,3R,4aR,10aR)-4a-Ethyl-3-methyl-2-propenyl-1,2,3,4,4a,9,10,10a-octahydro-phenanthrene-2,3,7-triol.

63. A pharmaceutical composition comprising a therapeutically effective amount of a compound according to claim 1 or a salt and a pharmaceutically acceptable carrier.

64. A compound according to claims 1, 4, 5, 6, or 7, wherein $R^4$ is HO—; and $R^5$ is —C≡N, $R^{16}R^{17}N$—(C=O)—, $R^{16}R^{17}$—N—SO$_2$—, $R^{18}$—SO$_2$—, $R^{18}$—SO$_2$—(NR$^{19}$)—, $R^{18}$—SO$_3$—, $R^{16}$—(C=O)—(R$^{25}$—N—)—, $R^{16}R^{17}N$—(C=O)—(R$^{25}$—N—)—, $R^{19}$—O—(C=O)—(R$^{25}$—N—), $R^{18}$—(C=O)—O—, $R^{18}$—(C=O)—, $R^{16}R^{17}N$—(C=O)—O—or $R^{19}$—O—(C=O)—.

* * * * *